(12) United States Patent
Hirota et al.

(10) Patent No.: US 12,180,533 B2
(45) Date of Patent: *Dec. 31, 2024

(54) TRANSFORMANT, AND METHOD USING SAID TRANSFORMANT TO DETECT PRESENCE OR ABSENCE OF REDUCED PHOSPHOROUS COMPOUND

(71) Applicant: HIROSHIMA UNIVERSITY, Hiroshima (JP)

(72) Inventors: Ryuichi Hirota, Hiroshima (JP); Akio Kuroda, Hiroshima (JP); Kei Motomura, Hiroshima (JP)

(73) Assignee: HIROSHIMA UNIVERSITY, Hiroshima (JP)

( * ) Notice: Subject to any disclaimer, the term of this patent is extended or adjusted under 35 U.S.C. 154(b) by 356 days.

This patent is subject to a terminal disclaimer.

(21) Appl. No.: 16/976,267

(22) PCT Filed: Mar. 1, 2019

(86) PCT No.: PCT/JP2019/008137
§ 371 (c)(1),
(2) Date: Aug. 27, 2020

(87) PCT Pub. No.: WO2019/168163
PCT Pub. Date: Sep. 6, 2019

(65) Prior Publication Data
US 2020/0407768 A1   Dec. 31, 2020

(30) Foreign Application Priority Data

Mar. 2, 2018   (JP) .................................. 2018-038036

(51) Int. Cl.
| C12Q 1/06 | (2006.01) |
| C07K 14/195 | (2006.01) |
| C12N 9/02 | (2006.01) |
| C12N 15/74 | (2006.01) |

(52) U.S. Cl.
CPC .............. C12Q 1/06 (2013.01); C07K 14/195 (2013.01); C12N 9/0004 (2013.01); C12N 15/74 (2013.01); C12Y 120/01001 (2013.01)

(58) Field of Classification Search
CPC .......... C12Q 1/32; C12Q 1/06; C07K 14/195; C12N 9/0004; C12N 15/74; C12N 1/12; C12N 15/52; C12N 15/8509; C12Y 120/01001
See application file for complete search history.

(56) References Cited

U.S. PATENT DOCUMENTS

| 11,130,981 B2 * | 9/2021 | Hirota .................... C12N 15/70 |
| 2014/0051134 A1 | 2/2014 | Kuroda et al. |
| 2015/0125934 A1 | 5/2015 | Kuroda et al. |

FOREIGN PATENT DOCUMENTS

| EP | 2860242 | 4/2015 |
| JP | 2013-31429 | 2/2013 |
| JP | 2015-128397 | 7/2015 |
| WO | WO 2013/003597 | 1/2013 |
| WO | 2014/024998 | 2/2014 |
| WO | WO 2016/073079 | 5/2016 |
| WO | 2018/042987 | 3/2018 |
| WO | WO-2018042987 A1 * | 3/2018 ............... C12N 1/20 |

OTHER PUBLICATIONS

Metcalf, W W, and R S Wolfe. "Molecular Genetic Analysis of Phosphite and Hypophosphite Oxidation by Pseudomonas Stutzeri WM88." Journal of bacteriology 180.21 (1998): 5547-5558. Web. (Year: 1998).*
Motomura, Kei et al. "Overproduction of YjbB Reduces the Level of Polyphosphate in *Escherichia coli*: a Hypothetical Role of YjbB in Phosphate Export and Polyphosphate Accumulation." FEMS microbiology letters 320.1 (2011): 25-32. Web. (Year: 2011).*
Sabri, Suriana et al. "Knock-in/Knock-Out (KIKO) Vectors for Rapid Integration of Large DNA Sequences, Including Whole Metabolic Pathways, onto the *Escherichia coli* Chromosome at Well-Characterised Loci." Microbial cell factories 12.1 (2013): 60-60. Web. (Year: 2013).*
Kang, Dong Gyun et al. "Versatile Signal Peptide of Flavobacterium-Originated Organophosphorus Hydrolase for Efficient Periplasmic Translocation of Heterologous Proteins in *Escherichia coli*." Biotechnology progress 32.4 (2016): 848-854. Web. (Year: 2016).*
Hirota, Ryuichi et al. "A Novel Biocontainment Strategy Makes Bacterial Growth and Survival Dependent on Phosphite." Scientific reports 7.1 (2017): 44748-44748. Web. (Year: 2017).*
Bisson, Claudine et al. "The Molecular Basis of Phosphite and Hypophosphite Recognition by ABC-Transporters." Nature communications 8.1 (2017): 1746-13. Web. (Year: 2017).*
Ferri, Stefano et al. "Efficient Surface-Display of Autotransporter Proteins in Cyanobacteria." Algal research (Amsterdam) 12 (2015): 337-340. Web. (Year: 2015).*
Geerts, Dirk et al. "Inducible Expression of Heterologous Genes Targeted to a Chromosomal Platform in the *Cyanobacterium synechococcus* Sp. PCC 7942." Microbiology (Society for General Microbiology) 141.4 (1995): 831-841. Web. (Year: 1995).*

(Continued)

*Primary Examiner* — Louise W Humphrey
*Assistant Examiner* — John Paul Selwanes
(74) *Attorney, Agent, or Firm* — Casimir Jones, S.C.; Robert A. Goetz

(57) ABSTRACT

It is an object of an aspect of the present invention to provide (i) transformants, whose proliferation depends on phosphite, of various species of organism and (ii) a method for detecting the presence of a reduced phosphorous compound with use of such a transformant. Use is made of a transformant which is defective in functions of a gene encoding a phosphate transporter protein and a gene encoding a phosphate ester transporter protein and into which a gene encoding a hypophosphite transporter protein is introduced, a signal peptide of a hypophosphite binding protein being substituted with a signal peptide derived from a host or a species of organism closely related to the host.

4 Claims, 7 Drawing Sheets

Specification includes a Sequence Listing.

(56) References Cited

OTHER PUBLICATIONS

Tessier DC, Thomas DY, Khouri HE, Laliberté F, Vernet T. Enhanced secretion from insect cells of a foreign protein fused to the honeybee melittin signal peptide. Gene. Feb. 15, 1991;98(2):177-83. doi: 10.1016/0378-1119(91)90171-7. PMID: 2016060. (Year: 1991).*
Low KO, Muhammad Mahadi N, Md Illias R. Optimisation of signal peptide for recombinant protein secretion in bacterial hosts. Appl Microbiol Biotechnol. May 2013;97(9):3811-26. doi: 10.1007/s00253-013-4831-z. Epub Mar. 26, 2013. PMID: 23529680. (Year: 2013 ).*
Search Report for EP Patent Application No. 19761315.1, mailed Mar. 25, 2021, 7 pages.
Kanbara Akihiro et al., "Development of a Selective Cultivation Method . . . ", Proceedings of the 69th Annual Meeting of the Society for Biotechnology, Japan, Aug. 8, 2017, pp. 138, 2P-H096.
White, A. K. et al., "The htx and ptx Operons of Pseudomonas stutzeri WM88 Are New Members of the Pho Regulon", Journal of Bacteriology, 2004, vol. 186, No. 17, pp. 5876-5882.
Hirota, Ryuichi et al., "Discovery of a Thermostable Phosphite . . . ", Journal of Environmental Biotechnology, 2014, vol. 14, No. 1, pp. 15-20.
Mackle, M. M. et al., "Role of signal peptides in targeting of proteins in cyanobacteria", Journal of Bacteriology, 1994, vol. 176, No. 7, pp. 1857-1864.
Vuppada, R. K. et al., "Phosphate signaling through alternate conformations of the PstSCAB phosphate transporter", BMC Microbiology, Jan. 19, 2018, 18: 8, (https:doi.org/10.1186/s12866-017-1126-z).
Hirota, Ryuichi et al., "Development of Biosafety System . . . ", Chemical engineering, vol. 63, No. 11, Nov. 1, 2018, pp. 799-805.
Sano, Kosuke et al., "An Engineered Phosphite Metabolic Pathway . . . ", Proceedings of the 70th Annual Meeting of the Society for Biotechnology, Japan, Aug. 7, 2018, pp. 111, 1Jp14.
Motomura, Kei et al., "A Novel Biological Containment System . . . ", Proceedings of Annual Meeting of the Japan Society for Bioscience, Biotechnology, and Agrochemistry, 2018, Published online on Mar. 5, 2018, 2A02a06.
Motomura, Kei et al., "Enzymatic Properties of Phosphite . . . ", Proceedings of the 70th Annual Meeting of the Society for Biotechnology, Japan, Aug. 7, 2018, pp. 112, 1Jp15.
Hirota, Ryuichi et al., "A Novel Biocontainment Strategy Makes Bacterial Growth and Survival Dependent on Phosphite", Scientific Reports, Mar. 20, 2017, pp. 1-10.
International Preliminary Report on Patentability for PCT/JP2019/008137, mailed Sep. 8, 2020, 6 pages.
International Search Report for PCT/JP2019/008137, mailed Jun. 4, 2019, 3 pages.
Non-Final Rejection, U.S. Appl. No. 16/328,560, dated Mar. 30, 2021.
Lecture Abstracts of Annual Meeting of The Society for Biotechnology, Japan, 2015, vol. 67, p. 319, P-194.
Office Action for JP Patent Application No. 2016-170317, mailed Jul. 28, 2020, 14 total pages.
EP Search Report, EP Patent Application No. 17845996.2, mailed Jul. 22, 2019, 12 pages.
Wright, O. et al: "Building-in biosafety for synthetic biology", Microbiology, vol. 159, No. Pt, 7, Mar. 21, 2013 (Mar. 21, 2013), pp. 1221-1235, XP05515545.
Motomura, Kei "Synthetic Phosphorus Metabolic Pathway for Biosafety . . . " ACS Synthetic Biology, vol. 7 No. 9, Sep. 11, 2018 pp. 2189-2198 XP055604047.
Ryuichi Hirota, Microorganism's metabolism of reduced phosphorus compound . . . , Proceedings of the 11th Annual Meeting of the Society of Genome Microbiology, Japan, 2017, vol. 11, p. 52.
Ryuichi Hirota and Akio Kuroda, Kagaku Kogyo, Selective and Biologically Contained Cultivation System for Microorganism Using Phosphite, vol. 68, Jun. 1, 2017 (Jun. 1, 2017), pp. 429-435, Section 3.
Zen-ichiro Katsuura et al., Characterization of a biologically contained Escherichia . . . , Proceedings of the Annual Meeting of the Japan Society for Bioscience, Biotechnology, and Agrochemistry, 2017, 4J30a05.
Ryuichi Hirota et al, A Novel biocontainment strategy makes bacterial growth dependent on phosphite, Proceedings of the Annual Meeting of the Japan Society for Bioscience, Biotechnology, and Agrochemistry, 2017, 6 pages.
Atsushi Sakuda et al, Development of a feasible phosphite detection system . . . , Proceedings of the Annual Meeting of the Japan Society for Bioscience, Biotechnology, and Agrochemistry, 2014.
Ryuichi Hirota and Akio Kuroda, Biotechnology using reduced phosphorous compound, Enzyme Engineering News, vol. 74, Oct. 2015, pp. 26-31.
Mandell DJ et al., Biocontainment of genetically modified organisms by synthetic protein design, 2015, vol. 518, pp. 55-60, Abstract.
Rovner AJ et al., Recoded organisms engineered to depend on synthetic amino acids, 2015, vol. 518, pp. 89-93, Abstract.
Lauwers AM et al., Alterations of Alkaline Phosphatase Activity during Adaptation of *Escherichia coli* to Phosphite and Hypophosphite, 1977, vol. 112, pp. 103-107, Abstract.
Kanda K et al., Application of a phosphite dehydrogenase gene as a novel . . . , 2014, vol. 182-183, pp. 68-73, Abstract.
Loera-Quezada MM et al., A novel genetic engineering platform for the effective management of biological . . . , May 28, 2016, vol. 14, pp. 2066-2076, Summary.
Metcalf WW et al.., Molecular Genetic Analysis of Phosphite and Hypophosphite . . . , 1998, vol. 180, pp. 5547-5558, Abstract.
Wilson MM et al.., Genetic Diversity and Horizontal Transfer of Genes Involved in Oxidation . . . , 2005, vol. 71, pp. 290-296, Abstract.
English translation of International preliminary report on patentability of PCT/JP2017/027588, mailed Mar. 14, 2019, 8 pages.
International Search Report for PCT/JP2017/027588, mailed Oct. 24, 2017, 3 pages.

\* cited by examiner

TRANSFORMANT, AND METHOD USING SAID TRANSFORMANT TO DETECT PRESENCE OR ABSENCE OF REDUCED PHOSPHOROUS COMPOUND

TECHNICAL FIELD

The present invention relates to a transformant and a method for detecting the presence of a reduced phosphorous compound with use of the transformant.

BACKGROUND ART

Recently, genetically modified organisms applicable to various uses have been prepared. The genetically modified organisms thus prepared are expected to be used for the purpose of, for example, oral vaccines or improvement of natural environment.

Meanwhile, there are several demands which should be satisfied when genetically modified organisms are actually used. As one of the demands, it is necessary to prepare a genetically modified organism which can proliferate only in a limited place but cannot proliferate outside the limited place (in other words, a genetically modified organism by which a high containment effect is obtained). In the case of such a genetically modified organism, the genetically modified organism cannot proliferate in nature even if the genetically modified organism leaks into nature. Therefore, it is possible to prevent contamination of nature by the genetically modified organism.

Various methods for preparing such a genetically modified organism have been developed. One of the methods is a method in which an organism is made to be auxotrophic for a compound that does not naturally occur (synthetic auxotrophy). Non-Patent Literature 1 is a specific example which discloses the method. Non-Patent Literature 1 discloses that the inventors of the present application modified the metabolism of *Escherichia coli* (*E. coli*) such that the growth of the *E. coli* depends on phosphite, whose presence is rare in the environment, and the inventors thus successfully prepared an *E. coli* transformant by which the highest level of containment effect known is obtained.

CITATION LIST

Non-Patent Literature

[Non-Patent Literature 1]
Ryuichi Hirota et. al., A Novel Biocontainment Strategy Makes Bacterial Growth and Survival Dependent on Phosphite, Scientific RepoRts, 20 Mar. 2017

SUMMARY OF INVENTION

Technical Problem

The transformant developed by the inventors of the present application enables obtaining a high containment effect and reducing cost for proliferation of the transformant, in contrast to a conventional transformant that has been made to be auxotrophic. As such, development of transformants, whose proliferation depends on phosphite, of various host organisms not confined to *E. coli* is expected, as well as development of means for reliably selecting an appropriate place (i.e., a place where no phosphite compound is included) in nature and culturing the transformant only in that place.

It is an object of an aspect of the present invention to provide (i) transformants, whose proliferation depends on phosphite, of various species of organism and (ii) a method for detecting the presence of a reduced phosphorous compound with use of such a transformant.

Solution to Problem

The inventors of the present application tried to apply the technique of preparing the *E. coli* transformant to other hosts, but could not obtain a desired transformant with use of the other hosts. As a result of diligent study, the inventors of the present application found that localization of a particular protein to be expressed in a host is involved in whether or not a desired transformant is successfully prepared. Based on this finding, the inventors of the present application made the present invention.

In order to attain the object, a transformant in accordance with an aspect of the present invention is a transformant which is defective in functions of a gene encoding a phosphate transporter protein and a gene encoding a phosphate ester transporter protein and into which a gene encoding a hypophosphite transporter protein is introduced, the transformant being incapable of utilizing phosphate for proliferation but capable of utilizing phosphite for proliferation, the hypophosphite transporter protein including a hypophosphite binding protein as a constituent element, a signal peptide of the hypophosphite binding protein being substituted with a signal peptide derived from a host or a species of organism closely related to the host.

In order to attain the object, a method for detecting the presence of a reduced phosphorous compound in accordance with an aspect of the present invention is a method for detecting the presence of a reduced phosphorous compound in a culture medium which is a detection target, the method including the steps of: culturing a transformant in accordance with an aspect of the present invention, with use of a culture medium as a detection target; and detecting whether or not the transformant proliferated in the step of culturing.

Advantageous Effects of Invention

In a transformant in accordance with an aspect of the present invention, a signal peptide of a hypophosphite transporter protein, which is a constituent element of a hypophosphite transporter protein, is substituted with a signal peptide derived from a host or a species of organism closely related to the host. This enables a function of the hypophosphite transporter protein to be reliably expressed in the host. Accordingly, it is possible to provide transformants, whose proliferation depends on phosphite and by which a high containment effect is obtained, of various species of organism.

A transformant in accordance with an aspect of the present invention makes it possible to reduce cost for proliferation of the transformant, since the transformant is cultured by use of an inexpensive reduced phosphorous compound.

A transformant in accordance with an aspect of the present invention makes it possible to reduce cost for proliferation of the transformant, since the transformant is cultured without use of an expensive antibiotic substance.

A method for detecting the presence of a reduced phosphorous compound in accordance with an aspect of the present invention makes it possible to provide a method for detecting the presence of a reduced phosphorous compound which method uses a transformant whose proliferation depends on an inexpensive reduced phosphorous compound, and thus enables eliminating the need for a complicated step and reducing cost for proliferation of the transformant.

Figure 5:
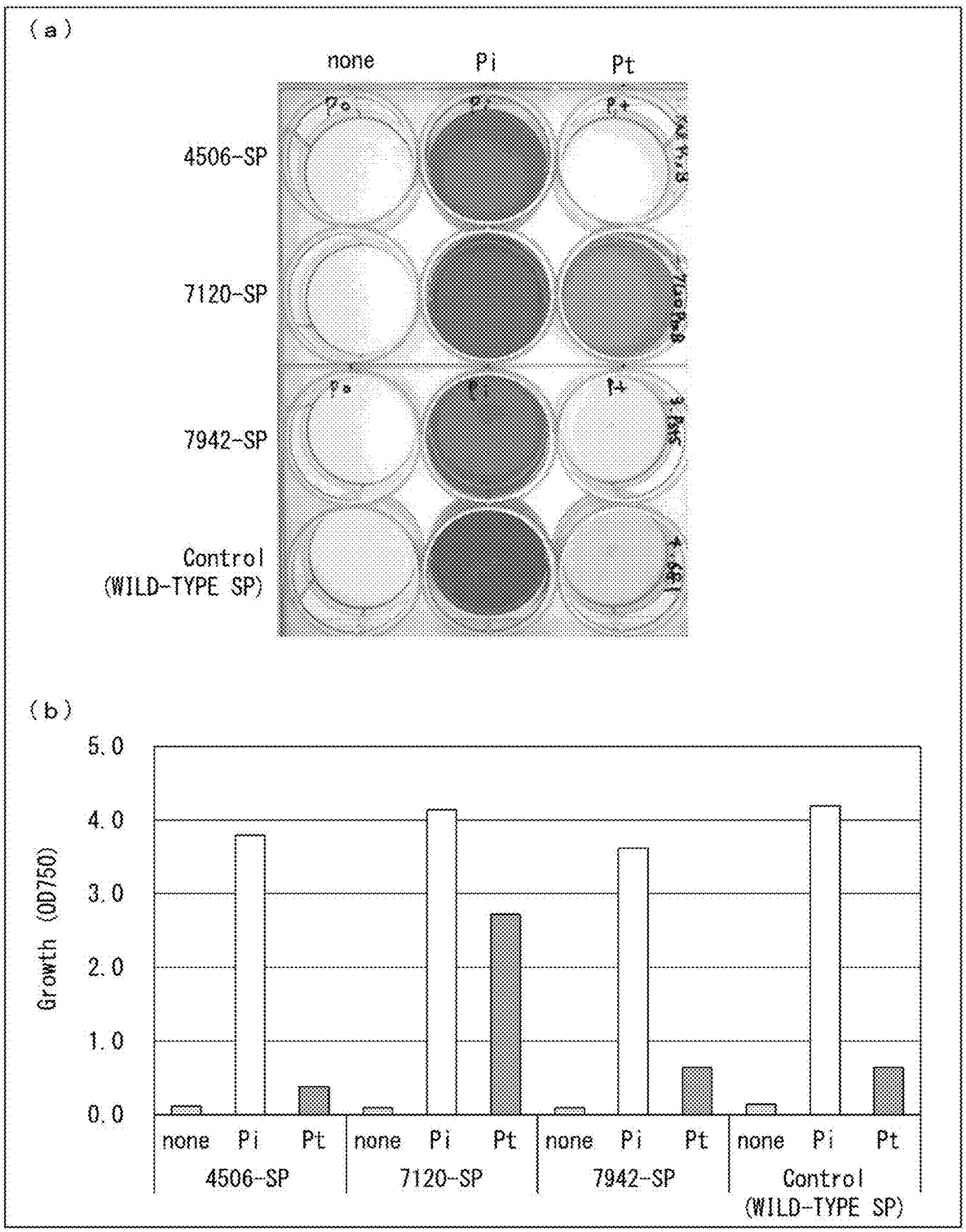

(a) of FIG. 5 shows images of results of phosphate-dependent proliferation and phosphite-dependent proliferation. (b) of FIG. 5 shows graphs indicative of results of phosphate-dependent proliferation and phosphite-dependent proliferation.

Figure 6:
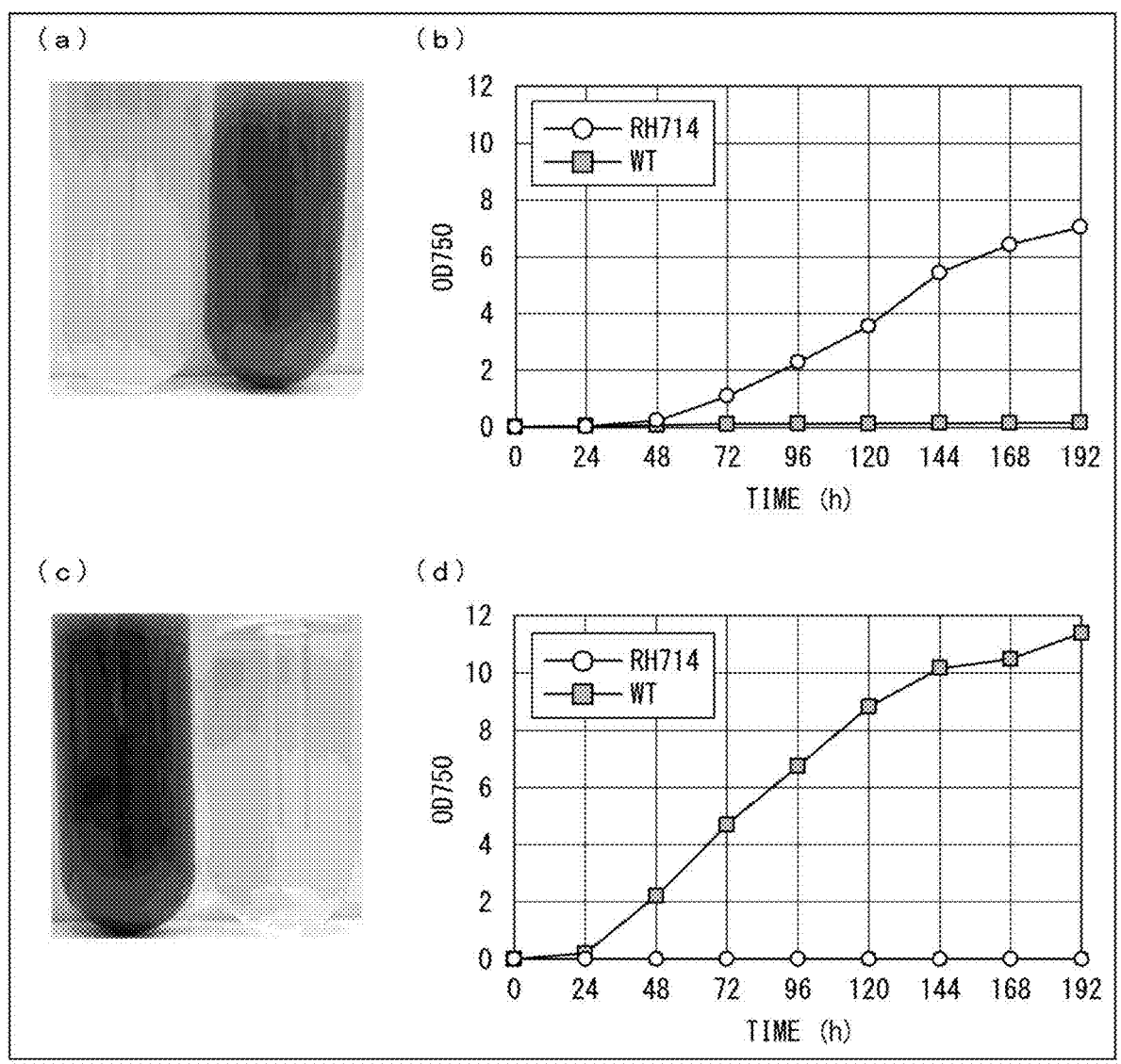

(a) and (c) of FIG. 6 each show images of states of proliferation of a disrupted strain RH714 and a wild strain after 192 hours. (b) and (d) of FIG. 6 each show a graph indicative of changes over time of proliferation of the disrupted strain RH714 and the wild strain.

Figure 7:
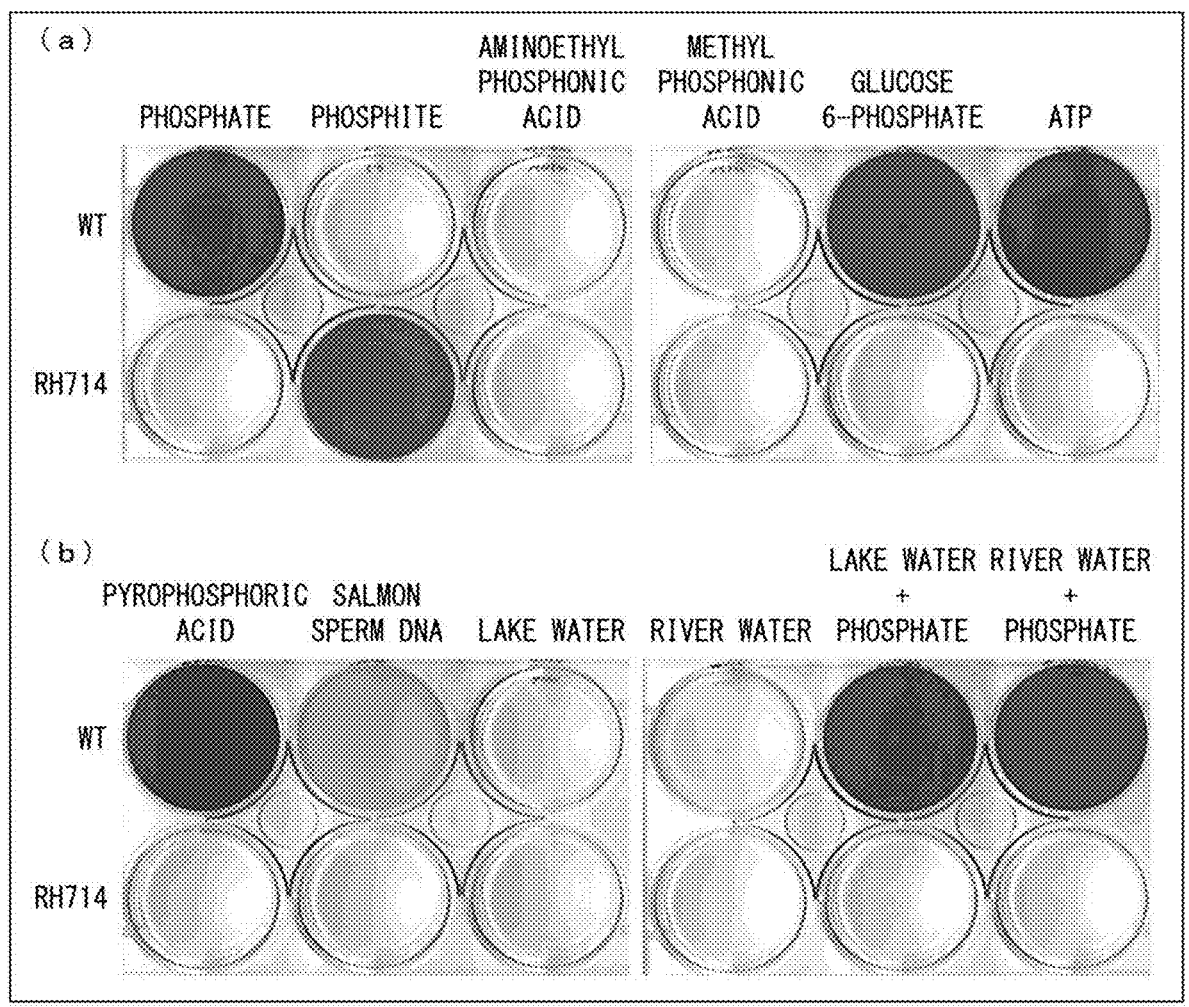

FIG. 7 shows images of states of proliferation of the disrupted strain RH714 cultured in culture mediums containing respective phosphorus compounds as a phosphorus source.

Figure 8:
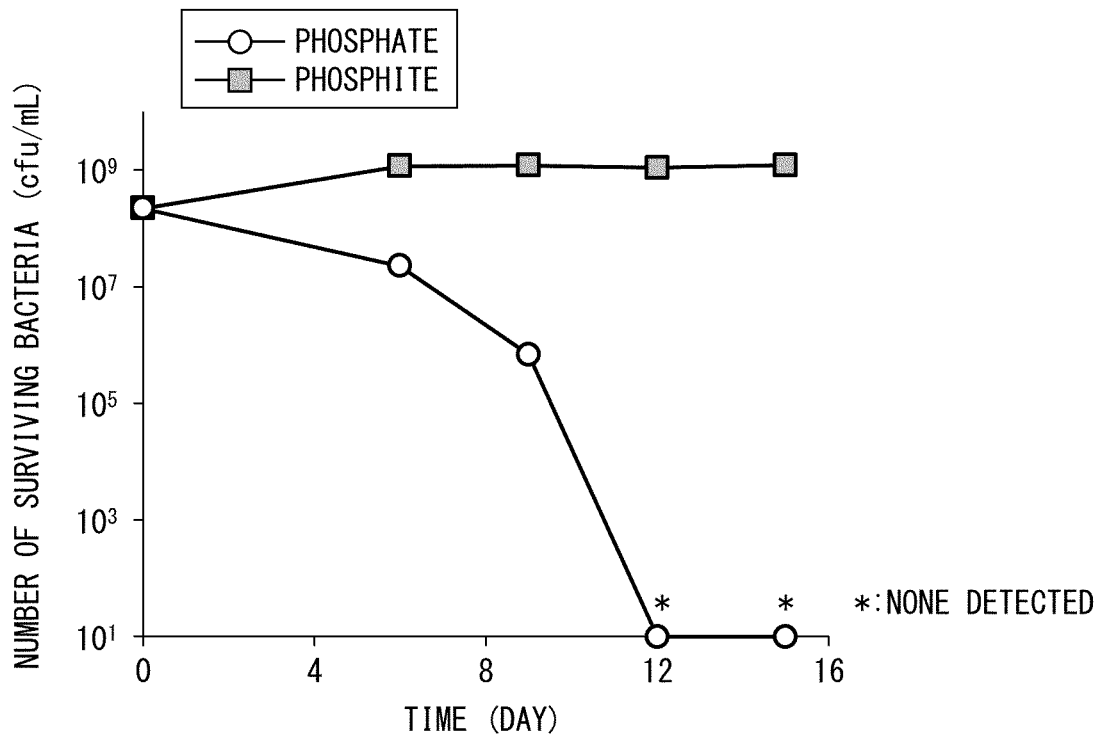

FIG. 8 shows a graph indicative of changes over time of the number of surviving bacteria of the disrupted strain RH714.

Figure 9:
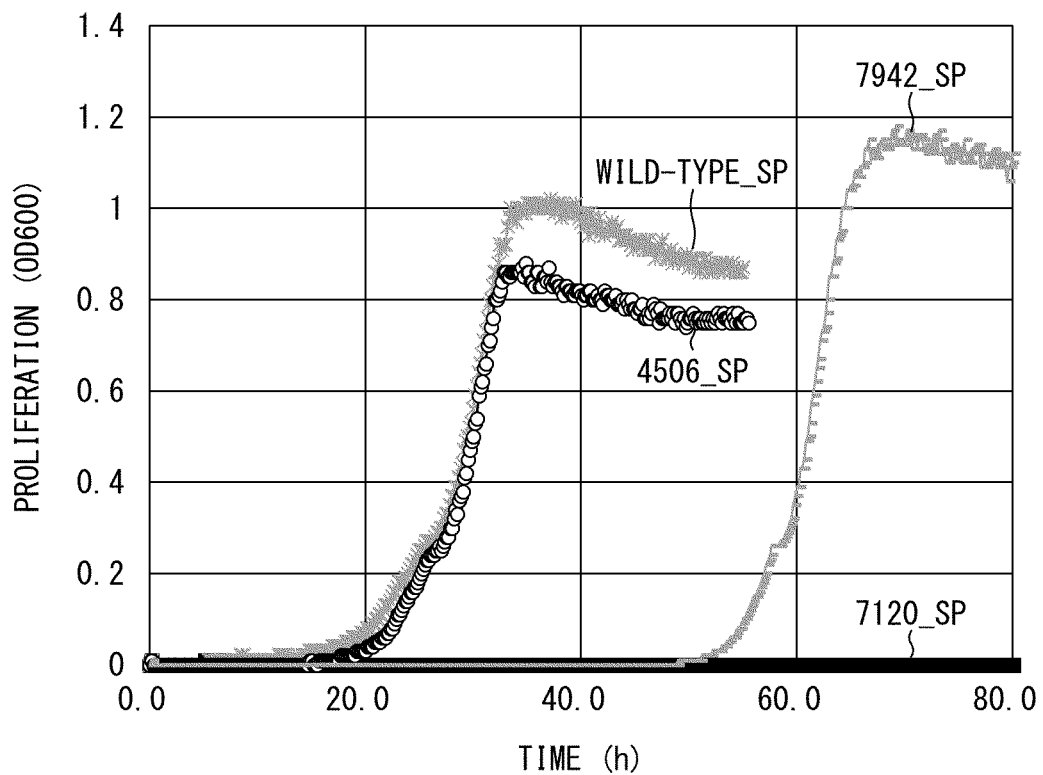

FIG. 9 shows a graph indicative of results of phosphite-dependent proliferation.

DESCRIPTION OF EMBODIMENTS

An embodiment of the present invention will be discussed below. Note, however, that the present invention is not limited to such an embodiment. The present invention is not limited to arrangements described below, but can be altered within the scope of the claims. Any embodiment and example derived from a combination of technical means disclosed in different embodiments and/or examples is also encompassed in the technical scope of the present invention. All literatures listed herein are incorporated herein by reference. Note that a numerical range "A to B" herein means "not less than A and not more than B".

[1. Basic Principle of Aspect of the Present Invention]

In nature, whereas a large amount of phosphate (or phosphate compound) exists, a reduced phosphorous compound (e.g., phosphite and hypophosphite) is absent or if any, only a very small amount of reduced phosphorous compound is present. In this condition, in a case where a transformant, whose proliferation does not depend on phosphate but depends on a reduced phosphorous compound, is prepared, the transformant cannot proliferate in nature even if the transformant leaks into nature. The inventors of the present application focused on this point and prepared a transformant whose proliferation does not depend on phosphate but depends on a reduced phosphorous compound. As a result, the inventors of the present application successfully provided a transformant by which a high containment effect is obtained.

Figure 1:
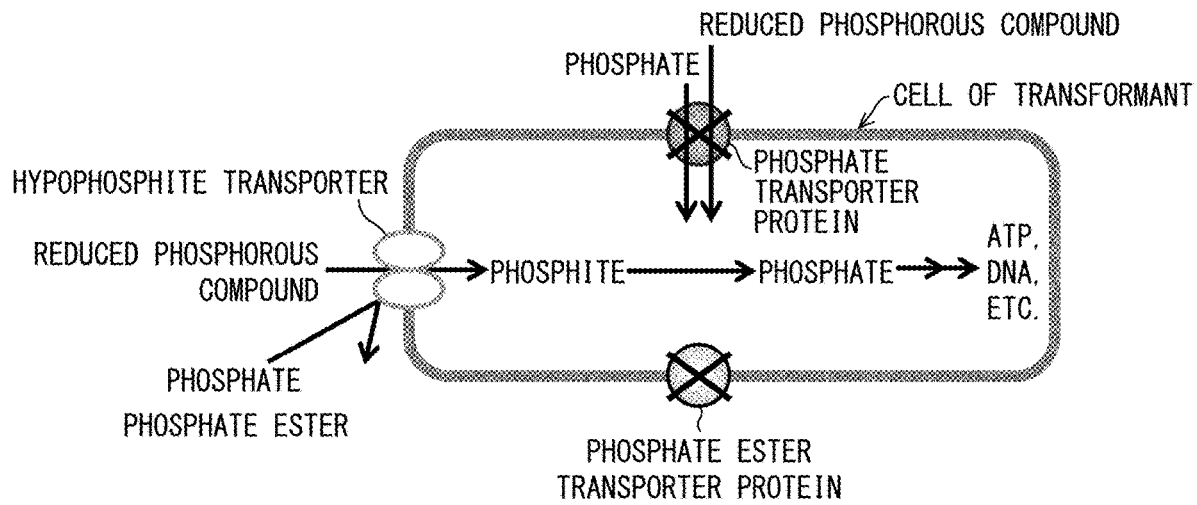
FIG. 1 is a diagram illustrating a structure of a transformant of an aspect of the present invention.

The transformant will be described below with reference to FIG. 1. FIG. 1 is a diagram illustrating a structure of a transformant of an aspect of the present invention. As illustrated in FIG. 1, a phosphate transporter protein and a phosphate ester transporter protein are basically present in organisms.

The phosphate transporter protein is a protein for uptake of phosphate and a reduced phosphorous compound into cells. On the other hand, the phosphate ester transporter protein is a protein for uptake of phosphate ester into cells. Note that when phosphate ester is taken into cells, the phosphate ester is indirectly utilized as a phosphorus source (P source) in a metabolic system of the cells.

When phosphate is supplied from nature to cells, a transformant proliferates in nature dependently on the phosphate. To prevent this, the inventors of the present application first caused functions of both of the phosphate transporter protein and the phosphate ester transporter protein to be defective in the transformant. As a result, the inventors successfully prevented supply of phosphate from nature to cells of the transformant.

However, when the functions of both the phosphate transporter protein and the phosphate ester transporter protein were caused to be defective, neither phosphate nor a reduced phosphorous compound were supplied any longer from nature to cells. In this case, the transformant cannot proliferate dependently on the reduced phosphorous compound.

The inventors of the present application found that a hypophosphite transporter protein encoded by HtxBCDE gene (or HtxBCD gene) derived from *Pseudomonas stutzeri* WM88 has a function to transport a reduced phosphorous compound but no phosphate. Based on the finding, the inventors solved the above problem.

That is, the inventors of the present application prepared a transformant capable of utilizing only a reduced phosphorous compound, by causing a function of a phosphate transport system of a host to be defective and introducing HtxBCDE gene (or HtxBCD gene) into the host. If the transformant expresses HtxBCDE protein (or HtxBCD protein), the transformant can take only a reduced phosphorous compound into cells. The reduced phosphorous compound is converted to phosphate in a metabolic system of cells. Then, the transformant can proliferate by utilizing the phosphate.

The above-described transformant invented by the inventors of the present application is prepared without the need of a complicated step and enables reducing cost for proliferation of the transformant, in contrast to a conventional transformant (specifically, an *E. coli* transformant) that has been made to be auxotrophic. Further, a high containment effect is obtained by the transformant. As such, development of transformants, whose proliferation depends on a reduced phosphorous compound, of various host organisms including *E. coli* was expected.

Examples of organisms, other than *E. coli*, with respect to which the preparation of the transformants is expected include microalgae, which is a typical example of prokaryote. Microalgae proliferate faster than plants and are capable of synthesizing various useful substances while fixing carbon dioxide. Further, microalgae are capable of producing substances having low environmental impact. For the above reasons, microalgae are expected to be utilized as a host. Further, with the advancement of genetic modification technology, modified microalgae having various useful characters are expected to be developed and commercially used.

However, it is difficult to obtain permission for using modified organisms in outdoor culture, in which physical containment is difficult to achieve. It is thus difficult to practice outdoor culture of the modified organisms. Accordingly, with respect to various organisms, provision of transformants by which a high biological containment effect is obtained was expected.

Then, the inventors of the present application tried to prepare a transformant with use of cyanobacteria, which is a typical example of prokaryote, as a host. Specifically, the inventors of the present application tried to prepare the transformant by subjecting cyanobacteria to the following three steps: (i) causing functions of a phosphate transporter protein and a phosphate ester transporter protein to be defective, (ii) introducing a phosphite dehydrogenase protein which converts phosphite into phosphate, and (iii) expressing HtxBCDE protein (or HtxBCD protein). However, the function of HtxBCDE protein (or HtxBCD protein) was not expressed in the cyanobacteria.

Figure 2:
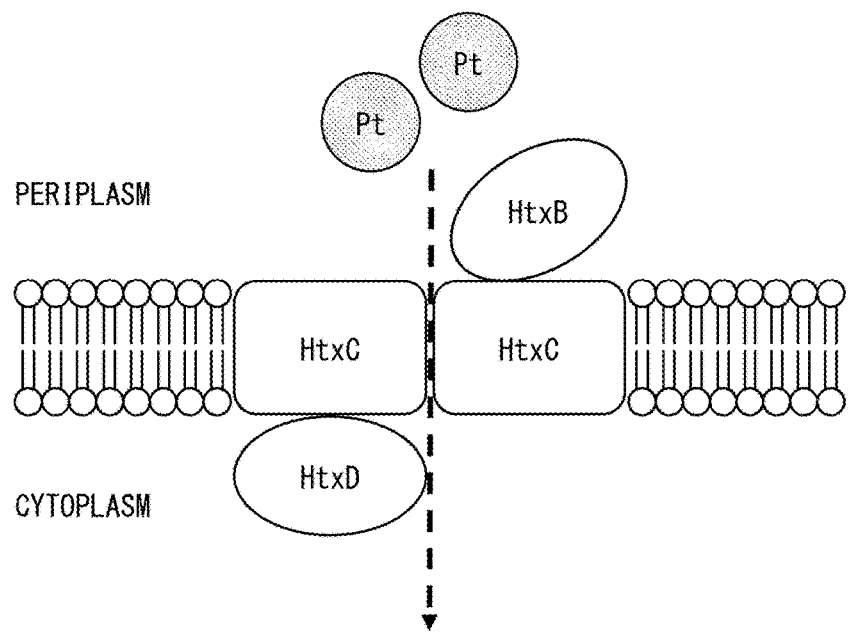
FIG. 2 is a diagram illustrating a structure of HtxBCD protein bound to a membrane.

The following description will discuss details of HtxBCDE protein and HtxBCD protein with reference to FIG. 2. FIG. 2 is a diagram of a structure of each of HtxBCDE protein and HtxBCD protein bound to a membrane, the structure being schematically illustrated for convenience of explanation. The HtxBCDE protein and the HtxBCD protein are each a membrane-bound protein complex which is composed of HtxB protein, HtxC protein, and HtxD protein, and optionally further includes HtxE protein (not illustrated).

HtxB is a protein which is localized in periplasm on an outer side of a cell membrane. HtxC is a protein which is bound to a cell membrane. HtxD is a protein which is present in cytoplasm and has an ATPase activity. As illustrated in FIG. 2, HtxB among these proteins is bound to phosphite (Pt in FIG. 2) in a substrate.

The inventors of the present application predicted, among many possible explanations for the cause of failure, that when HtxBCDE gene was introduced into cyanobacteria, HtxB protein could not be localized in an appropriate place (specifically, periplasm) (see a portion on the left of a broken line arrow in FIG. 2), and this prevented functions of HtxBCDE protein and HtxBCD protein from being expressed. Note that a portion on the right of the broken line arrow in FIG. 2 represents localization of HtxB when functions of HtxBCDE protein and HtxBCD protein are expressed.

Then, the inventors of the present application formed and tested a hypothesis that substituting a sequence of a signal peptide in a sequence of HtxB protein with a sequence of a signal peptide derived from a host and causing the HtxBCDE protein containing the HtxB protein in which the substitution has been made to be expressed in cyanobacteria would allow the HtxB protein to be localized appropriately in periplasm of the cyanobacteria.

The inventors of the present application carried out the above-described steps (i) and (ii) and also the following step as the above-described step (iii). That is, the inventors substituted a sequence of a signal peptide of HtxB protein in a sequence of HtxBCDE protein with a signal peptide of a periplasmic protein derived from microalgae. Specifically, a signal peptide sequence of periplasmic protein PtxB included in *Anabaena* (*Anabaena* sp. PCC7120), which is a type of cyanobacteria, was substituted with a sequence of a signal peptide of HtxB protein. Then, a gene encoding the HtxBCDE protein containing the HtxB protein after the substitution was introduced into cyanobacteria. As a result, a transformant of cyanobacteria was obtained, and it was confirmed that the transformant proliferated independently of phosphate and dependently of phosphite. It was also verified that a high containment effect was obtained by the transformant.

The following will discuss an embodiment of the present invention in more details.

[2. Transformant in Accordance with Embodiment of the Present Invention]

A transformant in accordance with the present embodiment of the present invention is a transformant which is defective in functions of a gene encoding a phosphate transporter protein and a gene encoding a phosphate ester transporter protein and into which a gene encoding a hypophosphite transporter protein is introduced, the transformant being incapable of utilizing phosphate for proliferation but capable of utilizing phosphite for proliferation, the hypophosphite transporter protein including a hypophosphite binding protein as a constituent element, a signal peptide of the hypophosphite binding protein being substituted with a signal peptide derived from a host or a species of organism closely related to the host.

Specifically, a "species of organism closely related to a host" means, for example, an organism belonging to the same genus as a host.

Examples of a host of the transformant in accordance with the present embodiment encompass prokaryotes (specifically, *E. coli*, microalgae, and the like), eukaryotes (yeast and the like). The host is of course not limited to these examples. A transformant in accordance with an embodiment of the present invention can be prepared by manipulation of a small number of genes. Therefore, any organism (e.g., microorganism) can be the host.

Examples of the *E. coli* used as the host encompass K-12 strain, BL21 strain, and the like.

Examples of the microalgae encompass cyanobacteria, *Euglena*, diatoms, *Botryococcus*, and the like.

Examples of the cyanobacteria used as the host encompass *Anabaena* sp. PCC7120, *Synechocystis* sp., *Synechococcus* sp., and the like.

The term "phosphate transporter protein" herein means a protein which has activity to take both phosphate and a reduced phosphorous compound into cells. On the other hand, the term "phosphate ester transporter protein" herein means a protein which has activity to take phosphate ester into cells.

In this case, the transformant, which is defective in the functions of the gene encoding a phosphate transporter protein and the gene encoding a phosphate ester transporter protein, can be prepared by artificially mutating a host. Alternatively, the transformant may be prepared by using a host which originally has neither of the functions of the gene encoding a phosphate transporter protein and the gene encoding a phosphate ester transporter protein (e.g., a host having a genome in which both the gene encoding a phosphate transporter protein and the gene encoding a phosphate ester transporter protein are absent, or a host which expresses neither a phosphate transporter protein nor a phosphate ester transporter protein).

Different types of phosphate transporter protein and different types of phosphate ester transporter protein exist in cells of different species of organism. Therefore, there is no limitation to particular types of phosphate transporter protein and phosphate ester transporter protein which have functions defective in the transformant in accordance with the present embodiment. It is possible to determine as appropriate, depending on a host, the gene encoding a phosphate transporter protein and the gene encoding a phosphate ester transporter protein, which genes have functions that are caused to be defective in the host.

For example, in a case where a host of the transformant is cyanobacteria (*Synechococcus elongatus* PCC7942, hereinafter referred to as "7942 strain"), examples of a phosphate transporter protein whose function is to be made defective encompass pit, sphX-pstSCAB, and the like. Note here that genome data (cyanobase: genome.microbedb.jp/cyanobase/) of PCC 7942 strain published in Kazusa Genome Resource suggests that the pit protein and the sphX-pstSCAB protein are phosphate transporter proteins present in PCC 7942 strain.

More specifically, the Pit protein is (1) a protein consisting of an amino acid sequence of SEQ ID NO: 2, (2) a protein (i) consisting of an amino acid sequence obtained by deletion, substitution, or addition of one or several amino acids in the amino acid sequence of SEQ ID NO: 2 and (ii) functioning as a phosphate transporter, (3) a protein encoded by a gene consisting of a polynucleotide consisting of a base sequence of SEQ ID NO: 1, or (4) a protein encoded by a gene consisting of a polynucleotide (i) being hybridizable, under a stringent condition, with DNA consisting of a base sequence complementary to the base sequence of SEQ ID NO: 1 and (ii) encoding a protein which has phosphate transport activity.

The sphX-pstSCAB protein is composed of sphX, pstS, pstC, pstA, and pstB proteins.

Specifically, the sphX protein may be (5) a protein consisting of an amino acid sequence of SEQ ID NO: 16 or (6) a protein (i) consisting of an amino acid sequence obtained by deletion, substitution, or addition of one or several amino acids in the amino acid sequence of SEQ ID NO: 16 and (ii) functioning as a phosphate transporter together with the pstS, pstC, pstA, and pstB proteins; the pstS protein may be (7) a protein consisting of an amino acid sequence of SEQ ID NO: 34 or (8) a protein (i) consisting of an amino acid sequence obtained by deletion, substitution, or addition of one or several amino acids in the amino acid sequence of SEQ ID NO: 34 and (ii) functioning as a phosphate transporter together with the sphX, pstC, pstA, and pstB proteins; the pstC protein may be (9) a protein consisting of an amino acid sequence of SEQ ID NO: 37 or (10) a protein (i) consisting of an amino acid sequence obtained by deletion, substitution, or addition of one or several amino acids in the amino acid sequence of SEQ ID NO: 37 and (ii) functioning as a phosphate transporter together with the sphX, pstS, pstA, and pstB proteins; the pstA protein may be (11) a protein consisting of an amino acid sequence of SEQ ID NO: 39 or (12) a protein (i) consisting of an amino acid sequence obtained by deletion, substitution, or addition of one or several amino acids in the amino acid sequence of SEQ ID NO: 39 and (ii) functioning as a phosphate transporter together with the sphX, pstS, pstC, and pstB proteins; and the pstB protein may be (13) a protein consisting of an amino acid sequence of SEQ ID NO: 41 or (14) a protein (i) consisting of an amino acid sequence obtained by deletion, substitution, or addition of one or several amino acids in the amino acid sequence of SEQ ID NO: 41 and (ii) functioning as a phosphate transporter together with the sphX, pstS, pstA, and pstC proteins.

The above sphX-pstSCAB gene is composed of polynucleotides respectively encoding the sphX, pstS, pstA, pstC, and pstB proteins constituting the phosphate transporter. That is, the sphX-pstSCAB protein may be a protein encoded by the sphX-pstSCAB gene.

Specifically, the polynucleotide encoding the sphX protein may be (15) a nucleotide consisting of a base sequence of SEQ ID NO: 15 or (16) a nucleotide (i) being hybridizable, under a stringent condition, with a base sequence complementary to the polynucleotide consisting of the base sequence of SEQ ID NO: 15 and (ii) encoding a protein functioning as a phosphate transporter together with the pstS, pstC, pstA, and pstB proteins; the polynucleotide encoding the pstS protein may be (17) a nucleotide consisting of a base sequence of SEQ ID NO: 33 or (18) a nucleotide (i) being hybridizable, under a stringent condition, with a base sequence complementary to the polynucleotide consisting of the base sequence of SEQ ID NO: 33 and (ii) encoding a protein functioning as a phosphate transporter together with the sphX, pstC, pstA, and pstB proteins; the polynucleotide encoding the pstC protein may be (19) a nucleotide consisting of a base sequence of SEQ ID NO: 38 or (20) a nucleotide (i) being hybridizable, under a stringent condition, with a base sequence complementary to the polynucleotide consisting of the base sequence of SEQ ID NO: 38 and (ii) encoding a protein functioning as a phosphate transporter together with the sphX, pstS, pstA, and pstB proteins; the polynucleotide encoding the pstA protein may be (21) a nucleotide consisting of a base sequence of SEQ ID NO: 40 or (22) a nucleotide (i) being hybridizable, under a stringent condition, with a base sequence complementary to the polynucleotide consisting of the base sequence of SEQ ID NO: 40 and (ii) encoding a protein functioning as a phosphate transporter together with the sphX, pstS, pstC, and pstB proteins; and the polynucleotide encoding the pstB protein may be (23) a nucleotide consisting of a base sequence of SEQ ID NO: 42 or (24) a nucleotide (i) being hybridizable, under a stringent condition, with a base sequence complementary to the polynucleotide consisting of the base sequence of SEQ ID NO: 42 and (ii) encoding a protein functioning as a phosphate transporter together with the sphX, pstS, pstA, and pstC proteins.

Whether a protein has phosphate transport activity can be checked by (i) introducing a gene encoding a chosen protein in an expressible manner into an organism that is defective in the functions of the gene encoding a phosphate transporter protein and the gene encoding a phosphate ester transporter protein and (ii) causing the organism to proliferate in culture media containing various phosphorus sources. If the organism proliferates in a culture medium containing phosphate, it can be determined that the above protein has phosphate transport activity.

Further, whether a protein has phosphate ester transport activity can be checked by (i) introducing a gene encoding a chosen protein in an expressible manner into an organism that is defective in the functions of the gene encoding a phosphate transporter protein and the gene encoding a phosphate ester transporter protein and (ii) causing the organism to proliferate in culture media containing various phosphorus sources. If the organism proliferates in a culture medium containing phosphate ester, it can be determined that the above protein has phosphate ester transport activity.

Further, in a case where the host of the transformant is *E. coli*, for example, a transformant that is defective in a function of a gene encoding a phosphate transporter protein can be used. It is known that in *E. coli*, there are four phosphate transporter proteins including PitA, PitB, PstS-CAB, and PhnCDE. As a strain in which genes encoding the above-described four phosphate transporter proteins and a gene encoding phoA protein are disrupted, MT2012 strain (ΔpitA, ΔpitB, ΔphnC, ΔpstSCABphoU, ΔphoA) has been previously prepared (Motomura, K. et al. Overproduction of YjbB reduces the level of polyphosphate in *Escherichia coli*: a hypothetical role of YjbB in phosphate export and polyphosphate accumulation. FEMS microbiology letters 320, 25-32, 2011).

The term "hypophosphite transporter protein" herein means a protein which has activity to take phosphite or hypophosphite into cells. Examples of the hypophosphite transporter protein encompass HtxBCDE protein, HtxBCD protein, and the like. Note that the gene encoding the HtxBCDE protein and the gene encoding the HtxBCD protein may be each a gene derived from *Pseudomonas stutzeri* WM88.

The HtxBCDE protein is a protein complex composed of HtxB, HtxC, HtxD, and HtxE.

In a transformant in accordance with an embodiment of the present invention, the hypophosphite transporter protein includes a hypophosphite binding protein as a constituent element, a signal peptide of the hypophosphite binding protein being substituted with a signal peptide derived from a host or a species of organism closely related to the host. With this arrangement, it is possible to cause a hypophosphite binding protein to be localized in an appropriate place in a host.

The term "hypophosphite binding protein" herein means a protein which has binding capacity with respect to a substrate (specifically, phosphate or phosphite).

As a sequence of the "signal peptide derived from a host or a species of organism closely related to the host", it is possible to employ a sequence of a signal peptide of a periplasmic protein (e.g., ptxB protein) of *Anabaena* (*Anabaena* sp. PCC7120, hereinafter referred to as "7120 strain"), which is a type of cyanobacteria, in a case where, for example, (i) the host is cyanobacteria (7942 strain) and (ii) the hypophosphite transporter protein is HtxBCDE protein or HtxBCD protein. By substituting an original signal peptide of HtxB protein with the above signal peptide, it is possible to obtain a transformant in accordance with an embodiment of the present invention.

Further, the host may be various prokaryotes not confined to cyanobacteria. For example, in a case where the host is *E. coli* (e.g., K-12 strain, BL21 strain, or the like) and the hypophosphite transporter protein is HtxBCDE, it is possible to employ a signal peptide of a periplasmic protein (e.g., PtxB protein or the like) of *Ralstonia* (*Ralstonia* sp. 4506, hereinafter referred to as "4506 strain"), which is a species closely related to gram-negative soil bacteria. By substituting an original signal peptide of HtxB protein with the above signal peptide, it is possible to obtain a transformant in accordance with an embodiment of the present invention.

Specifically, the hypophosphite transporter protein in accordance with the present embodiment may be composed of HtxB protein (in which a signal peptide has been substituted), HtxC protein, and HtxD protein, and may optionally further include HtxE protein which serves as a cell membrane-bound protein.

Specifically, a sequence of a signal peptide of a periplasmic protein PtxB derived from *Anabaena* may be (25) a protein consisting of an amino acid sequence of SEQ ID NO: 54 or (26) a protein (i) consisting of an amino acid sequence obtained by deletion, substitution, or addition of one or several amino acids in the amino acid sequence of SEQ ID NO: 54 and (ii) having activity as a signal peptide of a periplasmic protein.

Further, a nucleotide encoding a signal peptide of a periplasmic protein PtxB derived from *Anabaena* may be (27) a polynucleotide consisting of a base sequence of SEQ ID NO: 55 or (28) a nucleotide (i) being hybridizable, under a stringent condition, with a base sequence complementary to the polynucleotide consisting of the base sequence of SEQ ID NO: 55 and (ii) encoding a protein having activity as a signal peptide of a periplasmic protein.

The above-described HtxB protein in which the sequence of a signal peptide has been substituted with the sequence of the signal peptide of the periplasmic protein PtxB derived from *Anabaena* may be, for example, (29) a protein consisting of an amino acid sequence of SEQ ID NO: 6 or (30) a protein (i) consisting of an amino acid sequence obtained by deletion, substitution, or addition of one or several amino acids in the amino acid sequence of SEQ ID NO: 6 and (ii) functioning as a hypophosphite transporter together with the HtxC protein and the HtxD protein or with the HtxC protein, the HtxD protein, and the HtxE protein; the HtxC protein may be (31) a protein consisting of an amino acid sequence of SEQ ID NO: 8 or (32) a protein (i) consisting of an amino acid sequence obtained by deletion, substitution, or addition of one or several amino acids in the amino acid sequence of SEQ ID NO: 8 and (ii) functioning as a hypophosphite transporter together with the HtxB protein and the HtxD protein or with the HtxB protein, the HtxD protein, and the HtxE protein; the HtxD protein may be (33) a protein consisting of an amino acid sequence of SEQ ID NO: 10 or (34) a protein (i) consisting of an amino acid sequence obtained by deletion, substitution, or addition of one or several amino acids in the amino acid sequence of SEQ ID NO: 10 and (ii) functioning as a hypophosphite transporter together with the HtxB protein and the HtxC protein or with the HtxB protein, the HtxC protein, and the HtxE protein; the HtxE protein may be (35) a protein consisting of an amino acid sequence of SEQ ID NO: 12 or (36) a protein (i) consisting of an amino acid sequence obtained by deletion, substitution, or addition of one or several amino acids in the amino acid sequence of SEQ ID NO: 12 and (ii) functioning as a phosphate transporter together with the HtxB protein, the HtxC protein, and the HtxD protein.

The above-described HtxBCDE gene is composed of polynucleotides respectively encoding the HtxB, HtxC, HtxD, and HtxE proteins.

The polynucleotide encoding the HtxB protein may be (37) a nucleotide consisting of a base sequence of SEQ ID NO: 5 or (38) a nucleotide (i) being hybridizable, under a stringent condition, with a base sequence complementary to the polynucleotide consisting of the base sequence of SEQ ID NO: 5 and (ii) encoding a protein functioning as a hypophosphite transporter together with the HtxC protein and the HtxD protein or with the HtxC protein, the HtxD protein, and the HtxE protein; the polynucleotide encoding the HtxC protein may be (39) a nucleotide consisting of a base sequence of SEQ ID NO: 7 or (40) a nucleotide (i) being hybridizable, under a stringent condition, with a base sequence complementary to the polynucleotide consisting of the base sequence of SEQ ID NO: 7 and (ii) encoding a protein functioning as a hypophosphite transporter together with the HtxB protein and the HtxD protein or with the HtxB protein, the HtxD protein, and the HtxE protein; the polynucleotide encoding the HtxD protein may be (41) a nucleotide consisting of a base sequence of SEQ ID NO: 9 or (42) a nucleotide (i) being hybridizable, under a stringent condition, with a base sequence complementary to the polynucleotide consisting of the base sequence of SEQ ID NO: 9 and (ii) encoding a protein functioning as a phosphate transporter together with the HtxB protein and the HtxC protein or with the HtxB protein, the HtxC protein, and the HtxE protein; the polynucleotide encoding the HtxE protein may be (43) a nucleotide consisting of a base sequence of SEQ ID NO: 11 or (44) a nucleotide (i) being hybridizable, under a stringent condition, with a base sequence complementary to the polynucleotide consisting of the base sequence of SEQ ID NO: 11 and (ii) encoding a protein functioning as a hypophosphite transporter together with the HtxB protein, the HtxC protein, and the HtxD protein.

Note that HtxE protein is a protein which serves as a cell membrane-bound protein. As such, HtxBCD protein, which is a part of the above-described HtxBCDE protein excluding the HtxE protein can be utilized as a hypophosphite transporter protein.

In a transformant in accordance with an embodiment of the present invention, a signal peptide of a hypophosphite binding protein, which is a constituent element of the hypophosphite transporter protein, is substituted with a signal peptide derived from a host or a species of organism closely related to the host, by genetic modification which may be a well-known method.

In the transformant in accordance with an embodiment of the present invention, a gene encoding a phosphite dehydrogenase protein can be further introduced. In this arrangement, the reduced phosphorous compound taken into cells can be efficiently converted to phosphate. This allows the transformant in accordance with an embodiment of the present invention to proliferate better dependently on phosphite.

The gene encoding a phosphite dehydrogenase protein can be a gene derived from *Pseudomonas stutzeri* WM88 (e.g., PtxD gene).

More specifically, the phosphite dehydrogenase protein can be a protein consisting of the following protein (45) or (46), a protein including, as at least part thereof, the following protein (45) or (46), a protein consisting of a protein encoded by a gene consisting of the following polynucleotide (47) or (48), or a protein including, as at least part thereof, the protein encoded by the gene consisting of the following polynucleotide (47) or (48):

(45) a protein consisting of the amino acid sequence of SEQ ID NO: 14;

(46) a protein (i) consisting of an amino acid sequence obtained by deletion, substitution, or addition of one or several amino acids in the amino acid sequence of SEQ ID NO: 14 and (ii) having phosphite dehydrogenase activity;

(47) a polynucleotide consisting of the base sequence of SEQ ID NO: 13; or

(48) a polynucleotide (i) being hybridizable, under a stringent condition, with DNA consisting of a base sequence complementary to the base sequence of SEQ ID NO: 13, and (ii) encoding a protein which has phosphite dehydrogenase activity.

Whether a protein has phosphite dehydrogenase activity can be checked on the basis of whether or not the protein produces $HPO_4^{2-}$ by $NADP^+$ dependently or $NADP^+$ dependently oxidizing phosphite. More specifically, it can be determined that a chosen protein has phosphite dehydrogenase activity, if $HPO_4^{2-}$ is produced after the chosen protein, $HPO_3^{2-}$, and $NAD^+$ or $NADP^+$ are mixed together.

The transformant in accordance with an embodiment of the present invention may be preferably further defective in a function of a gene encoding an alkaline phosphatase protein (e.g., PhoA gene). For example, the alkaline phosphatase protein acts to convert, to phosphate, phosphite which is present outside the cells, and to thereby decrease a phosphite concentration outside the cells. Further, an alkaline phosphatase protein of a species of organism other than *E. coli* may have the above-described activity, similarly to the alkaline phosphatase protein of *E. coli*. The transformant defective in the function of the gene encoding an alkaline phosphatase protein can keep the phosphite concentration outside the cells high. Accordingly, with this configuration, an amount of the reduced phosphorous compound taken into cells can be increased. This consequently allows the transformant in accordance with an embodiment of the present invention to grow better dependently on the reduced phosphorous compound.

Different types of alkaline phosphatase protein exist in cells of different species of organism. Therefore, there is no limitation to a particular type of alkaline phosphatase protein which has a function defective in the transformant in accordance with the present embodiment. It is possible to determine as appropriate, depending on a host, the gene encoding an alkaline phosphatase protein, which gene has a function that is caused to be defective in the host.

For example, in a case where the host of the transformant is cyanobacteria (*Synechococcus elongatus* PCC7942), the alkaline phosphatase protein can be a protein consisting of a protein encoded by a gene consisting of the following polynucleotide (49) or (50), a protein including, as at least part thereof, a protein encoded by a gene consisting of the following polynucleotide (49) or (50), a protein consisting of the following protein (51) or (52), or a protein including, as at least part thereof, the following protein (51) or (52):

(49) a polynucleotide consisting of the base sequence of SEQ ID NO: 61; or

(50) a polynucleotide (i) being hybridizable, under a stringent condition, with DNA consisting of a base sequence complementary to the base sequence of SEQ ID NO: 61, and (ii) encoding a protein which has an alkaline phosphatase activity.

(51) a protein consisting of the amino acid sequence of SEQ ID NO: 62;

(52) a protein (i) consisting of an amino acid sequence obtained by deletion, substitution, or addition of one or several amino acids in the amino acid sequence of SEQ ID NO: 62 and (ii) having an alkaline phosphatase activity;

Whether a protein has an alkaline phosphatase activity can be checked on the basis of whether the protein converts phosphite to phosphate. More specifically, it can be determined that a chosen protein has an alkaline phosphatase activity, if phosphate is produced after the chosen protein and phosphite are mixed together.

With regard the wording "an amino acid sequence obtained by deletion, substitution, or addition of one or several amino acids", a position where one or several amino acids are deleted, substituted or added is not particularly limited.

Further, the number of amino acids intended by the wording "one or several amino acids" is not particularly limited, and can be not more than 50, not more than 40, not more than 30, not more than 20, not more than 19, not more than 18, not more than 17, not more than 16, not more than 15, not more than 14, not more than 13, not more than 12, not more than 11, not more than 10, not more than 9, not more than 8, not more than 7, not more than 6, not more than 5, not more than 4, not more than 3, not more than 2, or not more than 1.

It is preferable that the substitution of an amino acid be a conservative substitution. Note that the term "conservative substitution" refers to a substitution of a particular amino acid by another amino acid having a chemical property and/or a structure that is/are similar to that/those of the particular amino acid. Examples of the chemical property include a degree of hydrophobicity (hydrophobicity and hydrophilicity) and electric charge (neutrality, acidity, and basicity). Examples of the structure include an aromatic ring, an aliphatic hydrocarbon group, and a carboxyl group, which are present as a side chain or as a functional group of a side chain.

Examples of the conservative substitution include a substitution between serine and threonine, a substitution between lysine and arginine, and a substitution between phenylalanine and triptophan. The substitution in an embodiment of the present invention is, of course, not limited to the above-described substitutions.

The term "stringent condition" as used herein refers to a condition under which a so-called base sequence specific double-stranded polynucleotide is formed whereas a base-sequence non-specific double-stranded polynucleotide is not formed. In other words, the "stringent condition" can be expressed as a condition under which hybridization is carried out at a temperature in a range from (i) a melting temperature (Tm) of nucleic acids having a high homology (e.g., a perfectly-matched hybrid) to (ii) 15° C. lower than the melting temperature (Tm), preferably 10° C. lower than the melting temperature (Tm), further preferably 5° C. lower than the melting temperature (Tm).

In one example of the stringent condition, hybridization can be carried out in a buffer solution (including 0.25M $Na_2HPO_4$, pH 7.2, 7% SDS, 1 mM EDTA, and 1×Denhardt's solution) for 16 hours to 24 hours at a temperature in a range from 60° C. to 68° C., preferably at 65° C., further preferably at 68° C., and then washing can be carried out twice in a buffer solution (including 20 mM $Na_2HPO_4$, pH 7.2, 1% SDS, and 1 mM EDTA) for 15 minutes at a temperature in a range from 60° C. to 68° C., preferably at 65° C., further preferably at 68° C.

In another example, prehybridization is carried out overnight at 42° C. in a hybridization solution (including 25% formamide or 50% formamide (for a severer condition), 4×SSC (sodium chloride/sodium citrate), 50 mM Hepes pH 7.0, 10×Denhardt's solution, and 20 μg/ml denatured salmon sperm DNA), and then hybridization is carried out by adding a labeled probe thereto and keeping a resulting solution at 42° C. overnight. In washing following the hybridization, conditions for a washing solution and a temperature are approximately "1×SSC, 0.1% SDS, 37° C.", approximately "0.5×SSC, 0.1% SDS, 42° C." for a severer condition, approximately "0.2×SSC, 0.1% SDS, 65° C." for a further severer condition. As such, as the conditions for the washing following the hybridization become severer, the specificity of hybridization becomes higher. However, the above-indicated combinations of conditions on SSC, SDS, and temperature are merely examples. A person skilled in the art can provide a stringency similar to the above by appropriately combining the above-described or other elements (e.g., a probe concentration, a probe length, and a time period for a hybridization reaction) that determine the stringency of hybridization. This is disclosed in, for example, Sambrook et al., Molecular Cloning, A Laboratory Manual, 3rd Ed., Cold Spring Harbor Laboratory (2001).

[3. Method for Detecting Presence of Reduced Phosphorus Compound]

A method for detecting the presence of a reduced phosphorous compound in accordance with an embodiment of the present invention is a method for detecting the presence of a reduced phosphorous compound in a culture medium which is a detection target, the method including the steps of: culturing a transformant in accordance with an embodiment of the present invention, with use of a culture medium as a detection target; and detecting whether or not the transformant proliferated in the step of culturing.

With this arrangement, it is possible to provide a method for detecting the presence of a reduced phosphorous compound which method uses a transformant whose proliferation depends on an inexpensive reduced phosphorous compound, and thus enables eliminating the need for a complicated step and reducing cost for proliferation of the transformant.

The above method for detecting the presence of a reduced phosphorous compound can be used in, for example, determining a place in which outdoor culture such as open pond culture is to be conducted. A reduced phosphorous compound (e.g., phosphite and hypophosphite) is absent or if any, only a very small amount of reduced phosphorous compound is present. In this condition, a transformant in accordance with an embodiment of the present invention cannot proliferate in nature even if the transformant leaks into nature. However, a reduced phosphorous compound may be contained in an agricultural material, an industrial material, and the like. As such, a reduced phosphorous compound which has leaked out of such materials may be present in nature. In outdoor culture, if a transformant in accordance with an embodiment of the present invention is cultured in a place containing a reduced phosphorous compound, the transformant may proliferate in a scale greater than what was intended by a person skilled in the art.

In order to avoid the above-described problem, a method for detecting in accordance with an embodiment of the present invention can be used. Specifically, a substance, such as water, which is present in a chosen place for conducting proliferation of a transformant in accordance with an embodiment of the present invention is collected, and the sample thus collected is supplied as a phosphorus source to a culture medium. The transformant in accordance with an embodiment of the present invention is cultured in the culture medium which serves as a detection target. If a result of the culture shows that the transformant in accordance with an embodiment of the present invention did not proliferate, it can be determined that no reduced phosphorous compound is contained in the place from which the sample was collected. It can then be determined that it is possible to cause the transformant in accordance with an embodiment of the present invention to proliferate in the place from which the sample was collected.

In the method for detecting the presence of a reduced phosphorous compound in accordance with the present embodiment, it can be determined that a reduced phosphorous compound is contained in the culture medium as the detection target if the transformant proliferated in the step of culturing. In contrast, in the method, it can be determined that no reduced phosphorous compound is contained in the culture medium as the detection target if the transformant did not proliferate in the step of culturing.

Ingredients and form of the culture medium as a detection target is not particularly limited. For example, the form of the culture medium as a detection target can be a liquid form or a solid form.

In a case where the culture medium as a detection target is in the liquid form, whether or not the transformant proliferated in the step of culturing can be detected in the step of detecting, by measuring for example, turbidity (e.g., OD600) of the culture medium. In contrast, in a case where the culture medium as a detection target is in the solid form, whether or not the transformant proliferated in the step of culturing can be detected in the step of detecting, by confirming the presence of colonies of the transformant, which are formed on the culture medium in the solid form.

The reduced phosphorous compound to be detected by the method for detecting in accordance with the present embodiment is not particularly limited. Examples of the reduced phosphorous compound encompass phosphite and hypophosphite.

Aspects of the present invention can also be expressed as follows:

A transformant in accordance with an aspect of the present invention is a transformant which is defective in functions of a gene encoding a phosphate transporter protein and a gene encoding a phosphate ester transporter protein and into which a gene encoding a hypophosphite transporter protein is introduced, the transformant being incapable of utilizing phosphate for proliferation but capable of utilizing phosphite for proliferation, the hypophosphite transporter protein including a hypophosphite binding protein as a constituent element, a signal peptide of the hypophosphite binding protein being substituted with a signal peptide derived from a host or a species of organism closely related to the host.

In a transformant in accordance with an aspect of the present invention, a gene encoding a phosphite dehydrogenase protein can be further introduced.

A transformant in accordance with an aspect of the present invention can be further configured to be defective in a function of a gene encoding an alkaline phosphatase protein.

A transformant in accordance with an aspect of the present invention can be a transformant of a prokaryote.

A transformant in accordance with an aspect of the present invention can be a transformant of cyanobacteria.

A method for detecting the presence of a reduced phosphorous compound in accordance with an aspect of the present invention is a method for detecting the presence of a reduced phosphorous compound in a culture medium which is a detection target, the method including the steps of: culturing a transformant in accordance with an aspect of the present invention, with use of a culture medium as a detection target; and detecting whether or not the transformant proliferated in the step of culturing.

EXAMPLES

The following description will discuss examples of the present invention.

<1. Impartment of Phosphite-Utilizing Ability (Ability to Convert Phosphite to Phosphate)>

An expression vector for imparting a phosphite-utilizing ability to cyanobacteria was prepared. First, pNSHA (Reference Literature 1: Watanabe et al., Mol Microbiol. 2012 February; 83(4): 856-65) which is an expression vector for *Synechococcus elongatus* PCC7942 strain (hereinafter referred to as "7942 strain") was cleaved by EcoRI and HindIII. Into the expression vector which has been cleaved, a DNA fragment (approximately 3.6 kb) amplified by PCR using a chromosome of *Ralstonia* sp. 4506 strain (hereinafter referred to as "4506 strain") as a template as well as the following primers was inserted using In-Fusion HD cloning kit (Takara-Bio Inc.):

P0048:
(SEQ ID NO: 23)
5'-acagaccatggaattcGTGTCATATCACGACATTACCATCG-3';
and

P0049:
(SEQ ID NO: 24)
5'-caaaacagccaagcttTCACGCCGCCTTTACTCCCGGATAC-3'

A plasmid pNSptxAD (SEQ ID NO: 63) thus obtained was introduced into a 7942 strain by spontaneous transformation. Specifically, first, the 7942 strain was cultured in a BG-11 medium (10 ml) until OD750 was approximately 0.7 to 1.0, and then bacteria were collected by centrifugation (6000 rpm, 5 min). Cells thus collected were re-suspended in 1.0 ml of a BG-11 medium. To 400 µl of a suspension thus obtained, approximately 0.1 µg of the above plasmid was added and mixed by a shaker in a 30° C. incubator for 12 hours while shielded from light with aluminum foil.

Then, the aluminum was removed and a resultant mixture was mixed for another 1 hour to obtain a mixed solution of the bacteria and the plasmid. The mixed solution was spread on a BG-11 plate medium containing spectinomycin (40 µg/ml), and was cultured in a plant incubator (illuminance: 2000 lux to 3000 lux, temperature: 30° C.). Approximately 10 days later, a colony which had appeared was obtained using a colony picker and streaked on a BG-11 plate medium having the same composition as the above plate medium.

Approximately 5 days later, a colony was obtained and subjected to analysis as a modified body (spectinomycin resistance strain). The spectinomycin resistance strain was cultured, while supplied with 2% of $CO_2$ gas, in a BG-11 liquid medium (BG-11Pt) which contained phosphite (final concentration: 0.2 mM) as a phosphorus source and to which 0.1 mM IPTG had been added. As a result, a transformant thus obtained was able to grow by utilizing the phosphite. In contrast, a wild strain was unable to proliferate by utilizing the phosphite. It was thus indicated that this express system enabled PtxD to be functionally expressed, that is, the express system imparted a phosphite-utilizing ability.

<2-1. Introduction of Wild-Type HtxBCDE-PtxD Fusion Plasmid>

HtxBCDE protein is a hypophosphite transporter derived from *Pseudomonas stutzeri* WM88 strain. An expression plasmid for HtxBCDE protein was prepared by the following method.

First, pNSptxAD was cleaved by SalI and EcoRI, and approximately 9.9 kb of a DNA fragment thus obtained was used as a vector. A DNA fragment (approximately 3.3 kb) was prepared as an insert DNA by amplification using pSTVhtxAE (Reference Literature 2: Hirota et al., Sci. Rep. 2017, 44748) (SEQ ID NO: 64) as a template as well as the following primers:

P0132:
(SEQ ID NO: 25)
5'-ACAGACCATGGAATTCATGCAAGTTTTTACTCTGTT-3';
and

P0133:
(SEQ ID NO: 26)
5'-AGCTGAAGGCGTCGACTAGTAGTTGCGGGCCGCGA-3'.

The vector and the insert DNA were ligated by use of In-Fusion HD Cloning Kit. Then, a resultant plasmid pNShtxBCDE-ptxD (SEQ ID NO: 65) was introduced into a 7942 strain. A transformant thus obtained was cultured in 50 mL of BG-11, into which 0.1 mM IPTG and 40 µg/mL spectinomycin had been added, for 7 days and then subjected to centrifugation to obtain a pellet of bacteria.

The pellet of bacteria was suspended in 2 mL of a MOPS(0) solution, and then a resultant suspension was homogenized ultrasonically (Digital sonifier, BRANSON) with an output of 20% for 10 minutes. The MOPS(0) solution thus ultrasonically homogenized was dispensed into centrifuge tubes (Centrifuge Tubes, BECKMAN, 349622), and the centrifuge tubes were subjected to ultracentrifugation (270,000×g, 4° C., 30 minutes) using a ultracentrifugal separator (Optima™ TLX Ultracentrifuge, BECKMAN COULTER).

A supernatant was collected from each of the tubes after the ultracentrifugation and used as a crude extract for measurement of phosphite dehydrogenase activity. A reaction solution in a total amount of 1000 containing the crude extract (amount of protein: 10 μg), NAD$^+$ (1 mM), phosphite (1 mM), and MOPS-KOH buffer (20 mM, pH 7.4) was prepared, and the reaction solution was heated to a temperature of 37° C. to start a reaction.

An absorbance (340 nm) of each sample was measured for a predetermined time (0 min to 30 min). Phosphite dehydrogenase activity was evaluated such that an amount of NADH produced by 1 mg of protein per unit of time was considered to be 1 unit. As a result, approximately 40 milliunits of PtxD activity was detected in the transformant. Even though sufficient PtxD activity was thus detected, no proliferation was observed in a BG-11Pt medium. This suggested that HtxBCDE was not expressed functionally.

<2-2. Expression of HtxBCDE Protein Using HtxBCDE-PtxD Fusion Plasmid Containing HtxB Gene which has Undergone Substitution>

Expression plasmids were prepared by substituting a signal peptide sequence (SEQ ID NO: 60) of HtxB protein with respective signal peptide sequences derived from three types of bacteria proteins of cyanobacteria and the like, and an effect of each of these expression plasmids was studied. First, an expression vector for HtxB was prepared by inverse PCR using pSTVhtxAE as a template as well as primers P0268 and P0269 to remove a signal peptide sequence:

P0268:
(SEQ ID NO: 27)
5'-CATGGTGATGCTCCTAGGATCCCCG-3';
and

P0269:
(SEQ ID NO: 28)
5'-GCTGAGGTTGTCAATGGTAAACTTC-3'.

Figure 3:
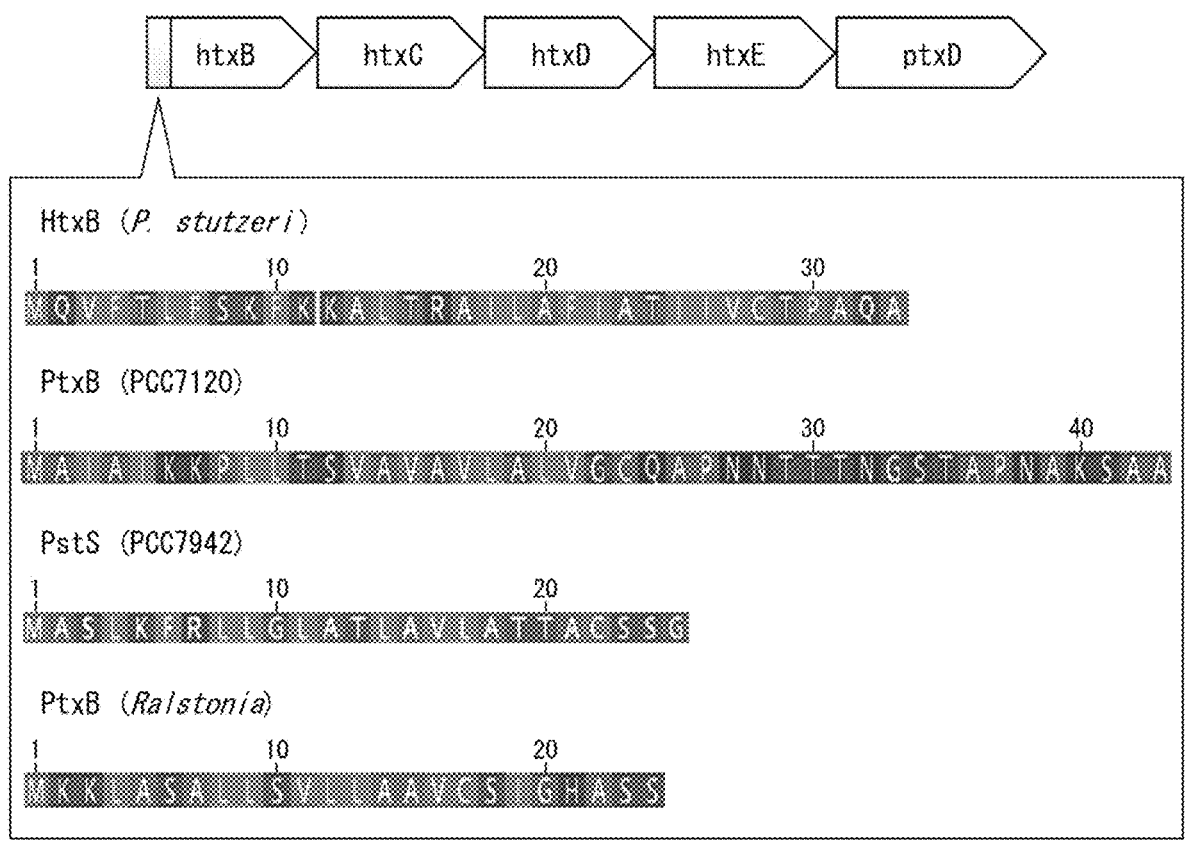
FIG. 3 is a diagram illustrating a signal peptide of HtxB, signals peptide to be substituted with a signal peptide of HtxB, and an HtxBCDE-PtxD fusion plasmid in which a signal peptide of HtxB has been substituted.

As a signal peptide to be substituted with the signal peptide of HtxB, a signal peptide of PtxB derived from a 4506 strain (SEQ ID NOS: 58 and 59), a signal peptide of PstS derived from a 7942 strain (SEQ ID NOS: 56 and 57), and a signal peptide of PtxB derived from *Anabaena* sp. PCC7120 strain (hereinafter referred to as "7120 strain") (SEQ ID NOS: 54 and 55) were each used. As a sequence of each of these signal peptides, a sequence of a signal peptide obtained by use of EMBOSS sigcleave (genome-.sourceforge.followed by_net/apps/release/6.5/emboss/apps/sigcleave.html) was used as illustrated in FIG. 3.

DNA fragments of the signal peptides used were DNA fragments amplified by PCR using respective chromosomes of the 4506, 7942, and 7120 strains as templates and respective primer pairs (P0270 (SEQ ID NO: 17)/P0271 (SEQ ID NO: 18), P0274 (SEQ ID NO: 21)/P0275 (SEQ ID NO: 22), and P0272 (SEQ ID NO: 19)/P0273 (SEQ ID NO: 20), see Table 1).

TABLE 1

| SEQ ID NO. | Name | Sequence (5'-3') |
|---|---|---|
| 17 | 270 | CCTAGGAGCATCACCATGAAAAAACTCGCATC |
| 18 | 271 | ATTGACAACCTCAGCGGATGATGCATGGCC |
| 19 | 272 | CCTAGGAGCATCACCATGGCGATCGCAATC |
| 20 | 273 | ATTGACAACCTCAGCAGCTGCGCTCTTTGC |

TABLE 1-continued

| SEQ ID NO. | Name | Sequence (5'-3') |
|---|---|---|
| 21 | 274 | CCTAGGAGCATCACCATGGCTTCCCTAAAATTCC |
| 22 | 275 | ATTGACAACCTCAGCACCAGAGCTGCAAGC |

Figure 4:
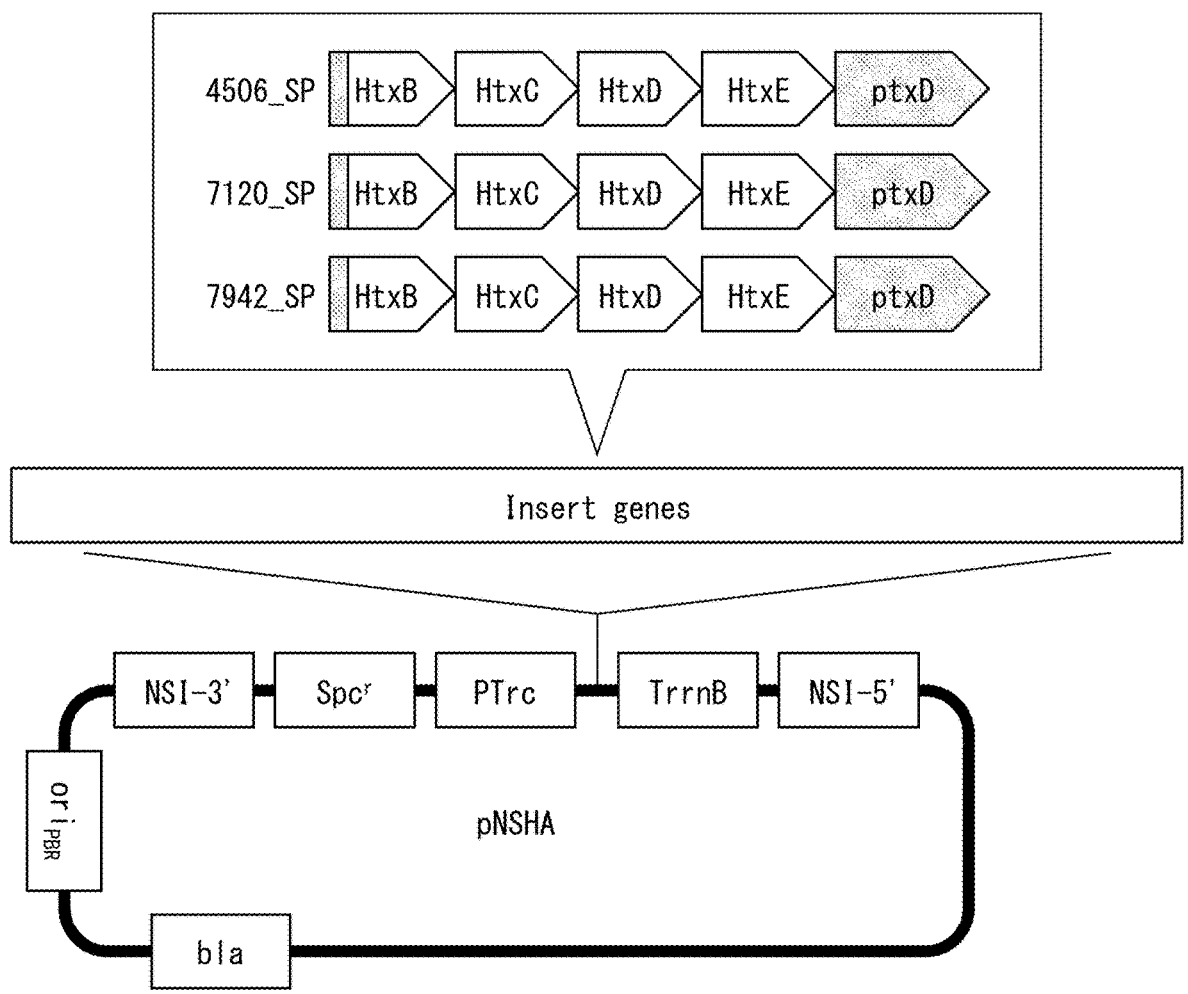
FIG. 4 is a diagram illustrating structures of plasmids in accordance with an Example.

Each of these DNA fragments and the vector DNA were ligated in a similar manner to the above-described technique. Plasmids thus obtained are referred to as pSTVhtxBE$_{4506\text{-}SP}$, pSTVhtxBE$_{7942\text{-}SP}$, and pSTVhtxBE$_{7120\text{-}SP}$. Subsequently, with use of these three types of plasmids and in a similar manner to the above-described method for preparing pNShtxBCDE-ptxD, HtxBE gene sequences in each of which a signal peptide sequence had been substituted were respectively prepared. Plasmids thus obtained are referred to as pNShtxBE$_{4506\text{-}SP}$-ptxD, pNShtxBE$_{7942\text{-}SP}$-ptxD, and pNShtxBE$_{7120\text{-}SP}$-ptxD (see FIG. 4, in which "SP" is an acronym for "signal peptide"). These three types of plasmids were each used to transform 7942 strain to obtain a strain expressing HtxBE-ptxD. These strains were each cultured in BG-11 mediums (a phosphor-free medium, a phosphate-containing medium, and a phosphite-containing medium) containing spectinomycin (40 μg/ml) and 0.1 mM IPTG to study proliferation of the strains.

The results are shown in FIG. 5. (a) of FIG. 5 shows images of results of phosphate-dependent proliferation and phosphite-dependent proliferation. (b) of FIG. 5 shows graphs indicative of results of phosphate-dependent proliferation and phosphite-dependent proliferation. Note that "Pi" represents BG-11 containing phosphate, "Pt" represents BG-containing phosphite, and "none" represents BG-11 containing no phosphor. "4506-SP" represents a 7942 strain transformed by pNShtxBE$_{4506\text{-}SP}$-ptxD (SEQ ID NO: 67), "7942-SP" represents a 7942 strain transformed by pNShtxBE$_{7942\text{-}SP}$-ptxD (SEQ ID NO: 68), and "7120-SP" represents a 7942 strain transformed by pNShtxBE$_{7120\text{-}SP}$-ptxD. As shown in (a) and (b) of FIG. 5, it was confirmed that a strain (RH693) into which an expression construct pNShtxBE$_{7120\text{-}SP}$-ptxD (SEQ ID NO: 66), in which a signal peptide sequence had been substituted with a signal peptide sequence derived from PtxB of the 7120 strain, was introduced proliferated dependently on phosphite. It was thus revealed that in order for an Htx transporter to be expressed functionally in cyanobacteria, it is effective to employ a signal peptide sequence having a higher compatibility.

<3. Disruption of Phosphor Transporter Gene of 7942 Strain>

In order to cause a defect in dependency on phosphate, a phosphate transporter gene of a 7942 strain was disrupted. From genome data (cyanobase: genome.microbedb.followed by jp/cyanobase/) of 7942 strain published in Kazusa Genome Resource, it was suggested that the following two types of phosphate transporter genes are present in PCC7942: pit (gene name in the database: Synpcc7942_0184) and sphX-pstSCAB (gene name in the database: Synpcc7942_2445-2441). Based on the suggestion, the two types of genes were disrupted using homologous recombination. The genes were disrupted by: carrying out overlap extension-PCR to prepare (i) a DNA fragment in which a gentamicin resistance gene (SEQ ID NO: 29) was inserted between approximately 1 kb of a sequence upstream of pit (SEQ ID NO: 1) and approximately 1 kb of a sequence downstream of pit and (ii) a DNA fragment in which a kanamycin resistance gene (SEQ ID NO: 30) was inserted between approximately 1.5 kb of a sequence upstream of sphX-pstSCAB (SEQ ID NO: 3) and approximately 1.5 kb of a sequence downstream of sphX-pstSCAB; and transforming a 7942 strain with use of approximately 0.1 μg of each of the DNA fragments thus obtained. Primers shown in Table 2 were used.

TABLE 2

| SEQ ID NO. | Name | Sequence (5'-3') |
|---|---|---|
| 43 | 2445us1500-f | GGCGGACATTGCCGACGCCAACGCGGG |
| 44 | 2445us-Km-r2 | cgctcacaattccacTTAGACTTTGGTGCGATCGGTA |
| 45 | 2445us-Km-f3 | TCGCACCAAAGTCTAAgtggaattgtgagcggataacaat |
| 46 | Km-2441ds-r4 | GTGATGGCTTCAGGGGTttagaaaaactcatcgagcatcaaatga |
| 47 | Km-2441ds-f5 | gatgagttttctaaACCCCTGAAGCCATCACCCTTT |
| 48 | 2441ds1500-r | GCCCATCGAGGTGGAGCCGTTGG |
| 49 | 0184us1000-f | CCGGTGCGAGATGTTCAGCG |
| 50 | 0184us-Gm-r | gcgtcacccggcaaTCATAGCGAGGCGGCAAGGACT |
| 51 | 0181us-Gm-f | GCCGCCTCGCTCATGAttgccgggtgacgcacaccgtggaaa |
| 52 | Gm-0184ds-r | CAACAACGGTGAGCAttaggtggcgtacttgggtc |
| 53 | Gm-0184ds-f | gtaccgccacctaaTGCTCACCGTTGTTGTCAGG |
| 4 | 0184ds1000-r | ACCTGTCAGAAATTGGCGATCGAT |

Confirmation of disruption of the genes was conducted by PCR. There were a plurality of copies of genes to be disrupted in the 7942 strain, and it was confirmed that all of the copies of genes had been disrupted. Pit gene disruption was conducted with respect to RH693, and a disrupted strain (RH713) was obtained in a BG-11 agar medium containing gentamicin (2.0 μg/ml). Pit-pst double disruption was conducted such that Pst gene disruption was conducted with respect to RH713, and screening was conducted in a BG-11 (Pt) agar medium containing gentamicin (2.0 μg/ml), kanamycin (10 μg/ml), and 0.1 mM IPTG to obtain a disrupted strain (hereinafter referred to as "RH714").

In order to confirm dependency of RH714 on phosphite, RH714 was cultured in BG-11 (Pt). Then, the RH714 was inoculated on BG-11 (containing phosphate) or BG-11 (Pt) and cultured while irradiated with white light (50 μmol photons/m$^2$/s) and supplied with 2% of $CO_2$ gas.

FIG. 6 shows results of conducting the culture. (a) and (c) of FIG. 6 each show images of states of proliferation of RH714 and a wild strain after 192 hours. (b) and (d) of FIG. 6 each show a graph indicative of changes over time of proliferation of RH714 and the wild strain. Note that (a) and (b) show results of culture conducted in BG-11 (containing phosphite), and (c) and (d) show results of culture conducted in BG-11 (containing phosphate). As shown in (a) through (d) of FIG. 6, RH714 grew well in BG-11 containing phosphite but could not proliferate at all in the ordinary BG-11 medium. It was confirmed from these results that RH714 is unable to utilize phosphate but proliferates in a culture medium containing phosphite as a phosphorus source.

Further, in order to study effects of various phosphate compounds on proliferation of RH714, similar culture was conducted in culture mediums respectively obtained by replacing the phosphorus source of BG-11 medium with various types of phosphorus compounds. As a sample phosphorus compound, aminoethylphosphonic acid, methylphosphonic acid, glucose 6-phosphate, ATP, pyrophosphoric acid, and salmon sperm DNA were each used in a BG-11 medium at a final concentration of 0.2 mM in terms of phosphate. Further, in order to study influence of a phosphorus source contained in a natural river on proliferation of RH714, a similar experiment was conducted using water collected from a lake or a river in Higashi-Hiroshima City.

The results are shown in FIG. 7. FIG. 7 shows images of states of proliferation of RH714 cultured in the culture mediums containing respective phosphorus compounds as a phosphorus source. In all of the images in which a phosphorus source other than phosphite was used, RH714 was unable to proliferate. It was confirmed from these results that the series of genetic modifications successfully imparted a full phosphite dependency to the 7942 strain.

<4. Escape Assay and Measurement of Survivability>

RH714 was cultured in 25 mL of a BG-11Pt liquid medium for 5 days and collected by centrifugation. Bacteria thus collected were washed 3 times in a phosphate-free BG-11 medium and re-suspended in approximately 10 mL of an identical culture medium. 0.1 mL of a resultant suspension containing the bacteria was $10^{-5}$-fold to $10^{-8}$-fold diluted. Then, 0.1 mL of a resultant diluted suspension containing the bacteria was spread on a BG-11Pt plate (permissive culture medium). The remaining portion of the suspension containing the bacteria was spread, in an amount of approximately 2.0 mL, on each of five BG-11 plates (non-permissive culture mediums), which were prepared by using a 245 mm×245 mm square dish.

These plates were cultured at 30° C. for 28 days while irradiated with white light. The plates were observed every day and appearance of colonies was checked. On the non-permissive culture mediums, RH714 growth was not confirmed. A detection limit in the present experimental system was expressed by a numerical value obtained by the following calculation formula:

[Detection limit (escapee/CFU)]=1/([number of colonies formed in permissive culture medium (CFU)]×[dilution factor (−)]/[amount of spread culture fluid (mL)]×[amount of culture fluid used (mL)])

A detection limit in the present experiment was $3.6×10^{-11}$.

Further, in order to measure survivability of RH714, 10 mL of bacteria in a mid-log phase were collected, washed 3 times in 5 mL of phosphor-free BG-11, and re-suspended in mL of phosphor-free BG-11. A resultant suspension containing cells was inoculated on a BG-11 liquid medium and a BG-11Pt liquid medium so as to achieve an absorbance (OD750 value) of approximately 0.8, and an appropriately diluted culture fluid was spread on the BG-11Pt plate every 3 days. Formation of colonies was observed 10 days later, and the number of surviving bacteria was counted.

The results are shown in FIG. 8. FIG. 8 shows a graph indicative of changes over time of the number of surviving bacteria of RH714. As shown in FIG. 8, the number of surviving bacteria of RH714 was 0 in the BG-11 liquid medium. In contrast, RH714 maintained a large number of surviving bacteria in the BG-11Pt liquid medium. It was thus confirmed that a high biocontainment effect was obtained by RH714.

Note that SEQ ID NO: 31 corresponds to a base sequence of a full length of ptxB (derived from *Ralstonia* sp. 4506) gene, SEQ ID NO: 32 corresponds to an amino acid sequence of a full length of PtxB (derived from *Ralstonia* sp. 4506) protein, SEQ ID NO: 35 corresponds to a base sequence of a full length of ptxB (derived from *Anabaena* sp. 7120) gene, and SEQ ID NO: 36 corresponds to an amino acid sequence of a full length of PtxB (derived from *Anabaena* sp. 7120) protein.

<5. Another Example of Expression of HtxBCDE Protein Using HtxBCDE-PtxD Fusion Plasmid Containing HtxB Gene which has Undergone Substitution>

Expression plasmids for HtxBCDE protein were prepared by substituting a signal peptide sequence (SEQ ID NO: 60) of HtxB protein with respective signal peptide sequences derived from three types of proteins of cyanobacteria and the like, and each of the expression plasmids was introduced into *E. coli.*

An expression vector for HtxB was prepared by a procedure similar to the above section <2-2> such that a signal peptide sequence was removed from the expression vector. As a signal peptide to be substituted with the signal peptide of HtxB, a signal peptide of PtxB derived from a 4506 strain (SEQ ID NOS: 58 and 59), a signal peptide of PstS derived from a 7942 strain (SEQ ID NOS: 56 and 57), and a signal peptide of PtxB derived from *Anabaena* sp. PCC7120 strain (hereinafter referred to as "7120 strain") (SEQ ID NOS: 54 and 55) were each used.

Each of DNA fragments of these signal peptides and vector DNA were ligated in a similar manner to the above-described technique. Plasmids thus obtained are referred to as $pSTVhtxBE_{4506\text{-}SP}$, $pSTVhtxBE_{7942\text{-}SP}$, and $pSTVhtxBE_{7120\text{-}SP}$. With use of each of the plasmids $pSTVhtxBE_{4506\text{-}SP}$, $pSTVhtxBE_{7942\text{-}SP}$, and $pSTVhtxBE_{7120\text{-}SP}$, *E. coli* strain MT2012 into which ptxD/pTWV229 (SEQ ID NO: 69) was introduced and in which a function of a gene encoding a phosphate ester transporter protein was made defective was transformed to obtain a strain expressing HtxBE-ptxD. These strains were each cultured in a morpholinopropanesulfonic acid (MOPS) medium (containing 0.5 mM of phosphite) containing chloramphenicol (30 μg/ml) and ampicillin (50 μg/ml) to study proliferation of the strains.

The results are shown in FIG. 9. FIG. 9 shows a graph indicative of results of phosphite-dependent proliferation. Note that "4506-SP" represents the MT2012 strain into which the plasmid $pSTVhtxBE_{4506\text{-}SP}$ was introduced, "7942-SP" represents the MT2012 strain into which the plasmid $pSTVhtxBE_{7942\text{-}SP}$ was introduced, and "7120-SP" represents the MT2012 strain into which the plasmid $pSTVhtxBE_{7120\text{-}SP}$ was introduced.

As shown in FIG. 9, it was confirmed that the strain into which a plasmid in which a signal peptide sequence was substituted with a signal peptide sequence derived from PtxB of the 4506 strain was introduced proliferated dependently on phosphite. Further, it was confirmed that the strain into which a plasmid in which a signal peptide sequence was substituted with a signal peptide sequence derived from PstS of the 7942 strain was introduced proliferated, although it took a longer time for the strain to start proliferating than the strain into which the plasmid in which a signal peptide sequence was substituted with the signal peptide sequence derived from PtxB of the 4506 strain. In contrast, the strain into which a plasmid in which a signal peptide sequence was substituted with a signal peptide sequence derived from PtxB of the 7120 strain was introduced did not proliferate.

This indicates that a compatible signal peptide varies among hosts, and it was revealed that in the case of *E. coli*, a good result is obtained by selecting a signal peptide of a species closely related to the *E. coli.*

INDUSTRIAL APPLICABILITY

An embodiment of the present invention can be widely used in fields which require transformants (e.g., the field of oral vaccine production, fields aiming at improvement of natural environment, and fields of biofuel production).

The invention claimed is:

1. A cyanobacterial transformant comprising a disrupted gene encoding a phosphate transporter protein, a disrupted gene encoding a phosphate ester transporter protein, and an inserted gene encoding a hypophosphite transporter protein, wherein:
   the cyanobacterial transformant is incapable of utilizing phosphate for proliferation but is capable of utilizing phosphite for proliferation;
   the hypophosphite transporter protein includes a hypophosphite binding protein as a constituent element; and
   a gene encoding a PtxB signal peptide derived from *Anabaena* sp. PCC7120 is substituted for a gene encoding a signal peptide of the hypophosphite binding protein.

2. The cyanobacterial transformant as set forth in claim 1, further comprising an inserted gene encoding a phosphite dehydrogenase protein.

3. The cyanobacterial transformant as set forth in claim 1, further comprising a disrupted gene encoding an alkaline phosphatase protein.

4. A method comprising;
   culturing the cyanobacterial transformant of claim 1 in a culture medium; and
   after culturing, detecting the cyanobacterial transformant proliferation, which is indicative of the presence of reduced phosphorous compound in the culture medium.

* * * * *

SEQUENCE LISTING

```
<160> NUMBER OF SEQ ID NOS: 69

<210> SEQ ID NO 1
<211> LENGTH: 1092
<212> TYPE: DNA
<213> ORGANISM: Synechococcus elongates PCC7942

<400> SEQUENCE: 1
atgatcgcgg ccttactgga actgggcagt agcgatcgca gttggctgat cttaggggtg     60
ttgctctgcc tcctgtttga actgatcaac ggcttccacg acagcgccaa cacgatcgcg    120
ccgctggtct acagtcgcgt actgacgcct tttaccgccg tgatttggag tagcctttgg    180
aatctcgtgg gggcgatcgc ctcgtccggt gcagtcgcct ttgggattgt ggcgctctta    240
ccgccaacca cggcagggca gaccccagac tggtgggccg tggcagcgct gttattggtg    300
gcgatcgcct ggaactggct gacgtggtgg cggggcattc ccctctccag ttcacaaacc    360
ctgatcgggg cgttgattgg tgttcactgg gggcaactgt ggagtgagca gtcctggact    420
tggcaggctt tgacggtgcc accgctcccc gccacgctag aagcgctgct actctcgccg    480
ttgctgggct ttgctctggc ctacggattg ctgagtctgg tgcgatcgcg cttgccaact    540
```

```
agcctagacc aactggaatc cttggcagag ccaaccctga cttggccaac ccgtagtagt    600
ctcttgctgg ctaccgcggg catgagcttc agccacggca ccaacgatgg gcaaaagggc    660
atgggactgc tgctcttgat tctggcgaca gccttgcccg atcgctttgc gactgcgttg    720
gagcagcacc acttacccct cggtatcaaa gtaaccgttg ccctcagtct ggcgatcggt    780
accctgattg gctggcaacg gatcaccac accctcggcg aagccatggg cgatcgcccc    840
ttaaccaccg cccaatccct ctcttctgct gcggtaacca ctgccacaat cctgacggcc    900
agtcgttggg ggttgccgat cagcaccacg caagtcctga cggcgggcat tgctggcagc    960
acactcgcca cccagacagc cctcaaccgc cagacaatcc gacgcttgct ctggacttgg   1020
ctgattaccc tgccgatcgc gattggctcg gcactgttgc tctacagtct cgggcgtgcg   1080
atttgggcct ga                                                      1092

<210> SEQ ID NO 2
<211> LENGTH: 363
<212> TYPE: PRT
<213> ORGANISM: Synechococcus elongates PCC7942

<400> SEQUENCE: 2

Met Ile Ala Ala Leu Leu Glu Leu Gly Ser Ser Asp Arg Ser Trp Leu
1               5                   10                  15

Ile Leu Gly Val Leu Leu Cys Leu Leu Phe Glu Leu Ile Asn Gly Phe
            20                  25                  30

His Asp Ser Ala Asn Thr Ile Ala Pro Leu Val Tyr Ser Arg Val Leu
        35                  40                  45

Thr Pro Phe Thr Ala Val Ile Trp Ser Ser Leu Trp Asn Leu Val Gly
    50                  55                  60

Ala Ile Ala Ser Ser Gly Ala Val Ala Phe Gly Ile Val Ala Leu Leu
65                  70                  75                  80

Pro Pro Thr Thr Ala Gly Gln Thr Pro Asp Trp Trp Ala Val Ala Ala
                85                  90                  95

Leu Leu Leu Val Ala Ile Ala Trp Asn Trp Leu Thr Trp Trp Arg Gly
            100                 105                 110

Ile Pro Leu Ser Ser Ser Gln Thr Leu Ile Gly Ala Leu Ile Gly Val
        115                 120                 125

His Trp Gly Gln Leu Trp Ser Glu Gln Ser Trp Thr Trp Gln Ala Leu
    130                 135                 140

Thr Val Pro Pro Leu Pro Ala Thr Leu Glu Ala Leu Leu Ser Pro
145                 150                 155                 160

Leu Leu Gly Phe Ala Leu Ala Tyr Gly Leu Leu Ser Leu Val Arg Ser
                165                 170                 175

Arg Leu Pro Thr Ser Leu Asp Gln Leu Glu Ser Leu Ala Glu Pro Thr
            180                 185                 190

Leu Thr Trp Pro Thr Arg Ser Ser Leu Leu Ala Thr Ala Gly Met
    195                 200                 205

Ser Phe Ser His Gly Thr Asn Asp Gly Gln Lys Gly Met Gly Leu Leu
    210                 215                 220

Leu Leu Ile Leu Ala Thr Ala Leu Pro Asp Arg Phe Ala Thr Ala Leu
225                 230                 235                 240

Glu Gln His His Leu Pro Leu Gly Ile Lys Val Thr Val Ala Leu Ser
                245                 250                 255

Leu Ala Ile Gly Thr Leu Ile Gly Trp Gln Arg Ile Thr His Thr Leu
            260                 265                 270
```

Gly Glu Ala Met Gly Asp Arg Pro Leu Thr Thr Ala Gln Ser Leu Ser
            275                 280                 285

Ser Ala Ala Val Thr Thr Ala Thr Ile Leu Thr Ala Ser Arg Trp Gly
    290                 295                 300

Leu Pro Ile Ser Thr Thr Gln Val Leu Thr Ala Gly Ile Ala Gly Ser
305                 310                 315                 320

Thr Leu Ala Thr Gln Thr Ala Leu Asn Arg Gln Thr Ile Arg Arg Leu
                325                 330                 335

Leu Trp Thr Trp Leu Ile Thr Leu Pro Ile Ala Ile Gly Ser Ala Leu
            340                 345                 350

Leu Leu Tyr Ser Leu Gly Arg Ala Ile Trp Ala
            355                 360

<210> SEQ ID NO 3
<211> LENGTH: 5078
<212> TYPE: DNA
<213> ORGANISM: Synechococcus elongates PCC7942

<400> SEQUENCE: 3

```
atgacgaccc tcaagcctgc actgcgtcgt gctgctgtac tcctgccgat cgctgctgtc      60
gcttcgtccc ttttccctat ccaagaggca agcgctcagc gtgcactagt gactgctgac     120
ggttctagca ctgttttccc aatctccgaa gcagtggctg aagagttcca aaaacgcaat     180
aaaaacatca acgtcactgt cggcgtctct ggtactggtg gtggctttaa gcgtttctgc     240
aacggtgaaa ttgacatcgc caacgcttct cgccccatca agaaagaaga agttgaagct     300
tgccgtaaaa agggcattcg ctacatcgag ctgcccgtcg cttttgatgc gttgacggtt     360
gtagtcaaca gtccaatcc agtcaacagc atcaccactg ctgagttggc gaagatcttt     420
ggccgcgatg ccgagaaaaa aacaaccaac tggcgtcaag tcaaatccag cttccccaat     480
ctgcctttga gagtctacgc accgggtact gactcgggca cttacgatta cttcaacgag     540
gcaatcctca ataagaaagg aactcggggc gacctaactg ccagtgagga tgacaacatt     600
ctggtgcaag gggtgtcgcg cgatcgcggt ggtattggct tctttggttt ctcctactac     660
gaagagaaca aggtaagct caaagcactt gctgttgtta cagcaacgg caaggctgtg     720
atgccttctg tccaaaacgt gctgaatggc acttacgacc cgctggctcg ccctgtcttc     780
atctatgtca gcgagcaggc agccaaaaaa gcaaacgtca gatcgtttgt gaacttctac     840
ctgcagaatg caggcaagtt gtcgcgggaa gtaggatttg tgccgttgcc agccaaagct     900
tacaccgctg ccacccagcg cttcagaagc aacaaaactg gcacggtttt tgcaggcaag     960
agccttgtcg gtggttcgat cgaagaccta ctcaaagctg aaggcatcaa ctgaatcttg    1020
atgattccga tttagttgtt gaggctagta ggttgagaaa cttctcgatt tgctagcctt    1080
tcctctgtct agagaagtgc tgttcaactt attatcgaag cactttattt ctaaagttaa    1140
tgagaaaata ttgaggtaac aagatttatt taaagagtat tagagagtat taaaagtgtt    1200
gagttcttga ccttaaccgg atctttactt gggtaatgcg gaatccagct atgctttcct    1260
agtgtgagct ttaggtaatc aacggttaac gtcatggctt ccctaaaatt ccgactgctt    1320
ggccttgcaa cgctggcagt cttggcaact accgcttgca gctctggtga gcaacaatca    1380
agcgctggcg gtggttctgc cctcagcgga gacgtcaaag tcgacggctc cagcaccgtg    1440
tttccaatcg gggaagctat ggctgaagag ttccagaaaa gcaatggtga tgtgcgtgtc    1500
actgtaggag tttctggtac tggcggcggc ttcaaaaagt tctgtgctgg cgagacggat    1560
```

-continued

```
atctccaatg cttctcgccc catcaaatct tccgagatgg agctttgcca gaaaaatgga      1620
attgaatacg tcgagttgcc ggttgcctac gatgctctaa gtgttgttgt caacaacgaa      1680
aataactttg cgacctgctt gaccccggct caactcaaga cggcatggga tgaggccgca      1740
gaagggaaaa tttcgaattg gaatcagatc gatccgagct tccctgatac gccattggtt      1800
ctctatggcc ctggcactga ctctggtacc tacgactact tcaaagaagc cgtcatcggc      1860
gaagatggca ctcgcggcga cttcactgct tctgaagacg acaacatcat cgttcaaggg      1920
gtcgagcgga gtcccggtgc catgggcttc tttggtttgg cttacctcga agaaaatgct      1980
ggcaagctga aagccctcaa tatccaaaac tcgaaaggcg actgcgttgc ccccagtgtt      2040
gaaaccacgc gggatggtag ctacgagccc ctctcgcggc cgctctttgt ctacatcgcc      2100
aaatcggctc tagagaaacc ccaagtccaa gcatttgccg aatacttggt gaacccggcc      2160
aacggtaagc tggtagcaga agctggctac attcagttgc cagacgctct cttacccaag      2220
gtggttgatc gtctaaagaa tcaaactacc ggtaccgttt ttggtggcgg tagcgatgtg      2280
ggtgtcaacc ttgccgaaaa gctctaaata atgagccttg acgagaaagc tcgggttccc      2340
gagctttctc gtttggattg tgcgatcgct aaatcctttg ttcctctgac ttatgtctgc      2400
tgcggcccca ccctcaagag cctctttgtt caagcccaac cgtgagcgca accggcgcaa      2460
cgagttgatc gtcaaggcaa tctttggcat tttcgccttt gtctcagtct tgacgacatt      2520
gggcatcgtt ttcacgctga tctttgaaac ctacgagttt ttcaaagaaa ttccgctaat      2580
tcgttttctg acagaaaccc gctggacgcc tcttttccca agcgctcagt ttggaattgt      2640
agtgctccta tcaggaacct tctcgactac tctgattgct ctgctggtgg cagtccccct      2700
ggggctgctg agcgctatct gcctaagtga gtacgccaca cctcgggcac gaaacctgct      2760
caagccagcc ttagaagtga ttgctggtgt ccctagcgtt gtctttggct actttgctct      2820
tctctttgtg acgcccttgc tgcaatcctt tattcctggg ttgcaggggt ttaataccct      2880
ctccgctggg atggttttgg ggattgcaat caccccgctg gtcgcttcac tcagcgagga      2940
cgccattttt gcagtgccta gcagcatgcg cgaaggggcc tatgccttgg gtgcaacaaa      3000
gcgcgaaacc attgtctccg tcgttctacc tgctgctttg tcgggaattg tcgcctcgat      3060
tgtcttggcg atctcgcgcg ctgtcggtga acgatgatt gtggcgatcg cggcgggctt      3120
aaccccaaat ctaaccctca accccctaga accggcccag accatgacct cctttattgt      3180
gcaggtcagt ttgggagaca ccccaacagg ttcactggcc tacaaaacca ttttttgccgt      3240
ggggatgacc ctgttcttgc tgacgctcgt gctcaacatc tttagctact ggttcgtgcg      3300
tcgcttccag gagaaatacg aataatggct gccacagttc ccaaccaacc cgcagcagcg      3360
ccggctcgtc cctttcggcc tcgcctcgcc catcgttatc gtctcgacgc agtgatgatg      3420
acggctgctt ggacgggtgt tgcgatcgcg ctgctcgtct tgctggcgtt gatcagcgat      3480
gtcttccgca gcggcattcc ctacctcaat tgggatttct tgaccagctt cccctcgcgt      3540
cgccccagta gtgctgggat tctttccgct tgggtcggaa ccgtctactc gatcttttg      3600
gttggcttga ttggtttccc cttgggtgtg gtgcaggga tttacctcga ggagtttgcg      3660
ccagacaact ggtttacccg tctggtagaa atcaacgtca caatttggc tggcgttcct      3720
gccatcatct acggtctgct gggtctagag ctgtttgtgc ggattgcctc gccggttaca      3780
ggcggtcgca gcttgctatc gggttctttg acgctggcgc tgctgatcct tccgattgtg      3840
atcgtttcga ctcgggagtc actgcgggct gttcctgaca gtaccgtcta ggcaggcttt      3900
gcccttggtg ctacccgttg gcaagtcgtt cgtacgatca tcgtcccaga agcggcttcg      3960
```

```
gggatcttga ccggtacgat tctgggcatt tcccgtgcga tcggtgaagc agctcccctg    4020
attacgattg gggcgttgac cttcatttcc ttcctgcccg acaacctcca aagtcccttt    4080
accgtcctgc caattcaaat ctttaactgg gtctctcgtc cccaggctga gttccagaat    4140
ttggcggcgg ccgcgatcat cgtgttgcta gcgattttgc taaccatgaa ctcgatcgcg    4200
atcgtgattc gcaacaagtt gcaagtcaaa cgctaaagct gtctgttcca ctgcccctaa    4260
ttctgttgaa ttcttgctga cttatgagcc ccactgctgg tgagaacatt ctgctaaagg    4320
ccgaagccct ctcggtttat tacggcaatt cgcttgcggt caaagacgtc tacttggaag    4380
ttcccaagaa caagatcgtt gcctttatcg gtccatcggg ttgcggcaag agcactatcc    4440
ttcgctgctt taaccggatg aacgacctga tcaatggctg ccgtgttcag ggccgaatca    4500
ccttccacga tcaggaaatc aacgacggtc gtgtcgatgc tgtggaactg cgcagccgca    4560
tcggcatggt gttccagaaa cccaacccct tccccaagag catctacgaa aacatcgctt    4620
atggtgcccg gattaacggc taccaaggcg atatggatga gctggtcgaa aagtcgctgc    4680
gtcaagcggc actctgggat gaggtcaagg ataagctgaa agatagtggt cttgccctct    4740
cgggtggtca gcagcagcgg cttttgcattg ctcgtaccgt tgctgtgcag cctgaggtga    4800
tcttgatgga tgagccttgc tcggcactcg accccatctc gaccttggcg atcgaggagt    4860
tgatgcagac tctgaaagag cagtacacga tcatcatcgt gactcacaac atgcagcagg    4920
cttctcgaac ttcggactac accgcattct tcaatgcgcg ggcaaccgaa ggcggcggca    4980
agatgggcta cctggtggaa ttcgacacca ccgagaaaat ctttgatagc ccagaccaag    5040
aagcgacggc cgactacgtc agtggccgtt cggctaa                              5078

<210> SEQ ID NO 4
<211> LENGTH: 24
<212> TYPE: DNA
<213> ORGANISM: Artificial Sequence
<220> FEATURE:
<223> OTHER INFORMATION: Artificially Synthesized Sequence

<400> SEQUENCE: 4
acctgtcaga aattggcgat cgat                                             24

<210> SEQ ID NO 5
<211> LENGTH: 927
<212> TYPE: DNA
<213> ORGANISM: Artificial Sequence
<220> FEATURE:
<223> OTHER INFORMATION: Anabaena sp. 7120-HtxB

<400> SEQUENCE: 5
atggcgatcg caatcaaaaa acccttactg acatctgtgg ctgtagctgt gttggcactg     60
gttggctgtc aagcacccaa taacactact actaatggtt ctactgctcc taatgcaaag    120
agcgcagctg ctgaggttgt caatggtaaa cttcacctgc gttttgcaat tgcgccgatg    180
cgtccaacgc ctagccagac catcaaagag tttgagccga tattcaagta tctcgccgac    240
cagctcggcg cgacctatga aatcgtctcc ccggaaagct gggcggcaat atctgtggca    300
atgacaaatg gccatgtcga tgtgggctgg ctcggaccct ggggctatgt cttgtcgaat    360
aaaaaggccg gcaccgaagt gcttgcaacg gtcaagtacc gcggggagcc gttctacaaa    420
gccctcattg tcggtcgcgc cgatctgccg atcaaaaaat ggcccgagga cgcgaagggt    480
ttgaagctgt cactcagtga tcagggcaac acttctggct ggctcatccc gatggcgtac    540
```

```
ttcaagagca tcggcatcga ccctgcgagc tattttgaat atcgtgaagg tgccacgttt    600
ggccagaacg aatcacagat tcagcacgga ctgatcgacc tcggatccga tatggatcgg    660
ggccggaacg ggatgatcga agcgggtcaa atcgatcctt cgaagtccaa gatcgtgtgg    720
gaatccagca agctgccgaa cgacgcgata tccgtgccga aggattttga tcctgctctg    780
aaagcgcgca tcacggaaat actgacgtcc ttgtccgaag agaaagcaca gtcgctgatg    840
ggctcgggct ataacggctt cgtgaaggca agcacagcg attacaaggt aatcgaagac    900
gccggccgca tcctgggaaa actgtaa                                        927
```

<210> SEQ ID NO 6
<211> LENGTH: 308
<212> TYPE: PRT
<213> ORGANISM: Artificial Sequence
<220> FEATURE:
<223> OTHER INFORMATION: Anabaena sp. 7120-HtxB protein

<400> SEQUENCE: 6

```
Met Ala Ile Ala Ile Lys Lys Pro Leu Leu Thr Ser Val Ala Val
1               5                   10                  15

Val Leu Ala Leu Val Gly Cys Gln Ala Pro Asn Asn Thr Thr Thr Asn
            20                  25                  30

Gly Ser Thr Ala Pro Asn Ala Lys Ser Ala Ala Glu Val Val Asn
        35                  40                  45

Gly Lys Leu His Leu Arg Phe Ala Ile Ala Pro Met Arg Pro Thr Pro
    50                  55                  60

Ser Gln Thr Ile Lys Glu Phe Glu Pro Ile Phe Lys Tyr Leu Ala Asp
65                  70                  75                  80

Gln Leu Gly Ala Thr Tyr Glu Ile Val Ser Pro Glu Ser Trp Ala Ala
                85                  90                  95

Ile Ser Val Ala Met Thr Asn Gly His Val Asp Val Gly Trp Leu Gly
            100                 105                 110

Pro Trp Gly Tyr Val Leu Ser Asn Lys Lys Ala Gly Thr Glu Val Leu
        115                 120                 125

Ala Thr Val Lys Tyr Arg Gly Glu Pro Phe Tyr Lys Ala Leu Ile Val
    130                 135                 140

Gly Arg Ala Asp Leu Pro Ile Lys Lys Trp Pro Glu Asp Ala Lys Gly
145                 150                 155                 160

Leu Lys Leu Ser Leu Ser Asp Gln Gly Asn Thr Ser Gly Trp Leu Ile
                165                 170                 175

Pro Met Ala Tyr Phe Lys Ser Ile Gly Ile Asp Pro Ala Ser Tyr Phe
            180                 185                 190

Glu Tyr Arg Glu Gly Ala Thr Phe Gly Gln Asn Glu Ser Gln Ile Gln
        195                 200                 205

His Gly Leu Ile Asp Leu Gly Ser Asp Met Asp Arg Gly Arg Asn Gly
    210                 215                 220

Met Ile Glu Ala Gly Gln Ile Asp Pro Ser Lys Ser Lys Ile Val Trp
225                 230                 235                 240

Glu Ser Ser Lys Leu Pro Asn Asp Ala Ile Ser Val Pro Lys Asp Phe
                245                 250                 255

Asp Pro Ala Leu Lys Ala Arg Ile Thr Glu Ile Leu Thr Ser Leu Ser
            260                 265                 270

Glu Glu Lys Ala Gln Ser Leu Met Gly Ser Gly Tyr Asn Gly Phe Val
        275                 280                 285

Lys Ala Lys His Ser Asp Tyr Lys Val Ile Glu Asp Ala Gly Arg Ile
```

```
                    290                 295                 300

Leu Gly Lys Leu
305

<210> SEQ ID NO 7
<211> LENGTH: 849
<212> TYPE: DNA
<213> ORGANISM: Pseudomonas stutzeri WM88

<400> SEQUENCE: 7
atgaatcagc gaatcgaaga agtcatgctg gctaatgtca gagggacgt agccaggaga     60 aagcggcatt ttgcaacgtc ggtcgtagta ctcagtttgc tggcagtggc ctggtacgtg    120
tgtcagatag aattccagaa gctaggcgcc ggtttaccga gctatggtc attcgtcgtg    180 cagatgtttc cacccgacct gagcgacctg gacgtcattc taaaagggc tggcgagacg    240 ctcgccatgg cgacgattgg cacgatattc gccacaatca ttgcatttcc gctggcactc    300
atggctgcgc gtaatacctg tccgaacaag tggacctatc gggtatcccg cgccatcctg    360
aacgccagcc gcggcacgga gacatttgtc tatgcacttg tatttgtagc agcagtgggc    420
ttcggtccgt tctccggcgt actggccatt actttccaca tggtaggggc aatcggcaaa    480
atgtttgctg aagccatcga gcccgttgac caagggccgt ggatgcgct cgccttgacc    540 ggtgccagca gggcaaagat tatccgctac ggtctgatcc cggatgttat gccgcacctg    600
atcgcgagcg ttctatacat ttgggaattc agtgtcagaa cgtccacagt actgggcatc    660
gtaggcgcag gtggaattgg gcagaccctg aaagatactg tggacttgtt ggaattcaac    720
aagatgatta cggtactggc ggttgtattg ctgatggtgt cggcaatcga tttcatcagt    780
gaccggctca ggtacttgat attggacaca aaacgcgagg gattcgaaac tctccctgcg    840
aataactga                                                            849

<210> SEQ ID NO 8
<211> LENGTH: 282
<212> TYPE: PRT
<213> ORGANISM: Pseudomonas stutzeri WM88

<400> SEQUENCE: 8

Met Asn Gln Arg Ile Glu Glu Val Met Leu Ala Asn Val Lys Arg Asp
1               5                   10                  15

Val Ala Arg Arg Lys Arg His Phe Ala Thr Ser Val Val Leu Ser
                20                  25                  30

Leu Leu Ala Val Ala Trp Tyr Val Cys Gln Ile Glu Phe Gln Lys Leu
            35                  40                  45

Gly Ala Gly Leu Pro Arg Leu Trp Ser Phe Val Val Gln Met Phe Pro
        50                  55                  60

Pro Asp Leu Ser Asp Leu Asp Val Ile Leu Lys Gly Ala Gly Glu Thr
65                  70                  75                  80

Leu Ala Met Ala Thr Ile Gly Thr Ile Phe Ala Thr Ile Ile Ala Phe
                85                  90                  95

Pro Leu Ala Leu Met Ala Ala Arg Asn Thr Cys Pro Asn Lys Trp Thr
            100                 105                 110

Tyr Arg Val Ser Arg Ala Ile Leu Asn Ala Ser Arg Gly Thr Glu Thr
        115                 120                 125

Phe Val Tyr Ala Leu Val Phe Val Ala Ala Val Gly Phe Gly Pro Phe
    130                 135                 140

Ser Gly Val Leu Ala Ile Thr Phe His Met Val Gly Ala Ile Gly Lys
```

```
            145                 150                 155                 160
Met Phe Ala Glu Ala Ile Glu Pro Val Asp Gln Gly Pro Leu Asp Ala
                165                 170                 175

Leu Ala Leu Thr Gly Ala Ser Arg Ala Lys Ile Ile Arg Tyr Gly Leu
            180                 185                 190

Ile Pro Asp Val Met Pro His Leu Ile Ala Ser Val Leu Tyr Ile Trp
        195                 200                 205

Glu Phe Ser Val Arg Thr Ser Thr Val Leu Gly Ile Val Gly Ala Gly
    210                 215                 220

Gly Ile Gly Gln Thr Leu Lys Asp Thr Val Asp Leu Leu Glu Phe Asn
225                 230                 235                 240

Lys Met Ile Thr Val Leu Ala Val Leu Leu Met Val Ser Ala Ile
                245                 250                 255

Asp Phe Ile Ser Asp Arg Leu Arg Tyr Leu Ile Leu Asp Thr Lys Arg
            260                 265                 270

Glu Gly Phe Glu Thr Leu Pro Ala Asn Asn
                275                 280
```

<210> SEQ ID NO 9
<211> LENGTH: 813
<212> TYPE: DNA
<213> ORGANISM: Pseudomonas stutzeri WM88

<400> SEQUENCE: 9

```
atgaaagatg tagcgttgca gttaaagaat gtcggtaagt catacggcaa taaagttgtc    60
ctggaatcga ttgacttcga agtacgtcac ggctcaatgg ttgccttgct cggcacaagc   120
ggggcaggga agtcgacgct tttccgatgt ctcactggcc ttgagccgat tgactccggt   180
tctatcgtgg cgctcggaga atccatacat gaactgtctc cggcgcgtct gcgggcagta   240
cgtggccaga tcgggttcgt gttccaacaa ctgcacctgg tgaaaaggtt ctcagcactc   300
gagaatgtat gggtgcgcg tctggcagag atgcccattt ggcgcgtcac attgaaaagc   360
ttcagccggg ctgacaaagt gctcgcgttc gaatgtctgg accgggtcgg catgctcgat   420
tatgcaaaca cgcctacgca actgctgtca ggcggtcagc aacagcgtat tgcgatagcg   480
cgagccttgg cgcagaagcc caagattatt attgcggacg aacccgtctc cagcctcgat   540
ccgctgacgg cgcgctcggt tctgcaaacg ctgaaagccg cggctacaga tcttaatgtc   600
gcggtcctgt gcagcctgca ccaggtagac ctggcccgtg agtttggcga ccgcatcgtg   660
ggcatgcgcg acgacgtgt cgttttcgac ggcacgccag cggaattcac cgacgagcgc   720
gtgcatgcgc tttaccaggg tgcccgctgg gaagatgcac cagcggccga gagcgacgcg   780
cagcactcgg tggccggtct ggctgtggca tga                                813
```

<210> SEQ ID NO 10
<211> LENGTH: 270
<212> TYPE: PRT
<213> ORGANISM: Pseudomonas stutzeri WM88

<400> SEQUENCE: 10

```
Met Lys Asp Val Ala Leu Gln Leu Lys Asn Val Gly Lys Ser Tyr Gly
1               5                   10                  15

Asn Lys Val Val Leu Glu Ser Ile Asp Phe Glu Val Arg His Gly Ser
            20                  25                  30

Met Val Ala Leu Leu Gly Thr Ser Gly Ala Gly Lys Ser Thr Leu Phe
        35                  40                  45
```

```
Arg Cys Leu Thr Gly Leu Glu Pro Ile Asp Ser Gly Ser Ile Val Ala
        50                  55                  60

Leu Gly Glu Ser Ile His Glu Leu Ser Pro Ala Arg Leu Arg Ala Val
 65                  70                  75                  80

Arg Gly Gln Ile Gly Phe Val Phe Gln Leu His Leu Val Lys Arg
                 85                  90                  95

Phe Ser Ala Leu Glu Asn Val Leu Gly Ala Arg Leu Ala Glu Met Pro
            100                 105                 110

Ile Trp Arg Val Thr Leu Lys Ser Phe Ser Arg Ala Asp Lys Val Leu
        115                 120                 125

Ala Phe Glu Cys Leu Asp Arg Val Gly Met Leu Asp Tyr Ala Asn Thr
    130                 135                 140

Pro Thr Gln Leu Leu Ser Gly Gly Gln Gln Arg Ile Ala Ile Ala
145                 150                 155                 160

Arg Ala Leu Ala Gln Lys Pro Lys Ile Ile Ile Ala Asp Glu Pro Val
                165                 170                 175

Ser Ser Leu Asp Pro Leu Thr Ala Arg Ser Val Leu Gln Thr Leu Lys
            180                 185                 190

Ala Ala Ala Thr Asp Leu Asn Val Ala Val Leu Cys Ser Leu His Gln
        195                 200                 205

Val Asp Leu Ala Arg Glu Phe Gly Asp Arg Ile Val Gly Met Arg Asp
    210                 215                 220

Gly Arg Val Val Phe Asp Gly Thr Pro Ala Glu Phe Thr Asp Glu Arg
225                 230                 235                 240

Val His Ala Leu Tyr Gln Gly Ala Arg Trp Glu Asp Ala Pro Ala Ala
                245                 250                 255

Glu Ser Asp Ala Gln His Ser Val Ala Gly Leu Ala Val Ala
            260                 265                 270

<210> SEQ ID NO 11
<211> LENGTH: 300
<212> TYPE: DNA
<213> ORGANISM: Pseudomonas stutzeri WM88

<400> SEQUENCE: 11
atgtggccac cgccatcgc agaaaccgaa gaggtgggcc ggattcagga cctggatcgc      60
cagaagctgc ccctgttctc gcacatcgag acccaggagc gcgtcgagca aagatgaat    120 ctggacacgc tgaagatgga agccacgacg gaaaccgtcg aagtgctggt caagccggtc   180
ggctatgtct ggacggtttt catcaagatg atcgagaccc tggagattgc gctgtggggc   240
acgatcctgt cggtgctggt gtcgattccc ctggcgtatt tcgcggcccg caactactag   300

<210> SEQ ID NO 12
<211> LENGTH: 99
<212> TYPE: PRT
<213> ORGANISM: Pseudomonas stutzeri WM88

<400> SEQUENCE: 12

Met Trp Pro Pro Ala Ile Ala Glu Thr Glu Glu Val Gly Arg Ile Gln
  1               5                  10                  15

Asp Leu Asp Arg Gln Lys Leu Pro Leu Phe Ser His Ile Glu Thr Gln
                 20                  25                  30

Glu Arg Val Glu Gln Lys Met Asn Leu Asp Thr Leu Lys Met Glu Ala
             35                  40                  45

Thr Thr Glu Thr Val Glu Val Leu Val Lys Pro Val Gly Tyr Val Trp
        50                  55                  60
```

```
Thr Val Phe Ile Lys Met Ile Glu Thr Leu Glu Ile Ala Leu Trp Gly
 65                  70                  75                  80

Thr Ile Leu Ser Val Leu Val Ser Ile Pro Leu Ala Tyr Phe Ala Ala
                 85                  90                  95

Arg Asn Tyr

<210> SEQ ID NO 13
<211> LENGTH: 1011
<212> TYPE: DNA
<213> ORGANISM: Ralstonia sp. 4506

<400> SEQUENCE: 13
atgaagccca aagtcgtcct cacccactgg gtgcacccgg aaatcatcga attgttgtcc      60
gctagcgccg atgttatccc caacaccaca cgggaaacct tgccgcgttc tgaggtaatt     120
gcgcgagcca agatgcgga tgcactcatg gctttcatgc cggacagcat cgacagcgcg     180
tttctcgagg aatgtccaaa gctgcgtgtc atcggcgccg cgcttaaagg ctatgataac     240
ttcgatgtca acgcctgcac acgccacggt gtatggctta cgattgtgcc ggatttgctt     300
acgatcccga ccgctgaact gactatcggc cttcttctcg gtttgacaag gcatatgctg     360
gaaggcgata ggcaaatccg tagcggacac ttccaaggct ggcggccgac actatatggc     420
tctggtttga caggaaaaac gcttggcatc attggtatgg gggcggtcgg ccgtgcaatc     480
gcccagcgct tggctggctt tgaaatgaat ctcttgtatt gcgatccgat tccgctcaat     540
gccgaacaag aaaaggcttg gcacgtacag cgcgtcacgc tcgatgaact gctcgaaaaa     600
tgtgattatg tcgtgccgat ggttccgatg ccgcagaga cactgcatct gatcgatgcc      660
accgcgttgg ccaagatgaa aaccggtagc tacctgatca atgcatgtcg cggctcggtc     720
gtggatgaga atgcggtgat agcagcactg gcgtctggaa aactagctgg atatgcagcc     780
gatgtcttcg agatggaaga atggatacgc gctgatcgcc cgcaggctat ccccaaggcg     840
ctgctcgaca atacggcaca aacgtttttt acgccgcatt tgggatcggc ggtcaaggaa     900
gttcggcttg aaatcgagcg gcaggcagcg atgaacatca tccaggcact cgctggtgaa     960
aaaccgatgg gcgcgattaa tcagccgtat ccgggagtaa aggcggcgtg a            1011

<210> SEQ ID NO 14
<211> LENGTH: 336
<212> TYPE: PRT
<213> ORGANISM: Ralstonia sp. 4506

<400> SEQUENCE: 14

Met Lys Pro Lys Val Val Leu Thr His Trp Val His Pro Glu Ile Ile
  1               5                  10                  15

Glu Leu Leu Ser Ala Ser Ala Asp Val Ile Pro Asn Thr Thr Arg Glu
                 20                  25                  30

Thr Leu Pro Arg Ser Glu Val Ile Ala Arg Ala Lys Asp Ala Asp Ala
             35                  40                  45

Leu Met Ala Phe Met Pro Asp Ser Ile Asp Ser Ala Phe Leu Glu Glu
         50                  55                  60

Cys Pro Lys Leu Arg Val Ile Gly Ala Ala Leu Lys Gly Tyr Asp Asn
 65                  70                  75                  80

Phe Asp Val Asn Ala Cys Thr Arg His Gly Val Trp Leu Thr Ile Val
                 85                  90                  95

Pro Asp Leu Leu Thr Ile Pro Thr Ala Glu Leu Thr Ile Gly Leu Leu
                100                 105                 110
```

Leu Gly Leu Thr Arg His Met Leu Glu Gly Asp Arg Gln Ile Arg Ser
        115                 120                 125

Gly His Phe Gln Gly Trp Arg Pro Thr Leu Tyr Gly Ser Gly Leu Thr
    130                 135                 140

Gly Lys Thr Leu Gly Ile Ile Gly Met Gly Ala Val Gly Arg Ala Ile
145                 150                 155                 160

Ala Gln Arg Leu Ala Gly Phe Glu Met Asn Leu Leu Tyr Cys Asp Pro
                165                 170                 175

Ile Pro Leu Asn Ala Glu Gln Glu Lys Ala Trp His Val Gln Arg Val
            180                 185                 190

Thr Leu Asp Glu Leu Leu Glu Lys Cys Asp Tyr Val Val Pro Met Val
        195                 200                 205

Pro Met Ala Ala Glu Thr Leu His Leu Ile Asp Ala Thr Ala Leu Ala
    210                 215                 220

Lys Met Lys Thr Gly Ser Tyr Leu Ile Asn Ala Cys Arg Gly Ser Val
225                 230                 235                 240

Val Asp Glu Asn Ala Val Ile Ala Ala Leu Ala Ser Gly Lys Leu Ala
                245                 250                 255

Gly Tyr Ala Ala Asp Val Phe Glu Met Glu Glu Trp Ile Arg Ala Asp
            260                 265                 270

Arg Pro Gln Ala Ile Pro Lys Ala Leu Leu Asp Asn Thr Ala Gln Thr
        275                 280                 285

Phe Phe Thr Pro His Leu Gly Ser Ala Val Lys Glu Val Arg Leu Glu
    290                 295                 300

Ile Glu Arg Gln Ala Ala Met Asn Ile Ile Gln Ala Leu Ala Gly Glu
305                 310                 315                 320

Lys Pro Met Gly Ala Ile Asn Gln Pro Tyr Pro Gly Val Lys Ala Ala
                325                 330                 335

<210> SEQ ID NO 15
<211> LENGTH: 1014
<212> TYPE: DNA
<213> ORGANISM: Synechococcus elongates PCC7942

<400> SEQUENCE: 15

```
atgacgaccc tcaagcctgc actgcgtcgt gctgctgtac tcctgccgat cgctgctgtc      60
gcttcgtccc ttttccctat ccaagaggca agcgctcagc gtgcactagt gactgctgac     120
ggttctagca ctgttttccc aatctccgaa gcagtggctg aagagttcca aaaacgcaat     180
aaaaacatca acgtcactgt cggcgtctct ggtactggtg gtggctttaa gcgtttctgc     240
aacggtgaaa ttgacatcgc caacgcttct cgccccatca agaaagaaga gttgaagct     300
tgccgtaaaa agggcattcg ctacatcgag ctgcccgtcg cttttgatgc gttgacggtt     360
gtagtcaaca gtccaatcc agtcaacagc atcaccactg ctgagttggc gaagatcttt     420
ggccgcgatg ccgagaaaaa aacaaccaac tggcgtcaag tcaaatccag cttccccaat     480
ctgcctttga gagtctacgc accgggtact gactcgggca cttacgatta cttcaacgag     540
gcaatcctca ataagaaagg aactcggggc gacctaactg ccagtgagga tgacaacatt     600
ctggtgcaag gggtgtcgcg cgatcgcggt ggtattggct ctttggtttt ctcctactac     660
gaagagaaca aagtaagct caaagcactt gctgttgtta acagcaacgg caaggctgtg     720
atgccttctg tccaaaacgt gctgaatgga acttacgacc cgctggctcg ccctgtcttc     780
atctatgtca gcgagcaggc agccaaaaaa gcaaacgtca gatcgtttgt gaacttctac     840
```

```
ctgcagaatg caggcaagtt gtcgcgggaa gtaggatttg tgccgttgcc agccaaagct    900
tacaccgctg ccacccagcg cttcagaagc aacaaaactg gcacggtttt tgcaggcaag    960
agccttgtcg gtggttcgat cgaagaccta ctcaaagctg aaggcatcaa ctga          1014
```

<210> SEQ ID NO 16
<211> LENGTH: 337
<212> TYPE: PRT
<213> ORGANISM: Synechococcus elongates PCC7942

<400> SEQUENCE: 16

```
Met Thr Thr Leu Lys Pro Ala Leu Arg Arg Ala Ala Val Leu Leu Pro
1               5                   10                  15

Ile Ala Ala Val Ala Ser Ser Leu Phe Pro Ile Gln Glu Ala Ser Ala
                20                  25                  30

Gln Arg Ala Leu Val Thr Ala Asp Gly Ser Ser Thr Val Phe Pro Ile
            35                  40                  45

Ser Glu Ala Val Ala Glu Glu Phe Gln Lys Arg Asn Lys Asn Ile Asn
50                  55                  60

Val Thr Val Gly Val Ser Gly Thr Gly Gly Phe Lys Arg Phe Cys
65                  70                  75                  80

Asn Gly Glu Ile Asp Ile Ala Asn Ala Ser Arg Pro Ile Lys Lys Glu
                85                  90                  95

Glu Val Glu Ala Cys Arg Lys Lys Gly Ile Arg Tyr Ile Glu Leu Pro
            100                 105                 110

Val Ala Phe Asp Ala Leu Thr Val Val Asn Lys Ser Asn Pro Val
            115                 120                 125

Asn Ser Ile Thr Thr Ala Glu Leu Ala Lys Ile Phe Gly Arg Asp Ala
130                 135                 140

Glu Lys Lys Thr Thr Asn Trp Arg Gln Val Lys Ser Ser Phe Pro Asn
145                 150                 155                 160

Leu Pro Leu Arg Val Tyr Ala Pro Gly Thr Asp Ser Gly Thr Tyr Asp
                165                 170                 175

Tyr Phe Asn Glu Ala Ile Leu Asn Lys Lys Gly Thr Arg Gly Asp Leu
            180                 185                 190

Thr Ala Ser Glu Asp Asp Asn Ile Leu Val Gln Gly Val Ser Arg Asp
        195                 200                 205

Arg Gly Gly Ile Gly Phe Phe Gly Phe Ser Tyr Tyr Glu Glu Asn Lys
210                 215                 220

Gly Lys Leu Lys Ala Leu Ala Val Val Asn Ser Asn Gly Lys Ala Val
225                 230                 235                 240

Met Pro Ser Val Gln Asn Val Leu Asn Gly Thr Tyr Asp Pro Leu Ala
                245                 250                 255

Arg Pro Val Phe Ile Tyr Val Ser Glu Gln Ala Ala Lys Lys Ala Asn
            260                 265                 270

Val Arg Ser Phe Val Asn Phe Tyr Leu Gln Asn Ala Gly Lys Leu Ser
        275                 280                 285

Arg Glu Val Gly Phe Val Pro Leu Pro Ala Lys Ala Tyr Thr Ala Ala
    290                 295                 300

Thr Gln Arg Phe Arg Ser Asn Lys Thr Gly Thr Val Phe Ala Gly Lys
305                 310                 315                 320

Ser Leu Val Gly Gly Ser Ile Glu Asp Leu Leu Lys Ala Glu Gly Ile
                325                 330                 335

Asn
```

<210> SEQ ID NO 17
<211> LENGTH: 32
<212> TYPE: DNA
<213> ORGANISM: Artificial Sequence
<220> FEATURE:
<223> OTHER INFORMATION: Artificially Synthesized Sequence

<400> SEQUENCE: 17
cctaggagca tcaccatgaa aaaactcgca tc                              32

<210> SEQ ID NO 18
<211> LENGTH: 30
<212> TYPE: DNA
<213> ORGANISM: Artificial Sequence
<220> FEATURE:
<223> OTHER INFORMATION: Artificially Synthesized Sequence

<400> SEQUENCE: 18
attgacaacc tcagcggatg atgcatggcc                                 30

<210> SEQ ID NO 19
<211> LENGTH: 30
<212> TYPE: DNA
<213> ORGANISM: Artificial Sequence
<220> FEATURE:
<223> OTHER INFORMATION: Artificially Synthesized Sequence

<400> SEQUENCE: 19
cctaggagca tcaccatggc gatcgcaatc                                 30

<210> SEQ ID NO 20
<211> LENGTH: 30
<212> TYPE: DNA
<213> ORGANISM: Artificial Sequence
<220> FEATURE:
<223> OTHER INFORMATION: Artificially Synthesized Sequence

<400> SEQUENCE: 20
attgacaacc tcagcagctg cgctctttgc                                 30

<210> SEQ ID NO 21
<211> LENGTH: 34
<212> TYPE: DNA
<213> ORGANISM: Artificial Sequence
<220> FEATURE:
<223> OTHER INFORMATION: Artificially Synthesized Sequence

<400> SEQUENCE: 21
cctaggagca tcaccatggc ttccctaaaa ttcc                            34

<210> SEQ ID NO 22
<211> LENGTH: 30
<212> TYPE: DNA
<213> ORGANISM: Artificial Sequence
<220> FEATURE:
<223> OTHER INFORMATION: Artificially Synthesized Sequence

<400> SEQUENCE: 22
attgacaacc tcagcaccag agctgcaagc                                 30

<210> SEQ ID NO 23
<211> LENGTH: 41
<212> TYPE: DNA
<213> ORGANISM: Artificial Sequence
<220> FEATURE:
<223> OTHER INFORMATION: Artificially Synthesized Sequence

<400> SEQUENCE: 23
acagaccatg gaattcgtgt catatcacga cattaccatc g                41

<210> SEQ ID NO 24
<211> LENGTH: 41
<212> TYPE: DNA
<213> ORGANISM: Artificial Sequence
<220> FEATURE:
<223> OTHER INFORMATION: Artificially Synthesized Sequence

<400> SEQUENCE: 24
caaaacagcc aagctttcac gccgccttta ctcccggata c                41

<210> SEQ ID NO 25
<211> LENGTH: 36
<212> TYPE: DNA
<213> ORGANISM: Artificial Sequence
<220> FEATURE:
<223> OTHER INFORMATION: Artificially Synthesized Sequence

<400> SEQUENCE: 25
acagaccatg gaattcatgc aagtttttac tctgtt                      36

<210> SEQ ID NO 26
<211> LENGTH: 35
<212> TYPE: DNA
<213> ORGANISM: Artificial Sequence
<220> FEATURE:
<223> OTHER INFORMATION: Artificially Synthesized Sequence

<400> SEQUENCE: 26
agctgaaggc gtcgactagt agttgcgggc cgcga                       35

<210> SEQ ID NO 27
<211> LENGTH: 25
<212> TYPE: DNA
<213> ORGANISM: Artificial Sequence
<220> FEATURE:
<223> OTHER INFORMATION: Artificially Synthesized Sequence

<400> SEQUENCE: 27
catggtgatg ctcctaggat ccccg                                  25

<210> SEQ ID NO 28
<211> LENGTH: 25
<212> TYPE: DNA
<213> ORGANISM: Artificial Sequence
<220> FEATURE:
<223> OTHER INFORMATION: Artificially Synthesized Sequence

<400> SEQUENCE: 28
gctgaggttg tcaatggtaa acttc                                  25

<210> SEQ ID NO 29
<211> LENGTH: 798
<212> TYPE: DNA
<213> ORGANISM: Artificial Sequence
<220> FEATURE:
<223> OTHER INFORMATION: Gentamicin resistant gene

<400> SEQUENCE: 29
ttgccgggtg acgcacaccg tggaaacgga tgaaggcacg aacccagttg acataagcct   60
gttcggttcg taaactgtaa tgcaagtagc gtatgcgctc acgcaactgg tccagaacct  120

```
tgaccgaacg cagcggtggt aacggcgcag tggcggtttt catggcttgt tatgactgtt    180
tttttgtaca gtctatgcct cgggcatcca agcagcaagc gcgttacgcc gtgggtcgat    240
gtttgatgtt atggagcagc aacgatgtta cgcagcagca acgatgttac gcagcagggc    300
agtcgcccta aaacaaagtt aggtggctca agtatgggca tcattcgcac atgtaggctc    360
ggccctgacc aagtcaaatc catgagggct gctcttgatc ttttcggtcg tgagttcgga    420
gacgtagcca cctactccca acatcagccg gactccgatt acctcgggaa cttgctccgt    480
agtaagacat tcatcgcgct tgctgccttc gaccaagaag cggttgttgg cgctctcgcg    540
gcttacgttc tgccaaagtt tgagcaggcg cgtagtgaga tctatatcta tgatctcgca    600
gtctccggcg agcaccggag gcaaggcatt gccaccgcgc tcatcaatct cctcaagcat    660
gaggccaacg cgcttggtgc ttatgtgatc tacgtgcaag cagattacgg tgacgatccc    720
gcagtggctc tctatacaaa gttgggcata cgggaagaag tgatgcactt tgatatcgac    780
ccaagtaccg ccacctaa                                                  798

<210> SEQ ID NO 30
<211> LENGTH: 1019
<212> TYPE: DNA
<213> ORGANISM: Artificial Sequence
<220> FEATURE:
<223> OTHER INFORMATION: Kanamycin resistant gene

<400> SEQUENCE: 30
gtggaattgt gagcggataa caatttcaca caggaaacag ctatgaccat gattacgaat     60
tccccggatc cgtcgacctg cagggggggg ggggaaagcc acgttgtgtc tcaaaatctc    120
tgatgttaca ttgcacaaga taaaaatata tcatcatgaa caataaaact gtctgcttac    180
ataaacagta atacaagggg tgttatgagc catattcaac gggaaacgtc ttgctcgagg    240
ccgcgattaa attccaacat ggatgctgat ttatatgggt ataaatgggc tcgcgataat    300
gtcgggcaat caggtgcgac aatctatcga ttgtatggga agcccgatgc gccagagttg    360
tttctgaaac atggcaaagg tagcgttgcc aatgatgtta cagatgagat ggtcagacta    420
aactggctga cggaatttat gcctcttccg accatcaagc attttatccg tactcctgat    480
gatgcatggt tactcaccac tgcgatcccc gggaaaacag cattccaggt attagaagaa    540
tatcctgatt caggtgaaaa tattgttgat gcgctggcag tgttcctgcg ccggttgcat    600
tcgattcctg tttgtaattg tccttttaac agcgatcgcg tatttcgtct cgctcaggcg    660
caatcacgaa tgaataacgg tttggttgat gcgagtgatt ttgatgacga gcgtaatggc    720
tggcctgttg aacaagtctg gaaagaaatg cataagcttt tgccattctc accggattca    780
gtcgtcactc atggtgattt ctcacttgat aaccttattt ttgacgaggg gaaattaata    840
ggttgtattg atgttggacg agtcggaatc gcagaccgat accaggatct tgccatccta    900
tggaactgcc tcggtgagtt ttctccttca ttacagaaac ggcttttttca aaaatatggt    960 attgataatc ctgatatgaa taaattgcag tttcatttga tgctcgatga gttttttcta   1019

<210> SEQ ID NO 31
<211> LENGTH: 861
<212> TYPE: DNA
<213> ORGANISM: Ralstonia sp. 4506

<400> SEQUENCE: 31
atgaaaaaac tcgcatccgc attattgtct gtcttgcttg ccgccgtctg cagcattggc     60
catgcatcat ccaatcccga tccagaaacg ctcaaagttg cgctgctgcc ggacgaaaac    120
```

```
gcatcgaccg taattaaaaa caacaagccg ctcgaaatct atctggaaaa agagctggga    180
aagaaaattg agctggtggt taccactgat tactcgtcaa tgatcgaagc catgcgtcac    240
ggccgtatcg acatggcata ttttggcccc ttgtcgtatg tgctggctaa gcaaagagc    300 gacatcgagc cattcgcagc gatgaagcaa aagggtagca ctacctacca gtccgtattg    360
atcgccaata ctggcgccgg catcgccaaa atcagtgata tcgtcaacaa gaatgtcgct    420
tacggtgata aggcatccac ctccagccat ttgattccga agtcgatatt ggcggaaaac    480
ggtttgaaag ccggcgaaaa ctatcgcgaa cactttgtcg gtgcgcatga cgcggtggcc    540
atggccgtgc aaaacggtca cgcgcaggct ggcggcttga gtaagccgat ttttgaatcc    600
ctggttcagc gcggactggt cgatcccaac aaagtaaaag ttcttgccga atcgaagcca    660
tatccgcaat acccgtggac catgcgcagc aatctgaagc cggaactgaa ggaaaagatc    720
cgtgcagcct tcttgaatct caaagatccg gaagtcctga aacctttcaa agccgatggt    780
ttcggcccga tcagcgacaa agactatgac gtggtgcgca gccttggcac actgctcaag    840
ctcgatctgt cgaagttcta a                                             861
```

<210> SEQ ID NO 32
<211> LENGTH: 286
<212> TYPE: PRT
<213> ORGANISM: Ralstonia sp. 4506

<400> SEQUENCE: 32

```
Met Lys Lys Leu Ala Ser Ala Leu Leu Ser Val Leu Leu Ala Ala Val
1               5                   10                  15

Cys Ser Ile Gly His Ala Ser Ser Asn Pro Asp Pro Glu Thr Leu Lys
                20                  25                  30

Val Ala Leu Leu Pro Asp Glu Asn Ala Ser Thr Val Ile Lys Asn Asn
            35                  40                  45

Lys Pro Leu Glu Ile Tyr Leu Glu Lys Glu Leu Gly Lys Lys Ile Glu
        50                  55                  60

Leu Val Val Thr Thr Asp Tyr Ser Ser Met Ile Glu Ala Met Arg His
65                  70                  75                  80

Gly Arg Ile Asp Met Ala Tyr Phe Gly Pro Leu Ser Tyr Val Leu Ala
                85                  90                  95

Lys Gln Lys Ser Asp Ile Glu Pro Phe Ala Ala Met Lys Gln Lys Gly
            100                 105                 110

Ser Thr Thr Tyr Gln Ser Val Leu Ile Ala Asn Thr Gly Ala Gly Ile
        115                 120                 125

Ala Lys Ile Ser Asp Ile Val Asn Lys Asn Val Ala Tyr Gly Asp Lys
    130                 135                 140

Ala Ser Thr Ser Ser His Leu Ile Pro Lys Ser Ile Leu Ala Glu Asn
145                 150                 155                 160

Gly Leu Lys Ala Gly Glu Asn Tyr Arg Glu His Phe Val Gly Ala His
                165                 170                 175

Asp Ala Val Ala Met Ala Val Gln Asn Gly His Ala Gln Ala Gly Gly
            180                 185                 190

Leu Ser Lys Pro Ile Phe Glu Ser Leu Val Gln Arg Gly Leu Val Asp
        195                 200                 205

Pro Asn Lys Val Lys Val Leu Ala Glu Ser Lys Pro Tyr Pro Gln Tyr
    210                 215                 220

Pro Trp Thr Met Arg Ser Asn Leu Lys Pro Glu Leu Lys Glu Lys Ile
225                 230                 235                 240
```

Arg Ala Ala Phe Leu Asn Leu Lys Asp Pro Glu Val Leu Lys Pro Phe
              245                 250                 255

Lys Ala Asp Gly Phe Gly Pro Ile Ser Asp Lys Asp Tyr Asp Val Val
          260                 265                 270

Arg Ser Leu Gly Thr Leu Leu Lys Leu Asp Leu Ser Lys Phe
          275                 280                 285

<210> SEQ ID NO 33
<211> LENGTH: 1014
<212> TYPE: DNA
<213> ORGANISM: Synechococcus elongates PCC7942

<400> SEQUENCE: 33

| | | | | | |
|---|---|---|---|---|---|
| atggcttccc | taaaattccg | actgcttggc | cttgcaacgc | tggcagtctt | ggcaactacc | 60 |
| gcttgcagct | ctggtgagca | acaatcaagc | gctggcggtg | ttctgccct | cagcggagac | 120 |
| gtcaaagtcg | acggctccag | caccgtgttt | ccaatcgggg | aagctatggc | tgaagagttc | 180 |
| cagaaaagca | atggtgatgt | gcgtgtcact | gtaggagttt | ctggtactgg | cggcggcttc | 240 |
| aaaaagttct | gtgctggcga | gacggatatc | tccaatgctt | ctcgccccat | caaatcttcc | 300 |
| gagatggagc | tttgccagaa | aaatggaatt | gaatacgtcg | agttgccggt | tgcctacgat | 360 |
| gctctaagtg | ttgttgtcaa | caacgaaaat | aactttgcga | cctgcttgac | cccggctcaa | 420 |
| ctcaagacgg | catgggatga | ggccgcagaa | gggaaaattt | cgaattggaa | tcagatcgat | 480 |
| ccgagcttcc | ctgatacgcc | attggttctc | tatggccctg | gcactgactc | tggtacctac | 540 |
| gactacttca | agaagccgt | catcggcgaa | gatggcactc | gcggcgactt | cactgcttct | 600 |
| gaagacgaca | acatcatcgt | tcaaggggtc | gagcggagtc | ccggtgccat | gggcttcttt | 660 |
| ggtttggctt | acctcgaaga | aaatgctggc | aagctgaaag | ccctcaatat | ccaaaactcg | 720 |
| aaaggcgact | gcgttgcccc | cagtgttgaa | accacgcggg | atggtagcta | cgagcccctc | 780 |
| tcgcggccgc | tctttgtcta | catcgccaaa | tcggctctag | agaaaccca | agtccaagca | 840 |
| tttgccgaat | acttggtgaa | cccggccaac | ggtaagctgg | tagcagaagc | tggctacatt | 900 |
| cagttgccag | acgctctctt | acccaaggtg | gttgatcgtc | taaagaatca | aactaccggt | 960 |
| accgtttttg | gtggcggtag | cgatgtgggt | gtcaaccttg | ccgaaaagct | ctaa | 1014 |

<210> SEQ ID NO 34
<211> LENGTH: 337
<212> TYPE: PRT
<213> ORGANISM: Synechococcus elongates PCC7942

<400> SEQUENCE: 34

Met Ala Ser Leu Lys Phe Arg Leu Leu Gly Leu Ala Thr Leu Ala Val
1               5                   10                  15

Leu Ala Thr Thr Ala Cys Ser Ser Gly Glu Gln Gln Ser Ser Ala Gly
            20                  25                  30

Gly Gly Ser Ala Leu Ser Gly Asp Val Lys Val Asp Gly Ser Ser Thr
        35                  40                  45

Val Phe Pro Ile Gly Glu Ala Met Ala Glu Glu Phe Gln Lys Ser Asn
    50                  55                  60

Gly Asp Val Arg Val Thr Val Gly Val Ser Thr Gly Gly Gly Phe
65                  70                  75                  80

Lys Lys Phe Cys Ala Gly Glu Thr Asp Ile Ser Asn Ala Ser Arg Pro
                85                  90                  95

Ile Lys Ser Ser Glu Met Glu Leu Cys Gln Lys Asn Gly Ile Glu Tyr

|     | 100 |     |     |     | 105 |     |     |     | 110 |     |     |
|-----|-----|-----|-----|-----|-----|-----|-----|-----|-----|-----|-----|

Val Glu Leu Pro Val Ala Tyr Asp Ala Leu Ser Val Val Asn Asn
        115              120             125

Glu Asn Asn Phe Ala Thr Cys Leu Thr Pro Ala Gln Leu Lys Thr Ala
130             135             140

Trp Asp Glu Ala Ala Glu Gly Lys Ile Ser Asn Trp Asn Gln Ile Asp
145            150             155             160

Pro Ser Phe Pro Asp Thr Pro Leu Val Leu Tyr Gly Pro Gly Thr Asp
             165             170            175

Ser Gly Thr Tyr Asp Tyr Phe Lys Glu Ala Val Ile Gly Glu Asp Gly
        180             185            190

Thr Arg Gly Asp Phe Thr Ala Ser Glu Asp Asn Ile Ile Val Gln
        195             200            205

Gly Val Glu Arg Ser Pro Gly Ala Met Gly Phe Phe Gly Leu Ala Tyr
        210             215            220

Leu Glu Glu Asn Ala Gly Lys Leu Lys Ala Leu Asn Ile Gln Asn Ser
225             230            235             240

Lys Gly Asp Cys Val Ala Pro Ser Val Glu Thr Arg Asp Gly Ser
            245             250            255

Tyr Glu Pro Leu Ser Arg Pro Leu Phe Val Tyr Ile Ala Lys Ser Ala
        260             265            270

Leu Glu Lys Pro Gln Val Gln Ala Phe Ala Glu Tyr Leu Val Asn Pro
        275             280            285

Ala Asn Gly Lys Leu Val Ala Glu Ala Gly Tyr Ile Gln Leu Pro Asp
        290             295            300

Ala Leu Leu Pro Lys Val Val Asp Arg Leu Lys Asn Gln Thr Thr Gly
305             310            315             320

Thr Val Phe Gly Gly Ser Asp Val Gly Val Asn Leu Ala Glu Lys
            325             330            335

Leu

<210> SEQ ID NO 35
<211> LENGTH: 939
<212> TYPE: DNA
<213> ORGANISM: Anabaena sp. 7120

<400> SEQUENCE: 35

```
atggcgatcg caatcaaaaa acccttactg acatctgtgg ctgtagctgt gttggcactg      60
gttggctgtc aagcacccaa taacactact actaatggtt ctactgctcc taatgcaaag     120
agcgcagctg caattgatcc tagtgtctct gaccccaaaa ccttaaaagt agctcttta     180
cctgatgaaa atgcttccac gattatcaga ataatcaag gtctagaaaa atatttggaa     240
gaaaaagtgg gcaaagatgt ggaattagtc gtcactacag actattcttc gatgattgaa     300
gcagcaagta acggacgctt agatttagca tattttggtc cactttccta tgttttggct     360
aagactaaaa gtaatattga acccttgcg gcattaagga agatggtga aaccacatat     420
aaatctgtaa ttattgctaa tactaatagc ggtgtcaatt ccattgagca agcagcagga     480
aaaacagtag catttggtga tcaagcttct acttccagtc atttaatccc caaatccatg     540
cttgccgaaa agggtttgca agccaaaaca aattatcaag aagttttgc tggatctcat     600
gatgcggttg ctttagcagt tcagaacaac aatgctcagg ttggtggatt gagtcaacct     660
attttttgcat ctctaattga gcgcaaaata attgatagta acaaagtcaa agttttagca     720
gagtcgaaac catttcctca atatccttgg acaatgcgct ctgatttaaa ccctgaacta     780
```

```
aaagcaaaaa ttcgtgcggc gtttattgaa atgaatgata aagcaatcct caagccttt    840 aaagctgatg gatttaatgc cattgaagat aaaaattatg acgtagtgcg tgatttaggg    900
aaaattttga atctcgattt tgagaagttg aataaataa                           939
```

<210> SEQ ID NO 36
<211> LENGTH: 312
<212> TYPE: PRT
<213> ORGANISM: Anabaena sp. 7120

<400> SEQUENCE: 36

```
Met Ala Ile Ala Ile Lys Lys Pro Leu Leu Thr Ser Val Ala Val Ala
 1               5                  10                  15

Val Leu Ala Leu Val Gly Cys Gln Ala Pro Asn Asn Thr Thr Thr Asn
            20                  25                  30

Gly Ser Thr Ala Pro Asn Ala Lys Ser Ala Ala Ala Ile Asp Pro Ser
        35                  40                  45

Val Ser Asp Pro Lys Thr Leu Lys Val Ala Leu Leu Pro Asp Glu Asn
    50                  55                  60

Ala Ser Thr Ile Ile Arg Asn Asn Gln Gly Leu Glu Lys Tyr Leu Glu
65                  70                  75                  80

Glu Lys Val Gly Lys Asp Val Glu Leu Val Val Thr Thr Asp Tyr Ser
                85                  90                  95

Ser Met Ile Glu Ala Ala Ser Asn Gly Arg Leu Asp Leu Ala Tyr Phe
            100                 105                 110

Gly Pro Leu Ser Tyr Val Leu Ala Lys Thr Lys Ser Asn Ile Glu Pro
        115                 120                 125

Phe Ala Ala Leu Arg Lys Asp Gly Glu Thr Thr Tyr Lys Ser Val Ile
    130                 135                 140

Ile Ala Asn Thr Asn Ser Gly Val Asn Ser Ile Glu Gln Ala Ala Gly
145                 150                 155                 160

Lys Thr Val Ala Phe Gly Asp Gln Ala Ser Thr Ser Ser His Leu Ile
                165                 170                 175

Pro Lys Ser Met Leu Ala Glu Lys Gly Leu Gln Ala Lys Thr Asn Tyr
            180                 185                 190

Gln Glu Val Phe Ala Gly Ser His Asp Ala Val Ala Leu Ala Val Gln
        195                 200                 205

Asn Asn Asn Ala Gln Val Gly Gly Leu Ser Gln Pro Ile Phe Ala Ser
    210                 215                 220

Leu Ile Glu Arg Lys Ile Ile Asp Ser Asn Lys Val Lys Val Leu Ala
225                 230                 235                 240

Glu Ser Lys Pro Phe Pro Gln Tyr Pro Trp Thr Met Arg Ser Asp Leu
                245                 250                 255

Asn Pro Glu Leu Lys Ala Lys Ile Arg Ala Ala Phe Ile Glu Met Asn
            260                 265                 270

Asp Lys Ala Ile Leu Lys Pro Phe Lys Ala Asp Gly Phe Asn Ala Ile
        275                 280                 285

Glu Asp Lys Asn Tyr Asp Val Val Arg Asp Leu Gly Lys Ile Leu Asn
    290                 295                 300

Leu Asp Phe Glu Lys Leu Asn Lys
305                 310
```

<210> SEQ ID NO 37
<211> LENGTH: 310
<212> TYPE: PRT

<213> ORGANISM: Synechococcus elongates PCC7942

<400> SEQUENCE: 37

```
Met Ser Ala Ala Ala Pro Pro Ser Arg Ala Ser Leu Phe Lys Pro Asn
1               5                   10                  15
Arg Glu Arg Asn Arg Arg Asn Glu Leu Ile Val Lys Ala Ile Phe Gly
            20                  25                  30
Ile Phe Ala Phe Val Ser Val Leu Thr Thr Leu Gly Ile Val Phe Thr
        35                  40                  45
Leu Ile Phe Glu Thr Tyr Glu Phe Phe Lys Glu Ile Pro Leu Ile Arg
    50                  55                  60
Phe Leu Thr Glu Thr Arg Trp Thr Pro Leu Phe Pro Ser Ala Gln Phe
65                  70                  75                  80
Gly Ile Val Val Leu Leu Ser Gly Thr Phe Ser Thr Thr Leu Ile Ala
                85                  90                  95
Leu Leu Val Ala Val Pro Leu Gly Leu Leu Ser Ala Ile Cys Leu Ser
            100                 105                 110
Glu Tyr Ala Thr Pro Arg Ala Arg Asn Leu Leu Lys Pro Ala Leu Glu
        115                 120                 125
Val Ile Ala Gly Val Pro Ser Val Val Phe Gly Tyr Phe Ala Leu Leu
    130                 135                 140
Phe Val Thr Pro Leu Leu Gln Ser Phe Ile Pro Gly Leu Gln Gly Phe
145                 150                 155                 160
Asn Thr Leu Ser Ala Gly Met Val Leu Gly Ile Ala Ile Thr Pro Leu
                165                 170                 175
Val Ala Ser Leu Ser Glu Asp Ala Ile Phe Ala Val Pro Ser Ser Met
            180                 185                 190
Arg Glu Gly Ala Tyr Ala Leu Gly Ala Thr Lys Arg Glu Thr Ile Val
        195                 200                 205
Ser Val Val Leu Pro Ala Ala Leu Ser Gly Ile Val Ala Ser Ile Val
    210                 215                 220
Leu Ala Ile Ser Arg Ala Val Gly Glu Thr Met Ile Val Ala Ile Ala
225                 230                 235                 240
Ala Gly Leu Thr Pro Asn Leu Thr Leu Asn Pro Leu Glu Pro Ala Gln
                245                 250                 255
Thr Met Thr Ser Phe Ile Val Gln Val Ser Leu Gly Asp Thr Pro Thr
            260                 265                 270
Gly Ser Leu Ala Tyr Lys Thr Ile Phe Ala Val Gly Met Thr Leu Phe
        275                 280                 285
Leu Leu Thr Leu Val Leu Asn Ile Phe Ser Tyr Trp Phe Val Arg Arg
    290                 295                 300
Phe Gln Glu Lys Tyr Glu
305                 310
```

<210> SEQ ID NO 38
<211> LENGTH: 933
<212> TYPE: DNA
<213> ORGANISM: Synechococcus elongates PCC7942

<400> SEQUENCE: 38

```
atgtctgctg cggccccacc ctcaagagcc tctttgttca agcccaaccg tgagcgcaac    60
cggcgcaacg agttgatcgt caaggcaatc tttggcattt tcgcctttgt ctcagtcttg   120
acgacattgg gcatcgtttt cacgctgatc tttgaaacct acgagttttt caaagaaatt   180
ccgctaattc gttttctgac agaaacccgc tggacgcctc ttttcccaag cgctcagttt   240
```

```
ggaattgtag tgctcctatc aggaaccttc tcgactactc tgattgctct gctggtggca    300
gtccccttgg ggctgctgag cgctatctgc ctaagtgagt acgccacacc tcgggcacga    360
aacctgctca agccagcctt agaagtgatt gctggtgtcc ctagcgttgt ctttggctac    420
tttgctcttc tctttgtgac gcccttgctg caatccttta ttcctgggtt gcaggggttt    480
aataccctct ccgctgggat ggttttgggg attgcaatca ccccgctggt cgcttcactc    540
agcgaggacg ccattttgc agtgcctagc agcatgcgcg aagggcta tgccttgggt     600 gcaacaaagc gcgaaaccat tgtctccgtc gttctacctg ctgctttgtc gggaattgtc    660
gcctcgattg tcttggcgat ctcgcgcgct gtcggtgaga cgatgattgt ggcgatcgcg    720
gcgggcttaa ccccaaatct aaccctcaac cccctagaac cggcccagac catgacctcc    780
tttattgtgc aggtcagttt gggagacacc ccaacaggtt cactggccta caaaaccatt    840
tttgccgtgg ggatgaccct gttcttgctg acgctcgtgc tcaacatctt tagctactgg    900
ttcgtgcgtc gcttccagga gaaatacgaa taa                                933
```

<210> SEQ ID NO 39
<211> LENGTH: 303
<212> TYPE: PRT
<213> ORGANISM: Synechococcus elongates PCC7942

<400> SEQUENCE: 39

```
Met Ala Ala Thr Val Pro Asn Gln Pro Ala Ala Ala Pro Ala Arg Pro
 1               5                  10                  15

Phe Arg Pro Arg Leu Ala His Arg Tyr Arg Leu Asp Ala Val Met Met
            20                  25                  30

Thr Ala Ala Trp Thr Gly Val Ala Ile Ala Leu Leu Val Leu Leu Ala
        35                  40                  45

Leu Ile Ser Asp Val Phe Arg Ser Gly Ile Pro Tyr Leu Asn Trp Asp
    50                  55                  60

Phe Leu Thr Ser Phe Pro Ser Arg Pro Ser Ser Ala Gly Ile Leu
65                  70                  75                  80

Ser Ala Trp Val Gly Thr Val Tyr Ser Ile Phe Leu Val Gly Leu Ile
                85                  90                  95

Gly Phe Pro Leu Gly Val Gly Ala Gly Ile Tyr Leu Glu Glu Phe Ala
            100                 105                 110

Pro Asp Asn Trp Phe Thr Arg Leu Val Glu Ile Asn Val Asn Asn Leu
        115                 120                 125

Ala Gly Val Pro Ala Ile Ile Tyr Gly Leu Leu Gly Leu Glu Leu Phe
    130                 135                 140

Val Arg Ile Ala Ser Pro Val Thr Gly Gly Arg Ser Leu Leu Ser Gly
145                 150                 155                 160

Ser Leu Thr Leu Ala Leu Leu Ile Leu Pro Ile Val Ile Val Ser Thr
                165                 170                 175

Arg Glu Ser Leu Arg Ala Val Pro Asp Ser Thr Arg Gln Ala Gly Phe
            180                 185                 190

Ala Leu Gly Ala Thr Arg Trp Gln Val Val Arg Thr Ile Ile Val Pro
        195                 200                 205

Glu Ala Ala Ser Gly Ile Leu Thr Gly Thr Ile Leu Gly Ile Ser Arg
    210                 215                 220

Ala Ile Gly Glu Ala Ala Pro Leu Ile Thr Ile Gly Ala Leu Thr Phe
225                 230                 235                 240

Ile Ser Phe Leu Pro Asp Asn Leu Gln Ser Pro Phe Thr Val Leu Pro
```

```
                245                 250                 255
Ile Gln Ile Phe Asn Trp Val Ser Arg Pro Gln Ala Glu Phe Gln Asn
            260                 265                 270

Leu Ala Ala Ala Ile Ile Val Leu Leu Ala Ile Leu Leu Thr Met
        275                 280                 285

Asn Ser Ile Ala Ile Val Ile Arg Asn Lys Leu Gln Val Lys Arg
        290                 295                 300

<210> SEQ ID NO 40
<211> LENGTH: 912
<212> TYPE: DNA
<213> ORGANISM: Synechococcus elongates PCC7942

<400> SEQUENCE: 40
atggctgcca cagttcccaa ccaacccgca gcagcgccgg ctcgtccctt cggcctcgc      60
ctcgcccatc gttatcgtct cgacgcagtg atgatgacgg ctgcttggac gggtgttgcg    120
atcgcgctgc tcgtcttgct ggcgttgatc agcgatgtct ccgcagcgg cattccctac    180
ctcaattggg atttcttgac cagcttcccc tcgcgtcgcc ccagtagtgc tgggattctt    240
tccgcttggg tcggaaccgt ctactcgatc tttttggttg gcttgattgg tttccccttg    300
ggtgtgggtg cagggattta cctcgaggag tttgcgccag acaactggtt tacccgtctg    360
gtagaaatca cgtcaacaa tttggctggc gttcctgcca tcatctacgg tctgctgggt    420
ctagagctgt ttgtgcggat tgcctcgccg gttacaggcg gtcgcagctt gctatcgggt    480
tctttgacgc tggcgctgct gatccttccg attgtgatcg tttcgactcg ggagtcactg    540
cgggctgttc ctgacagtac ccgtcaggca ggctttgccc ttggtgctac ccgttggcaa    600
gtcgttcgta cgatcatcgt cccagaagcg gcttcgggga tcttgaccgg tacgattctg    660
ggcatttccc gtgcgatcgg tgaagcagct cccctgatta cgattggggc gttgaccttc    720
atttccttcc tgcccgacaa cctccaaagt cccttaccg tcctgccaat tcaaatcttt    780
aactgggtct ctcgtcccca ggctgagttc agaatttgg cggcggccgc gatcatcgtg    840
ttgctagcga ttttgctaac catgaactcg atcgcgatcg tgattcgcaa caagttgcaa    900
gtcaaacgct aa                                                        912

<210> SEQ ID NO 41
<211> LENGTH: 264
<212> TYPE: PRT
<213> ORGANISM: Synechococcus elongates PCC7942

<400> SEQUENCE: 41

Met Ser Pro Thr Ala Gly Glu Asn Ile Leu Leu Lys Ala Glu Ala Leu
1               5                   10                  15

Ser Val Tyr Tyr Gly Asn Ser Leu Ala Val Lys Asp Val Tyr Leu Glu
            20                  25                  30

Val Pro Lys Asn Lys Ile Val Ala Phe Ile Gly Pro Ser Gly Cys Gly
        35                  40                  45

Lys Ser Thr Ile Leu Arg Cys Phe Asn Arg Met Asn Asp Leu Ile Asn
    50                  55                  60

Gly Cys Arg Val Gln Gly Arg Ile Thr Phe His Asp Gln Glu Ile Asn
65                  70                  75                  80

Asp Gly Arg Val Asp Ala Val Glu Leu Arg Ser Arg Ile Gly Met Val
                85                  90                  95

Phe Gln Lys Pro Asn Pro Phe Pro Lys Ser Ile Tyr Glu Asn Ile Ala
            100                 105                 110
```

```
Tyr Gly Ala Arg Ile Asn Gly Tyr Gln Gly Asp Met Asp Glu Leu Val
            115                 120                 125

Glu Lys Ser Leu Arg Gln Ala Ala Leu Trp Asp Glu Val Lys Asp Lys
    130                 135                 140

Leu Lys Asp Ser Gly Leu Ala Leu Ser Gly Gln Gln Gln Arg Leu
145                 150                 155                 160

Cys Ile Ala Arg Thr Val Ala Val Gln Pro Glu Val Ile Leu Met Asp
                165                 170                 175

Glu Pro Cys Ser Ala Leu Asp Pro Ile Ser Thr Leu Ala Ile Glu Glu
            180                 185                 190

Leu Met Gln Thr Leu Lys Glu Gln Tyr Thr Ile Ile Val Thr His
    195                 200                 205

Asn Met Gln Gln Ala Ser Arg Thr Ser Asp Tyr Thr Ala Phe Phe Asn
210                 215                 220

Ala Arg Ala Thr Glu Gly Gly Lys Met Gly Tyr Leu Val Glu Phe
225                 230                 235                 240

Asp Thr Thr Glu Lys Ile Phe Asp Ser Pro Asp Gln Glu Ala Thr Ala
                245                 250                 255

Asp Tyr Val Ser Gly Arg Phe Gly
            260
```

<210> SEQ ID NO 42
<211> LENGTH: 795
<212> TYPE: DNA
<213> ORGANISM: Synechococcus elongates PCC7942

<400> SEQUENCE: 42

```
atgagcccca ctgctggtga gaacattctg ctaaaggccg aagccctctc ggtttattac      60
ggcaattcgc ttgcggtcaa agacgtctac ttggaagttc ccaagaacaa gatcgttgcc     120
tttatcggtc catcgggttg cggcaagagc actatccttc gctgctttaa ccggatgaac     180
gacctgatca atggctgccg tgttcagggc cgaatcacct ccacgatca ggaaatcaac      240
gacggtcgtg tcgatgctgt ggaactgcgc agccgcatcg gcatggtgtt ccagaaaccc     300
aaccccttcc ccaagagcat ctacgaaaac atcgcttatg gtgcccggat taacggctac     360
caaggcgata tggatgagct ggtcgaaaag tcgctgcgtc aagcggcact ctgggatgag     420
gtcaaggata agctgaaaga tagtggtctt gccctctcgg gtggtcagca gcagcggctt     480
tgcattgctc gtaccgttgc tgtgcagcct gaggtgatct tgatggatga gccttgctcg     540
gcactcgacc ccatctcgac cttggcgatc gaggagttga tgcagactct gaaagagcag     600
tacacgatca tcatcgtgac tcacaacatg cagcaggctt ctcgaacttc ggactacacc     660
gcattcttca atgcgcgggc aaccgaaggc ggcggcaaga tgggctacct ggtggaattc     720
gacaccaccg agaaaatctt tgatagccca gaccaagaag cgacggccga ctacgtcagt     780
ggccgtttcg gctaa                                                      795
```

<210> SEQ ID NO 43
<211> LENGTH: 27
<212> TYPE: DNA
<213> ORGANISM: Artificial Sequence
<220> FEATURE:
<223> OTHER INFORMATION: Artificially Synthesized Sequence

<400> SEQUENCE: 43

```
ggcggacatt gccgacgcca acgcggg                                           27
```

<210> SEQ ID NO 44
<211> LENGTH: 37
<212> TYPE: DNA
<213> ORGANISM: Artificial Sequence
<220> FEATURE:
<223> OTHER INFORMATION: Artificially Synthesized Sequence

<400> SEQUENCE: 44
cgctcacaat tccacttaga ctttggtgcg atcggta                        37

<210> SEQ ID NO 45
<211> LENGTH: 40
<212> TYPE: DNA
<213> ORGANISM: Artificial Sequence
<220> FEATURE:
<223> OTHER INFORMATION: Artificially Synthesized Sequence

<400> SEQUENCE: 45
tcgcaccaaa gtctaagtgg aattgtgagc ggataacaat                     40

<210> SEQ ID NO 46
<211> LENGTH: 45
<212> TYPE: DNA
<213> ORGANISM: Artificial Sequence
<220> FEATURE:
<223> OTHER INFORMATION: Artificially Synthesized Sequence

<400> SEQUENCE: 46
gtgatggctt cagggtttta gaaaaactca tcgagcatca aatga               45

<210> SEQ ID NO 47
<211> LENGTH: 37
<212> TYPE: DNA
<213> ORGANISM: Artificial Sequence
<220> FEATURE:
<223> OTHER INFORMATION: Artificially Synthesized Sequence

<400> SEQUENCE: 47
gatgagtttt tctaaacccc tgaagccatc acccttt                        37

<210> SEQ ID NO 48
<211> LENGTH: 23
<212> TYPE: DNA
<213> ORGANISM: Artificial Sequence
<220> FEATURE:
<223> OTHER INFORMATION: Artificially Synthesized Sequence

<400> SEQUENCE: 48
gcccatcgag gtggagccgt tgg                                       23

<210> SEQ ID NO 49
<211> LENGTH: 20
<212> TYPE: DNA
<213> ORGANISM: Artificial Sequence
<220> FEATURE:
<223> OTHER INFORMATION: Artificially Synthesized Sequence

<400> SEQUENCE: 49
ccggtgcgag atgttcagcg                                           20

<210> SEQ ID NO 50
<211> LENGTH: 37
<212> TYPE: DNA
<213> ORGANISM: Artificial Sequence
<220> FEATURE:
<223> OTHER INFORMATION: Artificially Synthesized Sequence

```
<400> SEQUENCE: 50
gcgtcacccg gcaatcatga gcgaggcggc aaggact                              37

<210> SEQ ID NO 51
<211> LENGTH: 42
<212> TYPE: DNA
<213> ORGANISM: Artificial Sequence
<220> FEATURE:
<223> OTHER INFORMATION: Artificially Synthesized Sequence

<400> SEQUENCE: 51
gccgcctcgc tcatgattgc cgggtgacgc acaccgtgga aa                        42

<210> SEQ ID NO 52
<211> LENGTH: 36
<212> TYPE: DNA
<213> ORGANISM: Artificial Sequence
<220> FEATURE:
<223> OTHER INFORMATION: Artificially Synthesized Sequence

<400> SEQUENCE: 52
caacaacggt gagcattagg tggcggtact tgggtc                               36

<210> SEQ ID NO 53
<211> LENGTH: 34
<212> TYPE: DNA
<213> ORGANISM: Artificial Sequence
<220> FEATURE:
<223> OTHER INFORMATION: Artificially Synthesized Sequence

<400> SEQUENCE: 53
gtaccgccac ctaatgctca ccgttgttgt cagg                                 34

<210> SEQ ID NO 54
<211> LENGTH: 43
<212> TYPE: PRT
<213> ORGANISM: Anabaena sp. 7120

<400> SEQUENCE: 54

Met Ala Ile Ala Ile Lys Lys Pro Leu Leu Thr Ser Val Ala Val Ala
1               5                   10                  15

Val Leu Ala Leu Val Gly Cys Gln Ala Pro Asn Asn Thr Thr Thr Asn
            20                  25                  30

Gly Ser Thr Ala Pro Asn Ala Lys Ser Ala Ala
        35                  40

<210> SEQ ID NO 55
<211> LENGTH: 129
<212> TYPE: DNA
<213> ORGANISM: Anabaena sp. 7120

<400> SEQUENCE: 55
atggcgatcg caatcaaaaa acccttactg acatctgtgg ctgtagctgt gttggcactg     60
gttggctgtc aagcacccaa taacactact actaatggtt ctactgctcc taatgcaaag    120
agcgcagct                                                            129

<210> SEQ ID NO 56
<211> LENGTH: 25
<212> TYPE: PRT
<213> ORGANISM: Synechococcus elongates PCC7942

<400> SEQUENCE: 56
```

```
Met Ala Ser Leu Lys Phe Arg Leu Leu Gly Leu Ala Thr Leu Ala Val
1               5                   10                  15

Leu Ala Thr Thr Ala Cys Ser Ser Gly
            20                  25

<210> SEQ ID NO 57
<211> LENGTH: 75
<212> TYPE: DNA
<213> ORGANISM: Synechococcus elongates PCC7942

<400> SEQUENCE: 57
atggcttccc taaaattccg actgcttggc cttgcaacgc tggcagtctt ggcaactacc    60
gcttgcagct ctggt                                                    75

<210> SEQ ID NO 58
<211> LENGTH: 24
<212> TYPE: PRT
<213> ORGANISM: Ralstonia sp. 4506

<400> SEQUENCE: 58

Met Lys Lys Leu Ala Ser Ala Leu Leu Ser Val Leu Leu Ala Ala Val
1               5                   10                  15

Cys Ser Ile Gly His Ala Ser Ser
            20

<210> SEQ ID NO 59
<211> LENGTH: 72
<212> TYPE: DNA
<213> ORGANISM: Ralstonia sp. 4506

<400> SEQUENCE: 59
atgaaaaaac tcgcatccgc attattgtct gtcttgcttg ccgccgtctg cagcattggc    60
catgcatcat cc                                                       72

<210> SEQ ID NO 60
<211> LENGTH: 33
<212> TYPE: PRT
<213> ORGANISM: Pseudomonas stutzeri WM88

<400> SEQUENCE: 60

Met Gln Val Phe Thr Leu Phe Ser Lys Phe Lys Lys Ala Leu Thr Arg
1               5                   10                  15

Ala Ile Leu Ala Phe Ile Ala Thr Ile Ile Val Cys Thr Pro Ala Gln
            20                  25                  30

Ala

<210> SEQ ID NO 61
<211> LENGTH: 4068
<212> TYPE: DNA
<213> ORGANISM: Synechococcus elongates PCC7942

<400> SEQUENCE: 61
atggctcaat taccccttca gcttctgcac ttttcagatc aagaagcagg tattcctgct    60
ttaaaagatg ctcccaatct atcagcagtc ctgaaggctc tgaaagacca agacggggat   120
gatgtagata ctgatcctga ctatctgaac acattaattc tttcatcagg tgatgcctac   180
attccaggca ccttttttgga tgctagcgtc caggcttacg gtggccaagg acgagctgat   240
atcctcatcc agaatgagct ggcgtacag gccatttctt ttggcaacca tgagtttgac   300
```

```
ttgggaactg gcttgattgc caatctgttg aagccctcag cagatggact ctatgccggg    360
gctgccttcc cttacctcag tggcaacctc aactttgcac cagatgcaaa cctcgcaccc    420
ttagtcactg ctgatggtca ggaagccagc acgatcgcgg gtaaaatcgc ggcgagcagc    480
atcattactg tcaatgggga aaagattggc gttgttggcg caacaacgcc gattctgcgc    540
agcatttcta gcccaggtgc tgttcaaatc gagcctagtc cctttggcag tgttcctagc    600
gcccaagaac tcgatgccct agctgccatc attcaggccg acgttgatgc gctgctggca    660
aataaccctg atctcaataa agtgattttg ctgtctcaca tgcagcaaat ctcgattgag    720
caagaaattg caaaacgact gagaaacgtt gacatcatcg ttgctggcgg ttctaatact    780
cgtctacttg atagcaacga tgtactaaga gctggtgaca ccaagcaggg tgaatatccc    840
ttctttacaa atgatgcaga tggcaagccg atcgctgttg tcaacacaga tggaaattat    900
aagtatgttg gtcggctagt tattgatttt gatgaaaacg gtaatgttat tgccgagagc    960
tatgacccca atgtaagcgg ggtctatgcc actgacgata ctggtgttgc tgccctaaac   1020
gctcagaatt tagttgatcc tgaaatccaa caaattgttg acaacttgag ctctgttatt   1080
tccagcttag atggcgcaat ttttggtagt acagacgtct ttctcaacgg cgcgagaagt   1140
gatatccgca tccaagaaac caacttaggt aacttaactg cggatgcgaa ccttgcctac   1200
gccaagacta ttgattcgac tgtaaccctc tcactgaaga atggtggcgg tgttcgtaac   1260
aacatcggtt tcgtcacctt cccggagggc tctaccgatc cagatgatgt attgaaactc   1320
ccgccagcag ctaaccctct tgcaggcaaa gaggaagggg atatttctca gctggatatt   1380
acgaactcgc tgagttttaa caatggctta gcgctgatca cattgactgc ggaagaactt   1440
ctagaaatcg tcgagtatgg cttttgcagcc agtagtctta acgatggtaa tacccaaggt   1500
cgcttccctc agattggtgg cttctccgtt gcagttgatt tgactcgtgc cccaggcgat   1560
cgcgtcctct cgctagcgat taaagacgaa gagggccgcg acattgatgt cgttgtccgt   1620
aatggcgaga tcgttggcaa ccccgctcgc accttccgga tggtaacgct cagcttttg    1680 gccgacgggg gcgatggata tccattcccg accggtgagg cgactaatcg cattgatctt   1740
gctcaacctg ccgaggctga acggactggt ttagcgcaat ttgcaccaga tggcactgag   1800
caagatgttc tagcggagta tctagctact cgcttcactg agaattcttt tgacaaactg   1860
gattctgcgc gtgatttcga tactcgcatt cagaacgtca gcttccgcga tgatacggtc   1920
attaactctc aaatccagct gagtgttcta ggaacctttg caacaggcag ctttgaccag   1980
ggcgccgcag aaatcccggc ctatgacccg attagccaac gtctctttgt tgtcaatgcc   2040
caaaacagcc gcgtagatgt cctagacatc agcgacccta ctcgacctac cctcattgga   2100
tttatcgata cttcgagctt tggctctcct aacagtgtcg ccatccaaaa tggtctggtt   2160
gcgatcgctg ttcaaaatgc gaatccgcag gagaacggcc aagtcttctt ctatcagtcc   2220
accgctagtt ccttcaatgc tccgcttcgg gcaattgaag tgggcgccct acccgacatg   2280 ctgatctttta cgcctgacgg ctccaaggtt ttggtagcta atgaaggtga acctaatgaa   2340
gattacaccg ttgatcccga aggttcagtc agcatcattg accttagtct gggtgtagcc   2400
aacgctcagg ttagaacagc aacttttact gccttcaatg accgaaaggc agagctgcaa   2460
gaagctggcg tccgcatttt gaaagatgat gcgactgttg ccgaggatat tgagccggag   2520
tacatcgcta tctctcccga tggcaacact gcagtggtga ctctccagga agccaatgca   2580
ctggctttca ttgatttggc gaccgcaacg gttacggata tcaagccgct gggtctaaag   2640
gactttagtc ttccgggtaa tgcgctggat ccgagcgatc gcgatggagg tattaatctc   2700
```

```
cgtaacgtcc cagtgtttgg gctctaccaa ccagatgcca ttgcctcctt cgttggtgct    2760
gatgggaaga cctactacat cactgccaat gaaggcgata gccgagtccg ccgacgggga    2820
gatgacatca tccccgaggt tggtgaaggg gacatcttca atgaagaggt tcgagtcagc    2880
agcaaccgtt acattctcga cccaacgatc ttcccaaatg cagctgagct gaagcagaac    2940
tcgaatctgg gtcgcctgac cgttaccaac gaatcaggtg atctagatgg ggatggtgac    3000
tttgaccaaa tcgtcacttt tggagctcgc tctttctcga tcctcaattc cgagggtgag    3060
cttgttttg atagtggcga tcagctagag cgaatcactg ctagcttctt ccctgaaaac    3120
ttcaacgcca gcaatgacaa taacgatcta gataaccgca gtgacaacaa aggtcctgag    3180
cctgaaggtg tcgtgattgg ccagattaac gatcgcacct atgcctttgt cggtcttgag    3240
cggaccggtg gcgtcatagt ctacgacgtg actaccccta acaatcccac ctttgttcag    3300
tacctcaaca atcgtaattt caacgctgat gttgaaagtg ccgaagcggg tgatttaggc    3360
cctgagggtc ttgctttcat ctctgcagag gacagcccca acggcaaacc tctgttggtt    3420
gtcgccaacg agatcagtgg aactacaacg ctctatgaga ttaatgtcgg ttctaatcct    3480
gacttgatca gttagacaa cagcgcccag attgcttaca tcacttatct aggacggcct    3540
ggcgatcgcg gtggactgac ctttggaat gaggttctga gagatgccga atcagctac    3600
gaccctcaaa ctggtgattt aattactggt gaagaagttc ttccttcaa cgccttcatc    3660
aacgggtttg gagattcttc tgaagctgat caaatctacg gtggtaaatc tgcagccgat    3720
caggtgaact taatttataa ctttgccttc aatcgtaatg ctgagagtgc tggccaagcc    3780
ttctgggtca accagctgaa tagtcgccag ctcagcttgg cggaactggc tctagaaatt    3840
ggtctgaacg cgacaggcaa tgattcagta gttcttaaca acaagattag aagtgccact    3900
ctgttcaccg attcgattga cacgaatgtt gaactagctg cttatcaagg tagtaagggg    3960
accagctttg tcagacctg gctagatcag tttgacttta gccaaagtag ccaagctctg    4020
gttgatagtg ctcttaacgc tttagtcaat gacctacctc ttggatag                 4068
```

<210> SEQ ID NO 62
<211> LENGTH: 1355
<212> TYPE: PRT
<213> ORGANISM: Synechococcus elongates PCC7942

<400> SEQUENCE: 62

Met Ala Gln Phe Thr Leu Gln Leu Leu His Phe Ser Asp Gln Glu Ala
1               5                   10                  15

Gly Ile Pro Ala Leu Lys Asp Ala Pro Asn Leu Ser Ala Val Leu Lys
            20                  25                  30

Ala Leu Lys Asp Gln Asp Gly Asp Val Asp Thr Asp Pro Asp Tyr
        35                  40                  45

Leu Asn Thr Leu Ile Leu Ser Ser Gly Asp Ala Tyr Ile Pro Gly Thr
    50                  55                  60

Phe Leu Asp Ala Ser Val Gln Ala Tyr Gly Gln Gly Arg Ala Asp
65                  70                  75                  80

Ile Leu Ile Gln Asn Glu Leu Gly Val Gln Ala Ile Ser Phe Gly Asn
                85                  90                  95

His Glu Phe Asp Leu Gly Thr Gly Leu Ile Ala Asn Leu Leu Lys Pro
            100                 105                 110

Ser Ala Asp Gly Leu Tyr Ala Gly Ala Ala Phe Pro Tyr Leu Ser Gly
        115                 120                 125

```
Asn Leu Asn Phe Ala Pro Asp Ala Asn Leu Ala Pro Leu Val Thr Ala
    130                 135                 140

Asp Gly Gln Glu Ala Ser Thr Ile Ala Gly Lys Ile Ala Ala Ser Ser
145                 150                 155                 160

Ile Ile Thr Val Asn Gly Glu Lys Ile Gly Val Val Gly Ala Thr Thr
                165                 170                 175

Pro Ile Leu Arg Ser Ile Ser Ser Pro Gly Ala Val Gln Ile Glu Pro
            180                 185                 190

Ser Pro Phe Gly Ser Val Pro Ser Ala Gln Glu Leu Asp Ala Leu Ala
        195                 200                 205

Ala Ile Ile Gln Ala Asp Val Asp Ala Leu Leu Ala Asn Asn Pro Asp
210                 215                 220

Leu Asn Lys Val Ile Leu Ser His Met Gln Gln Ile Ser Ile Glu
225                 230                 235                 240

Gln Glu Ile Ala Lys Arg Leu Arg Asn Val Asp Ile Ile Val Ala Gly
                245                 250                 255

Gly Ser Asn Thr Arg Leu Leu Asp Ser Asn Asp Val Leu Arg Ala Gly
            260                 265                 270

Asp Thr Lys Gln Gly Glu Tyr Pro Phe Phe Thr Asn Asp Ala Asp Gly
        275                 280                 285

Lys Pro Ile Ala Val Val Asn Thr Asp Gly Asn Tyr Lys Tyr Val Gly
290                 295                 300

Arg Leu Val Ile Asp Phe Asp Glu Asn Gly Asn Val Ile Ala Glu Ser
305                 310                 315                 320

Tyr Asp Pro Asn Val Ser Gly Val Tyr Ala Thr Asp Thr Gly Val
                325                 330                 335

Ala Ala Leu Asn Ala Gln Asn Leu Val Asp Pro Glu Ile Gln Gln Ile
            340                 345                 350

Val Asp Asn Leu Ser Ser Val Ile Ser Ser Leu Asp Gly Ala Ile Phe
        355                 360                 365

Gly Ser Thr Asp Val Phe Leu Asn Gly Ala Arg Ser Asp Ile Arg Ile
370                 375                 380

Gln Glu Thr Asn Leu Gly Asn Leu Thr Ala Asp Ala Asn Leu Ala Tyr
385                 390                 395                 400

Ala Lys Thr Ile Asp Ser Thr Val Thr Leu Ser Leu Lys Asn Gly Gly
                405                 410                 415

Gly Val Arg Asn Asn Ile Gly Phe Val Thr Phe Pro Glu Gly Ser Thr
            420                 425                 430

Asp Pro Asp Asp Val Leu Lys Leu Pro Pro Ala Asn Pro Leu Ala
        435                 440                 445

Gly Lys Glu Glu Gly Asp Ile Ser Gln Leu Asp Ile Thr Asn Ser Leu
450                 455                 460

Ser Phe Asn Asn Gly Leu Ala Leu Ile Thr Leu Thr Ala Glu Glu Leu
465                 470                 475                 480

Leu Glu Ile Val Glu Tyr Gly Phe Ala Ala Ser Ser Leu Asn Asp Gly
                485                 490                 495

Asn Thr Gln Gly Arg Phe Pro Gln Ile Gly Gly Phe Ser Val Ala Val
            500                 505                 510

Asp Leu Thr Arg Ala Pro Gly Asp Arg Val Leu Ser Leu Ala Ile Lys
        515                 520                 525

Asp Glu Glu Gly Arg Asp Ile Asp Val Val Arg Asn Gly Glu Ile
530                 535                 540

Val Gly Asn Pro Ala Arg Thr Phe Arg Met Val Thr Leu Ser Phe Leu
```

-continued

```
         545                 550                 555                 560
    Ala Asp Gly Gly Asp Gly Tyr Pro Phe Pro Thr Gly Glu Ala Thr Asn
                         565                 570                 575

Arg Ile Asp Leu Ala Gln Pro Ala Glu Ala Glu Arg Thr Gly Leu Ala
                     580                 585                 590

Gln Phe Ala Pro Asp Gly Thr Glu Gln Asp Val Leu Ala Glu Tyr Leu
                 595                 600                 605

Ala Thr Arg Phe Thr Glu Asn Ser Phe Asp Lys Leu Asp Ser Ala Arg
             610                 615                 620

Asp Phe Asp Thr Arg Ile Gln Asn Val Ser Phe Arg Asp Asp Thr Val
    625                 630                 635                 640

Ile Asn Ser Gln Ile Gln Leu Ser Val Leu Gly Thr Phe Ala Thr Gly
                     645                 650                 655

Ser Phe Asp Gln Gly Ala Ala Glu Ile Pro Ala Tyr Asp Pro Ile Ser
                 660                 665                 670

Gln Arg Leu Phe Val Val Asn Ala Gln Asn Ser Arg Val Asp Val Leu
             675                 680                 685

Asp Ile Ser Asp Pro Thr Arg Pro Thr Leu Ile Gly Phe Ile Asp Thr
    690                 695                 700

Ser Ser Phe Gly Ser Pro Asn Ser Val Ala Ile Gln Asn Gly Leu Val
    705                 710                 715                 720

Ala Ile Ala Val Gln Asn Ala Asn Pro Gln Glu Asn Gly Gln Val Phe
                     725                 730                 735

Phe Tyr Gln Ser Thr Ala Ser Ser Phe Asn Ala Pro Leu Arg Ala Ile
                 740                 745                 750

Glu Val Gly Ala Leu Pro Asp Met Leu Ile Phe Thr Pro Asp Gly Ser
             755                 760                 765

Lys Val Leu Val Ala Asn Gly Glu Pro Asn Glu Asp Tyr Thr Val
             770                 775                 780

Asp Pro Glu Gly Ser Val Ser Ile Ile Asp Leu Ser Leu Gly Val Ala
    785                 790                 795                 800

Asn Ala Gln Val Arg Thr Ala Thr Phe Thr Ala Phe Asn Asp Arg Lys
                     805                 810                 815

Ala Glu Leu Gln Glu Ala Gly Val Arg Ile Leu Lys Asp Asp Ala Thr
                 820                 825                 830

Val Ala Glu Asp Ile Glu Pro Glu Tyr Ile Ala Ile Ser Pro Asp Gly
             835                 840                 845

Asn Thr Ala Val Val Thr Leu Gln Glu Ala Asn Ala Leu Ala Phe Ile
    850                 855                 860

Asp Leu Ala Thr Ala Thr Val Thr Asp Ile Lys Pro Leu Gly Leu Lys
    865                 870                 875                 880

Asp Phe Ser Leu Pro Gly Asn Ala Leu Asp Pro Ser Asp Arg Asp Gly
                     885                 890                 895

Gly Ile Asn Leu Arg Asn Val Pro Val Phe Gly Leu Tyr Gln Pro Asp
                 900                 905                 910

Ala Ile Ala Ser Phe Val Gly Ala Asp Gly Lys Thr Tyr Tyr Ile Thr
             915                 920                 925

Ala Asn Glu Gly Asp Ser Arg Val Arg Pro Thr Gly Asp Ile Ile
    930                 935                 940

Pro Glu Val Gly Glu Gly Asp Ile Phe Asn Glu Val Arg Val Ser
    945                 950                 955                 960

Ser Asn Arg Tyr Ile Leu Asp Pro Thr Ile Phe Pro Asn Ala Ala Glu
                     965                 970                 975
```

```
Leu Lys Gln Asn Ser Asn Leu Gly Arg Leu Thr Val Thr Asn Glu Ser
              980                 985                 990

Gly Asp Leu Asp Gly Asp Gly Asp  Phe Asp Gln Ile Val  Thr Phe Gly
             995                1000                 1005

Ala Arg Ser Phe Ser Ile Leu Asn Ser Glu Gly Glu  Leu Val Phe
    1010                1015                1020

Asp Ser Gly Asp Gln Leu Glu Arg Ile Thr Ala Ser  Phe Phe Pro
    1025                1030                1035

Glu Asn Phe Asn Ala Ser Asn Asp Asn Asn Asp Leu  Asp Asn Arg
    1040                1045                1050

Ser Asp Asn Lys Gly Pro Glu Pro Glu Gly Val Val  Ile Gly Gln
    1055                1060                1065

Ile Asn Asp Arg Thr Tyr Ala Phe Val Gly Leu Glu  Arg Thr Gly
    1070                1075                1080

Gly Val Ile Val Tyr Asp Val Thr Thr Pro Asn Asn  Pro Thr Phe
    1085                1090                1095

Val Gln Tyr Leu Asn Asn Arg Asn Phe Asn Ala Asp  Val Glu Ser
    1100                1105                1110

Ala Glu Ala Gly Asp Leu Gly Pro Glu Gly Leu Ala  Phe Ile Ser
    1115                1120                1125

Ala Glu Asp Ser Pro Asn Gly Lys Pro Leu Leu Val  Val Ala Asn
    1130                1135                1140

Glu Ile Ser Gly Thr Thr Thr Leu Tyr Glu Ile Asn  Val Gly Ser
    1145                1150                1155

Asn Pro Asp Leu Ile Lys Leu Asp Asn Ser Ala Gln  Ile Ala Tyr
    1160                1165                1170

Ile Thr Tyr Leu Gly Arg Pro Gly Asp Arg Gly Gly  Leu Thr Phe
    1175                1180                1185

Trp Asn Glu Val Leu Arg Asp Ala Glu Ile Ser Tyr  Asp Pro Gln
    1190                1195                1200

Thr Gly Asp Leu Ile Thr Gly Glu Glu Val Leu Pro  Phe Asn Ala
    1205                1210                1215

Phe Ile Asn Gly Phe Gly Asp Ser Ser Glu Ala Asp  Gln Ile Tyr
    1220                1225                1230

Gly Gly Lys Ser Ala Ala Asp Gln Val Asn Leu Ile  Tyr Asn Phe
    1235                1240                1245

Ala Phe Asn Arg Asn Ala Glu Ser Ala Gly Gln Ala  Phe Trp Val
    1250                1255                1260

Asn Gln Leu Asn Ser Arg Gln Leu Ser Leu Ala Glu  Leu Ala Leu
    1265                1270                1275

Glu Ile Gly Leu Asn Ala Thr Gly Asn Asp Ser Val  Val Leu Asn
    1280                1285                1290

Asn Lys Ile Arg Ser Ala Thr Leu Phe Thr Asp Ser  Ile Asp Thr
    1295                1300                1305

Asn Val Glu Leu Ala Ala Tyr Gln Gly Ser Lys Gly  Thr Ser Phe
    1310                1315                1320

Gly Gln Thr Trp Leu Asp Gln Phe Asp Phe Ser Gln  Ser Ser Gln
    1325                1330                1335

Ala Leu Val Asp Ser Ala Leu Asn Ala Leu Val Asn  Asp Leu Pro
    1340                1345                1350

Leu Gly
    1355
```

<210> SEQ ID NO 63
<211> LENGTH: 12462
<212> TYPE: DNA
<213> ORGANISM: Artificial Sequence
<220> FEATURE:
<223> OTHER INFORMATION: pNSptxAD

<400> SEQUENCE: 63

| | | | | | |
|---|---|---|---|---|---|
| cccattcgcc | attcaggctg | cgcaactgtt | gggaagggcg | atcggtgcgg | gcctcttcgc | 60 |
| tattacgcca | gctggcgaaa | gggggatgtg | ctgcaaggcg | attaagttgg | gtaacgccag | 120 |
| ggttttccca | gtcacgacgt | tgtaaaacga | cggccagtgc | caagctaaaa | gcgctccgca | 180 |
| tggatctgac | caacatgatc | attgagttgc | gcgtttccaa | tgccttctcc | aagggcggca | 240 |
| ttcccctgac | tgttgaaggc | gttgccaata | tcaagattgc | tggggaagaa | ccgaccatcc | 300 |
| acaacgcgat | cgagcggctg | cttggcaaaa | accgtaagga | aatcgagcaa | attgccaagg | 360 |
| agaccctcga | aggcaacttg | cgtggtgttt | tagccagcct | cacgccggag | cagatcaacg | 420 |
| aggacaaaat | tgcctttgcc | aaaagtctgc | tggaagaggc | ggaggatgac | cttgagcagc | 480 |
| tgggtctagt | cctcgatacg | ctgcaagtcc | agaacatttc | cgatgaggtc | ggttatctct | 540 |
| cggctagtgg | acgcaagcag | cgggctgatc | tgcagcgaga | tgcccgaatt | gctgaagccg | 600 |
| atgcccaggc | tgcctctgcg | atccaaacgg | ccgaaaatga | caagatcacg | gccctgcgtc | 660 |
| ggatcgatcg | cgatgtagcg | atcgcccaag | ccgaggccga | cgccggatt | caggatgcgt | 720 |
| tgacgcggcg | cgaagcggtg | gtggccgaag | ctgaagcgga | cattgctacc | gaagtcgctc | 780 |
| gtagccaagc | agaactccct | gtgcagcagg | agcggatcaa | acaggtgcag | cagcaacttc | 840 |
| aagccgatgt | gatcgcccca | gctgaggcag | cttgtaaacg | ggcgatcgcg | gaagcgcggg | 900 |
| gggccgccgc | ccgtatcgtc | gaagatggaa | aagctcaagc | ggaagggacc | caacggctgg | 960 |
| cggaggcttg | gcagaccgct | ggtgctaatg | cccgcgacat | cttcctgctc | cagaagctcg | 1020 |
| actatgcttg | taaccgtttt | tgtgaaaaaa | tttttaaaat | aaaaaagggg | acctctaggg | 1080 |
| tccccaatta | attagtaata | taatctatta | aaggtcattc | aaaaggtcat | ccaccggatc | 1140 |
| agcttagtaa | agccctcgct | agattttaat | gcggatgttg | cgattacttc | gccaactatt | 1200 |
| gcgataacaa | gaaaaagcca | gcctttcatg | atatatctcc | caatttgtgt | agggcttatt | 1260 |
| atgcacgctt | aaaaataata | aaagcagact | tgacctgata | gtttggctgt | gagcaattat | 1320 |
| gtgcttagtg | catctaacgc | ttgagttaag | ccgcgccgcg | aagcggcgtc | ggcttgaacg | 1380 |
| aattgttaga | cattatttgc | cgactacctt | ggtgatctcg | cctttcacgt | agtggacaaa | 1440 |
| ttcttccaac | tgatctgcgc | gcgaggccaa | gcgatcttct | tcttgtccaa | gataagcctg | 1500 |
| tctagcttca | agtatgacgg | gctgatactg | ggccggcagg | cgctccattg | cccagtcggc | 1560 |
| agcgacatcc | ttcggcgcga | ttttgccggt | tactgcgctg | taccaaatgc | gggacaacgt | 1620 |
| aagcactaca | tttcgctcat | cgccagccca | gtcgggcggc | gagttccata | gcgttaaggt | 1680 |
| ttcatttagc | gcctcaaata | gatcctgttc | aggaaccgga | tcaaagagtt | cctccgccgc | 1740 |
| tggacctacc | aaggcaacgc | tatgttctct | tgcttttgtc | agcaagatag | ccagatcaat | 1800 |
| gtcgatcgtg | gctggctcga | agatacctgc | aagaatgtca | ttgcgctgcc | attctccaaa | 1860 |
| ttgcagttcg | cgcttagctg | gataacgcca | cggaatgatg | tcgtcgtgca | acaacaatggt | 1920 |
| gacttctaca | gcgcggagaa | tctcgctctc | tccaggggaa | gccgaagttt | ccaaaaggtc | 1980 |
| gttgatcaaa | gctcgccgcg | ttgtttcatc | aagccttacg | gtcaccgtaa | ccagcaaatc | 2040 |
| aatatcactg | tgtggcttca | ggccgccatc | cactgcggag | ccgtacaaat | gtacggccag | 2100 |

```
caacgtcggt tcgagatggc gctcgatgac gccaactacc tctgatagtt gagtcgatac    2160
ttcggcgatc accgcttccc tcatgatgtt aactttgtt  ttagggcgac tgccctgctg    2220
cgtaacatcg ttgctgctcc ataacatcaa acatcgaccc acggcgtaac gcgcttgctg    2280
cttggatgcc cgaggcatag actgtacccc aaaaaaacag tcataacaag ccatgaaaac    2340
cgccactgcg ccgttaccac cgctgcgttc ggtcaaggtt ctggaccagt tgcgtgagcg    2400
catacgctac ttgcattaca gcttacgaac cgaacaggct tatgtccact gggttcgtgc    2460
cttcatccgt ttccacggtg tgcgtcaccc ggcaaccttg ggcagcagcg aagtcgaggc    2520
atttctgtcc tggctggcga acgagcgcaa ggtttcggtc tccacgcatc gtcaggcatt    2580
ggcggccttg ctgttcttct acggcaaggt gctgtgcacg gatctgccct ggcttcagga    2640
gatcggaaga cctcggccgt cgcggcgctt gccggtggtg ctgacccgg  atgaagtggt    2700
tcgcatcctc ggttttctgg aaggcgagca tcgtttgttc gcccagcttc tgtatggaac    2760
gggcatgcgg atcagtgagg gtttgcaact gcgggtcaag gatctggatt tcgatcacgg    2820
cacgatcatc gtgcgggagg gcaagggctc caaggatcgg gccttgatgt tacccgagag    2880
cttggcaccc agcctgcgcg agcagggaa  ttgatccggt ggatgacctt ttgaatgacc    2940
tttaatagat tatattacta attaattggg gaccctagag gtcccctttt ttattttaaa    3000
aatttttca  caaaacggtt tacaagcata gtcgagttac gttgacacca tcgaatggtg    3060
caaaaccttt cgcggtatgg catgatagcg cccggaagag agtcaattca gggtggtgaa    3120
tgtgaaacca gtaacgttat acgatgtcgc agagtatgcc ggtgtctctt atcagaccgt    3180
ttcccgcgtg gtgaaccagg ccagccacgt ttctgcgaaa acgcgggaaa aagtggaagc    3240
ggcgatggcg gagctgaatt acattcccaa ccgcgtggca caacaactgg cgggcaaaca    3300
gtcgttgctg attggcgttg ccacctccag tctggccctg cacgcgccgt cgcaaattgt    3360
cgcggcgatt aaatctcgcg ccgatcaact gggtgccagc gtggtggtgt cgatggtaga    3420
acgaagcggc gtcgaagcct gtaaagcggc ggtgcacaat cttctcgcgc aacgcgtcag    3480
tgggctgatc attaactatc cgctggatga ccaggatgcc attgctgtgg aagctgcctg    3540
cactaatgtt ccggcgttat tcttgatgt  ctctgaccag acacccatca acagtattat    3600
tttctcccat gaagacggta cgcgacgggc gtggagcatc tggtcgcatt gggtcaccag    3660
caaatcgcgc tgttagcggg cccattaagt tctgtctcgg cgcgtctgcg tctggctggc    3720
tggcataaat atctcactcg caatcaaatt cagccgatag cggaacggga aggcgactgg    3780
agtgccatgt ccgttttca  acaaaccatg caaatgctga atgagggcat cgttcccact    3840
gcgatgctgg ttgccaacga tcagatggcg ctgggcgcaa tgcgcgccat taccgagtcc    3900
gggctgcgcg ttggtgcgga tatctcggta gtgggatacg acgataccga agacagctca    3960
tgttatatcc cgccgttaac caccatcaaa caggattttc gcctgctggg gcaaaccagc    4020
gtggaccgct tgctgcaact ctctcagggc caggcggtga agggcaatca gctgttgccc    4080
gtctcactgg tgaaaagaaa aaccaccctg gcgcccaata cgcaaaccgc ctctccccgc    4140
gcgttggccg attcattaat gcagctggca cgacaggttt cccgactgga aagcgggcag    4200
tgagcgcaac gcaattaatg tgagttagcg cgaattgatc tggtttgaca gcttatcatc    4260
gactgcacgg tgcaccaatg cttctggcgt caggcagcca tcggaagctg tggtatggct    4320
gtgcaggtcg taaatcactg cataattcgt gtcgctcaag gcgcactccc gttctggata    4380
atgttttttg cgccgacatc ataacggttc tggcaaatat tctgaaatga gctgttgaca    4440
```

```
attaatcatc cggctcgtat aatgtgtgga attgtgagcg ataacaatt tcacacagga    4500
aacagaccat ggaattcgtg tcatatcacg acattaccat cgctgcaatt cagattcgta    4560
atcaggtcat cattttttgat tacgatttca aatctgccgg aggtgtcatg atcgaactac    4620
agaatgtctc agtcagttat ggtgatgcga ttgcactgta tcccaccact ctcaaactcc    4680
atcagggaca gttcaccgta ttgctcggat cttccggcgc tggaaaatcc acgctacttc    4740
gctgtattaa ttcgctgcat gcgtcgcagc gcggcaccac cattgtcgcc ggcttaggaa    4800
atttggcgaa ctcgcgtgca ttgcgcatgc atcgccgaca gactggcatg gtgtttcaac    4860
agcatcaatt gattggccga ctgacggctt tgcaaaacgt ttcgatgggc cgaatgggct    4920
accacacggc attacgcagt ctattccccc tcccggcgaa ggatcaatcc atatgcctgc    4980
aaagtctgga ccgagtcggc ttattgcaca aagccttaag ccgtgtcgac gcattgagcg    5040
gcggccagca gcaacgcatc ggtattgccc gggctctggc tcagcaacct aaactggtgt    5100
tggctgatga accggtagcc agcctcgatc ctgctactgc agagcgagtg ctaagtctgc    5160
tgcaccgcat ttgtaaagag gacgggattt cggcggtcgt cagcctgcat caggtagacc    5220
tcgctcaacg ttatgccgac cgtattattg gcctgtccca tggccgagtc attttttgatg    5280
ccgccccgca gactttggat caagccagtt acgacacgct gtatgaacaa gtaccccgtt    5340
cttcttttgag cgttccacaa gacgctcgag aggaacggct tatcgatact tcatttccca    5400
tgcaacttgc taccgtaaag gattgattat gaaaaaactc gcatccgcat tattgtctgt    5460
cttgcttgcc gccgtctgca gcattggcca tgcatcatcc aatcccgatc cagaaacgct    5520
caaagttgcg ctgctgccgg acgaaaacgc atcgaccgta attaaaaaca caagccgct    5580
cgaaatctat ctggaaaaag agctgggaaa gaaaattgag ctggtggtta ccactgatta    5640
ctcgtcaatg atcgaagcca tgcgtcacgg ccgtatcgac atggcatatt ttggccccctt    5700
gtcgtatgtg ctggctaagc aaaagagcga catcgagcca ttcgcagcga tgaagcaaaa    5760
gggtagcact acctaccagt ccgtattgat cgccaatact ggcgccggca tcgccaaaat    5820
cagtgatatc gtcaacaaga atgtcgctta cggtgataag gcatccacct ccagccattt    5880
gattccgaag tcgatattgg cggaaaacgg tttgaaagcc ggcgaaaact atcgcgaaca    5940
ctttgtcggt gcgcatgacg cggtggccat ggccgtgcaa aacggtcacg cgcaggctgg    6000
cggcttgagt aagccgattt ttgaatccct ggttcagcgc ggactggtcg atcccaacaa    6060
agtaaaagtt cttgccgaat cgaagccata tccgcaatac ccgtggacca tgcgcagcaa    6120
tctgaagccg gaactgaagg aaaagatccg tgcagccttc ttgaatctca agatccgga    6180
agtcctgaaa cctttcaaag ccgatggttt cggcccgatc agcgacaaag actatgacgt    6240
ggtgcgcagc cttggcacac tgctcaagct cgatctgtcg aagttctaag tgagcgacag    6300
catgcaagct gattttggtt tgattctggc cgagcgccag cgcgtatgga accgcacgat    6360
actgcagttt gccgttgtgc tggcgattgt gatcggttgc tggtattacg tcggcctatt    6420
tgatgccgag cgattgaagg atggcatgcc aagcctggta aaaattgccg gcgagatgtt    6480
cccaccgaac ttctcgcagg ctggcacctg ggtcaaaccg gtactggata ccttggccat    6540
gagtatcgcc ggtacggcaa tcgcggtatt gctatccatt cccttaggag tgctcgccgc    6600
gcggaatact agccctcatc cactcgtgta tcaagccaca cgcggcctgt aaacgcttt    6660
gcgatcgata cccgaactga tcatgggcat cctgttcgtg gcagccgttg gcttcggcgc    6720
attgccgggt gttttagccc taggcttaca ttccggttggc atgatcgcca aattttttttc    6780
ggaatcgatc gaacatgccg atccggcacc ggtagaagcc gcgcatgcag cgggctgcac    6840
```

```
gccattgcag gtgatttttc atgggatctt tccccaagtg cttccgcaaa tggccgatac   6900
cgcgatctat cgatgggaat acaacttccg tgcttcgacc gtgatgggca tggtcggcgc   6960
cggtggaatc gggttcgagc tgatgggctc tctgcgcatc atgcaatacc aggatgtctc   7020
ggctattttg ctggttattt taggcatggt taccctcgtc gacgccttca gctccttcct   7080
gcgtcgcaag ttcaaataac tcccaaagct tacaaaggtt tttatgaagc caaagtcgt    7140 cctcacccac tgggtgcacc cggaaatcat cgaattgttg ccgctagcg ccgatgttat    7200 ccccaacacc acacgggaaa ccttgccgcg ttctgaggta attgcgcgag ccaaagatgc   7260
ggatgcactc atggctttca tgccggacag catcgacagc gcgtttctcg aggaatgtcc   7320
aaagctgcgt gtcatcggcg ccgcgcttaa aggctatgat aacttcgatg tcaacgcctg   7380
cacacgccac ggtgtatggc ttacgattgt gccggatttg cttacgatcc cgaccgctga   7440
actgactatc ggccttcttc tcggtttgac aaggcatatg ctggaaggcg ataggcaaat   7500
ccgtagcgga cacttccaag gctggcggcc gacactatat ggctctggtt tgacaggaaa   7560
aacgcttggc atcattggta tggggcggt cggccgtgca atcgcccagc gcttggctgg   7620
ctttgaaatg aatctcttgt attgcgatcc gattccgctc aatgccgaac aagaaaaggc   7680
ttggcacgta cagcgcgtca cgctcgatga actgctcgaa aaatgtgatt atgtcgtgcc   7740
gatggttccg atggccgcag agacactgca tctgatcgat gccaccgcgt tggccaagat   7800
gaaaaccggt agctacctga tcaatgcatg tcgcggctcg gtcgtggatg agaatgcggt   7860
gatagcagca ctggcgtctg gaaaactagc tggatatgca gccgatgtct tcgagatgga   7920
agaatggata cgcgctgatc gcccgcaggc tatccccaag gcgctgctcg acaatacggc   7980
acaaacgttt tttacgccgc atttgggatc ggcggtcaag gaagttcggc ttgaaatcga   8040
gcggcaggca gcgatgaaca tcatccaggc actcgctggt gaaaaaccga tgggcgcgat   8100
taatcagccg tatccgggag taaaggcggc gtgaaagctt ggctgttttg cggatgaga    8160 gaagattttc agcctgatac agattaaatc agaacgcaga agcggtctga taaaacagaa   8220
tttgcctggc ggcagtagcg cggtggtccc acctgacccc atgccgaact cagaagtgaa   8280
acgccgtagc gccgatggta gtgtgggtc tccccatgcg agagtaggga actgccaggc    8340
atcaaataaa acgaaaggct cagtcgaaag actgggcctt tcgttttatc tgttgtttgt   8400
cggtgaacgc tctcctgagt aggacaaatc cgccgggagc ggatttgaac gttgcgaagc   8460
aacggcccgg agggtggcgg gcaggacgcc cgccataaac tgccaggcat caaattaagc   8520
agaaggccat cctgacggat ggcctttttg cgtttctaca aactctttt gtttatttt      8580 ctaaatacat tcaaatatgt atccgctcat gagacaataa ccctgataaa tgcttcaata   8640
atattgaaaa aggaagagta tgagtattca acatttccgt gtcgcccta ttccttttt      8700 tgcggcattt tgccttcctg ttttgctca cccagaaacg ctggtgaaag taaagatgc      8760 tgaagatcag ttgggtgcac gagtgggtta catcgaactg gatctcaaca gcggtaagat   8820
ccttgagagt tttcgccccg aagaacgttt tccaatgatg agcactttta agttctgct    8880 atgtggcgcg gtattatccc gtgttgacgc cgggcaagag caactcggtc gccgcataca   8940
ctattctcag aatgacttgg ttgagtatcg acgtggagtc gatcactgtg attggcgaag   9000
gggaaggcag cgctacccaa atcgctagct tgctggagaa gctgaaacaa accacgggca   9060
ttgatctggc gaaatcccta ccgggtcaat ccgactcgcc cgctgcgaag tcctaagaga   9120
tagcgatgtg accgcgatcg cttgtcaaga atcccagtga tcccgaacca taggaaggca   9180
```

```
agctcaatgc ttgcctcgtc ttgaggacta tctagatgtc tgtggaacgc acatttattg   9240
ccatcaagcc cgatggcgtt cagcggggtt tggtcggtac gatcatcggc cgctttgagc   9300
aaaaaggctt caaactggtg ggcctaaagc agctgaagcc cagtcgcgag ctggccgaac   9360
agcactatgc tgtccaccgc gagcgcccct tcttcaatgg cctcgtcgag ttcatcacct   9420
ctgggccgat cgtggcgatc gtcttggaag gcgaaggcgt tgtggcggct gctcgcaagt   9480
tgatcggcgc taccaatccg ctgacggcag aaccgggcac catccgtggt gattttggtg   9540
tcaatattgg ccgcaacatc atccatggct cggatgcaat cgaaacagca caacaggaaa   9600
ttgctctctg gtttagccca gcagagctaa gtgattggac ccccacgatt caaccctggc   9660
tgtacgaata aggtctgcat tccttcagag agacattgcc atgcccgtgc tgcgatcgcc   9720
cttccaagct gccttgcccc gctgtttcgg gctggcagcc ctggcgttgg ggctggcgac   9780
cgcttgccaa gaaagcagcg ctccaattcc ctatagtgag tcgtattaaa ttcgtaatca   9840
tggtcatagc tgtttcctgt gtgaaattgt tatccgctca caattccaca acatacga   9900
gccggaagca taaagtgtaa agcctggggt gcctaatgag tgagctaact cacattaatt   9960
gcgttgcgct cactgcccgc tttccagtcg ggaaacctgt cgtgccagct gcattaatga  10020
atcggccaac gcgcggggag aggcggtttg cgtattgggc gctcttccgc ttcctcgctc  10080
actgactcgc tgcgctcggt cgttcggctg cggcgagcgg tatcagctca ctcaaaggcg  10140
gtaatacggt tatccacaga atcagggat aacgcaggaa agaacatgtg agcaaaaggc  10200
cagcaaaagg ccaggaaccg taaaaaggcc gcgttgctgg cgtttttcca taggctccgc  10260
cccctgacag catcacaa aaatcgacgc tcaagtcaga ggtggcgaaa cccgacagga  10320
ctataaagat accaggcgtt tcccctgga agctccctcg tgcgctctcc tgttccgacc  10380
ctgccgctta ccggatacct gtccgccttt ctcccttcgg gaagcgtggc gctttctcat  10440
agctcacgct gtaggtatct cagttcggtg taggtcgttc gctccaagct gggctgtgtg  10500
cacgaacccc ccgttcagcc cgaccgctgc gccttatccg gtaactatcg tcttgagtcc  10560
aacccggtaa gacacgactt atcgccactg gcagcagcca ctggtaacag gattagcaga  10620
gcgaggtatg taggcggtgc tacagagttc ttgaagtggt ggcctaacta cggctacact  10680
agaaggacag tatttggtat ctgcgctctg ctgaagccag ttaccttcgg aaaaagagtt  10740
ggtagctctt gatccggcaa acaaaccacc gctggtagcg tggtttttt tgtttgcaag  10800
cagcagatta cgcgcagaaa aaaaggatct caagaagatc ctttgatctt ttctacgggg  10860
tctgacgctc agtggaacga aaactcacgt taagggattt tggtcatgag attatcaaaa  10920
aggatcttca cctagatcct tttaaattaa aaatgaagtt ttaaatcaat ctaaagtata  10980
tatgagtaaa cttggtctga cagttaccaa tgcttaatca gtgaggcacc tatctcagcg  11040
atctgtctat ttcgttcatc catagttgcc tgactccccg tcgtgtagat aactacgata  11100
cgggagggct taccatctgg ccccagtgct gcaatgatac cgcgagaccc acgctcaccg  11160
gctccagatt tatcagcaat aaaccagcca gccggaaggg ccgagcgcag aagtggtcct  11220
gcaactttat ccgcctccat ccagtctatt aattgttgcc gggaagctag agtaagtagt  11280
tcgccagtta atagtttgcg caacgttgtt gccattgcta caggcatcgt ggtgtcacgc  11340
tcgtcgtttg gtatggcttc attcagctcc ggttcccaac gatcaaggcg agttacatga  11400
tcccccatgt tgtgcaaaaa agcggttagc tccttcggtc ctccgatcgt tgtcagaagt  11460
aagttggccg cagtgttatc actcatggtt atggcagcac tgcataattc tcttactgtc  11520
atgccatccg taagatgctt ttctgtgact ggtgagtact caaccaagtc attctgagaa  11580
```

```
tagtgtatgc ggcgaccgag ttgctcttgc ccggcgtcaa tacgggataa taccgcgcca    11640
catagcagaa ctttaaaagt gctcatcatt ggaaaacgtt cttcggggcg aaaactctca    11700
aggatcttac cgctgttgag atccagttcg atgtaaccca ctcgtgcacc caactgatct    11760
tcagcatctt ttactttcac cagcgtttct gggtgagcaa aaacaggaag gcaaaatgcc    11820
gcaaaaaagg gaataagggc gacacggaaa tgttgaatac tcatactctt cctttttcaa    11880
tattattgaa gcatttatca gggttattgt ctcatgagcg gatacatatt tgaatgtatt    11940
tagaaaaata aacaaatagg ggttccgcgc acatttcccc gaaaagtgcc acctgacgcg    12000
ccctgtagcg gcgcattaag cgcggcgggt gtggtggtta cgcgcagcgt gaccgctaca    12060
cttgccagcg ccctagcgcc cgctcctttc gctttcttcc cttcctttct cgccacgttc    12120
gccggctttc cccgtcaagc tctaaatcgg ggcatccctt tagggttccg atttagtgct    12180
ttacggcacc tcgaccccaa aaaacttgat tagggtgatg gttcacgtag tgggccatcg    12240
ccctgataga cggttttttcg ccctttgacg ttggagtcca cgttctttaa tagtggactc    12300
ttgttccaaa ctggaacaac actcaaccct atctcggtct attcttttga tttataaggg    12360
attttgccga tttcggccta ttggttaaaa aatgagctga tttaacaaaa atttaacgcg    12420
aattttaaca aaatattaac aaaatattaa cgtttacaat tt                      12462

<210> SEQ ID NO 64
<211> LENGTH: 7661
<212> TYPE: DNA
<213> ORGANISM: Artificial Sequence
<220> FEATURE:
<223> OTHER INFORMATION: pSTVhtxAE

<400> SEQUENCE: 64
ctaggagcat caccatgttt gcagagcagc aacgcgaata tctcgacaag ggatatacga      60
agattgaaag cttttttctcc gcggaggaag tagcgaagat tcttgaagac gtcaagcaaa     120
ttgaattggg agctattggc gtagcttcgg acaatgagac ttaccagttc gaaaagaaga     180
atggcgagac gacgaagcta ctgcgtcgcg tcgagaatcc tcacctttat ttcgatgcaa     240
tagattcttt ggtcaggtcg gaaaaaatcg tcgatttgct tcggcatttc ctgggcgaaa     300
acatccgttt gcacaatagc aaaatcaact tcaagccgcc atcaggcgcg ccagtccagt     360
ggcatcagga ctgggcattc tatccccaca caaacgatga ttttcttact ctcggaattt     420
tcctcgacga gacaagtgag aaaaatggcg cgatggcatg cttgccaggc tcccacaaag     480
gaaaagtgta cgaccaccgg aacgtcgaga cgggcgagtt ttgccacgcg atctctcgct     540
ccaactggga cgaagcgctc gacccgacag aaggggagtt actgacggga cccgtaggaa     600
ctgtcacgtt gcatcacgtc cggacccttc atggttcagg cccaaaccac tcaacgatca     660
ggcggcgttt tctgctcatc ggctatgccg cggctgatgc ctggccactt ctgggctgtg     720
gcaactatgg ggattatgaa agcctcatgg tctctggccg atccaccgta ttcccgcgca     780
tggtggaact ccctttgact gtcccgtatc cgttgtcgat gtacggtgat cgcatctttg     840
aaagtcaacg agctttgact caaaagtact actgaagtct ttaactcact gaggtcataa     900
tgcaagtttt tactctgttt tcgaaattca agaaggcgtt aacgcgcgcc attcttgcct     960
ttatcgccac aatcatagtg tgcacacccg cgcaggcagc tgaggttgtc aatggtaaac    1020
ttcacctgcg ttttgcaatt gcgccgatgc gtccaacgcc tagccagacc atcaaagagt    1080
ttgagccgat attcaagtat ctcgccgacc agctcggcgc gacctatgaa atcgtctccc    1140
```

```
cggaaagctg gcggcaata tctgtggcaa tgacaaatgg ccatgtcgat gtgggctggc    1200
tcggaccctg ggctatgtc ttgtcgaata aaaaggccgg caccgaagtg cttgcaacgg    1260
tcaagtaccg cggggagccg ttctacaaag ccctcattgt cggtcgcgcc gatctgccga    1320
tcaaaaaatg gcccgaggac gcgaagggtt gaagctgtc actcagtgat cagggcaaca    1380
cttctggctg gctcatcccg atggcgtact tcaagagcat cggcatcgac cctgcgagct    1440
attttgaata tcgtgaaggt gccacgtttg gccagaacga atcacagatt cagcacggac    1500
tgatcgacct cggatccgat atggatcggg gccggaacgg gatgatcgaa gcgggtcaaa    1560
tcgatccttc gaagtccaag atcgtgtggg aatccagcaa gctgccgaac gacgcgatat    1620
ccgtgccgaa ggattttgat cctgctctga agcgcgcat cacggaaata ctgacgtcct    1680
tgtccgaaga gaaagcacag tcgctgatgg gctcgggcta taacggcttc gtgaaggcaa    1740
agcacagcga ttacaaggta atcgaagacg ccggccgcat cctgggaaaa ctgtaaagca    1800 cgagggggtcc gttcttggat gagggcagcg gacgacaagg tggactgacg cacgccagct    1860
ccttgtctcc gctgcacgaa catacggcg cgcatcgcaa taccacagag gatgaaccaa    1920
tgaatcagcg aatcgaagaa gtcatgctgg ctaatgtcaa gagggacgta gccaggagaa    1980
agcggcattt tgcaacgtcg gtcgtagtac tcagtttgct ggcagtggcc tggtacgtgt    2040
gtcagataga attccagaag ctaggcgccg gtttaccgag actatggtca ttcgtcgtgc    2100
agatgtttcc acccgacctg agcgacctgg acgtcattct aaaagggggct ggcgagacgc    2160 tcgccatggc gacgattggc acgatattcg ccacaatcat tgcatttccg ctggcactca    2220
tggctgcgcg taatacctgt ccgaacaagt ggacctatcg ggtatcccgc gccatcctga    2280
acgccagccg cggcacggag acatttgtct atgcacttgt atttgtagca gcagtgggct    2340
tcggtccgtt ctccggcgta ctggccatta cttttccacat ggtaggggca atcggcaaaa    2400
tgtttgctga agccatcgag cccgttgacc aagggccgtt ggatgcgctc gccttgaccg    2460
gtgccagcag ggcaaagatt atccgctacg gtctgatccc ggatgttatg ccgcacctga    2520
tcgcgagcgt tctatacatt tgggaattca gtgtcagaac gtccacagta ctgggcatcg    2580
taggcgcagg tggaattggg cagaccctga aagatactgt ggacttgttg gaattcaaca    2640
agatgattac ggtactggcg gttgtattgc tgatggtgtc ggcaatcgat ttcatcagtg    2700
accggctcag gtacttgata ttggacacaa aacgcgaggg attcgaaact ctccctgcga    2760
ataactgatt gcttcacgta ttactggaag ggaggttcgc aatgaaagat gtagcgttgc    2820
agttaaagaa tgtcggtaag tcatacggca ataaagttgt cctggaatcg attgacttcg    2880
aagtacgtca cggctcaatg gttgccttgc tcggcacaag cggggcaggg aagtcgacgc    2940
ttttccgatg tctcactggc cttgagccga ttgactccgg ttctatcgtg gcgctcggag    3000
aatccataca tgaactgtct ccggcgcgtc tgcgggcagt acgtggccag atcgggttcg    3060
tgttccaaca actgcacctg gtgaaaaggt tctcagcact cgagaatgta ttgggtgcgc    3120
gtctggcaga gatgcccatt tggcgcgtca cattgaaaag cttcagccgg gctgacaaag    3180
tgctcgcgtt cgaatgtctg gaccgggtcg gcatgctcga ttatgcaaac acgcctacgc    3240
aactgctgtc aggcggtcag caacagcgta ttgcgatagc gcgagccttg gcgcagaagc    3300
ccaagattat tattgcggac gaacccgtct ccagcctcga tccgctgacg gcgcgctcgg    3360
ttctgcaaac gctgaaagcc gcggctacag atcttaatgt cgccggtcctg tgcagcctgc    3420 accaggtaga cctggcccgt gagtttggcg accgcatcgt gggcatgcgc gacggacgtg    3480
tcgttttcga cggcacgcca gcggaattca ccgacgagcg cgtgcatgcg ctttaccagg    3540
```

```
gtgcccgctg ggaagatgca ccagcggccg agagcgacgc gcagcactcg gtggccggtc    3600
tggctgtggc atgaggggcg aagcgatgac cacatccaca cgccccatac ccgtgccgcc    3660
ccagggcacc gcactgcact ggcacctgag cgcgccctac aacgccaaac atctgctggt    3720
gctgatcgcc gtcatggtgc tgttgttcgt gaccggacaa cgcaccgaaa tggaccgcat    3780
ggtggccatg acggcacagg ccgtggccaa gaccgtgggc ctggctgacg attcacaagt    3840
cgcgcgcggc ttgtcgcgcg tcggtcaagc catgtggcca cccgccatcg cagaaaccga    3900
agaggtgggc cggattcagg acctggatcg ccagaagctg cccctgttct cgcacatcga    3960
gacccaggag cgcgtcgagc agaagatgaa tctggacacg ctgaagatgg aagccacgac    4020
ggaaaccgtc gaagtgctgg tcaagccggt cggctatgtc tggacggttt tcatcaagat    4080
gatcgagacc ctggagattg cgctgtgggg cacgatcctg tcggtgctgg tgtcgattcc    4140
cctggcgtat ttcgcggccc gcaactacta gccccaaccg ttttacctac accgctgccc    4200
gcggcaccat cagtctgctg cgttcagcgc cggaactcat cgtcgctttg ttcctggtgc    4260
tggcctacgg ctttggcccc atcgctggcg tgctggcgct gggcctgcat gcggccggct    4320
tcctgggcaa gttctacgcc gaggacatcg agaacgccga caagaagccg caagaggcgc    4380
tggaggccat cggcgcgggc aagctcaaga cgctgtggta cggcgtcatc ccccaggtct    4440
tgccgcaata catcgcctac accgcctaca tcctggaccg caacctgcgc atggccaccg    4500
tcatcggtct ggtgggcgcg gcggcatcg gccaggaact caagggccgt tttgacatgt    4560
tccagtacgg ccatgtcatg accatcctga tcgcgatctt cgtctttgtg ttcgtgctgg    4620
accagttgca ggcgcgcatc cgcgccaagc tgatctgaga tcctctagag tcgacctgca    4680
ggcatgcaag cttggcactg gccgtcgttt tacaacgtcg tgactgggaa aaccctggcg    4740
ttacccaact taatcgcctt gcagcacatc cccctttcgc cagctggcgt aatagcgaag    4800
aggcccgcac cgatcgccct tcccaacagt tgcgcagcct gaatggcgaa tgagcttatc    4860
gatgataagc tgtcaaacat gagaattaca acttatatcg tatgggctga cttcaggtg    4920
ctacatttga agagataaat tgcactgaaa tctagaaata ttttatctga ttaataagat    4980
gatcttcttg agatcgtttt ggtctgcgcg taatctcttg ctctgaaaac gaaaaaaccg    5040
ccttgcaggg cggttttttcg aaggttctct gagctaccaa ctctttgaac cgaggtaact    5100
ggcttggagg agcgcagtca ccaaaacttg tcctttcagt ttagccttaa ccggcgcatg    5160
acttcaagac taactcctct aaatcaatta ccagtggctg ctgccagtgg tgcttttgca    5220
tgtctttccg ggttggactc aagacgatag ttaccggata aggcgcagcg gtcggactga    5280
acgggggggtt cgtgcataca gtccagcttg gagcgaactg cctacccgga actgagtgtc    5340
aggcgtggaa tgagacaaac gcggccataa cagcggaatg acaccggtaa accgaaaggc    5400
aggaacagga gagcgcacga gggagccgcc aggggaaacg cctggtatct ttatagtcct    5460
gtcgggtttc gccaccactg atttgagcgt cagatttcgt gatgcttgtc aggggggcgg    5520
agcctatgga aaaacggctt tgccgcggcc ctctcacttc cctgttaagt atcttcctgg    5580
catcttccag gaaatctccg ccccgttcgt aagccatttc cgctcgccgc agtcgaacga    5640
ccgagcgtag cgagtcagtg agcgaggaag cggaatatat cctgtatcac atattctgct    5700
gacgcaccgg tgcagccttt tttctcctgc cacatgaagc acttcactga caccctcatc    5760
agtgccaaca gtaagcca gtatacactc cgctagcgct gatgtccggc ggtgcttttg    5820
ccgttacgca ccacccccgtc agtagctgaa caggagggac agctgataga aacagaagcc    5880
```

| | |
|---|---|
| actggagcac ctcaaaaaca ccatcataca ctaaatcagt aagttggcag catcacccga | 5940 |
| cgcactttgc gccgaataaa tacctgtgac ggaagatcac ttcgcagaat aaataaatcc | 6000 |
| tggtgtccct gttgataccg ggaagccctg gccaacttt tggcgaaaat gagacgttga | 6060 |
| tcggcacgta agaggttcca actttcacca taatgaaata agatcactac cgggcgtatt | 6120 |
| ttttgagtta tcgagatttt caggagctaa ggaagctaaa atggagaaaa aaatcactgg | 6180 |
| atataccacc gttgatatat cccaatggca tcgtaaagaa catttgagg catttcagtc | 6240 |
| agttgctcaa tgtacctata accagaccgt tcagctggat attacggcct ttttaaagac | 6300 |
| cgtaaagaaa aataagcaca agttttatcc ggcctttatt cacattcttg cccgcctgat | 6360 |
| gaatgctcat ccggaatttc gtatggcaat gaaagacggt gagctggtga tatgggatag | 6420 |
| tgttcaccct tgttacaccg ttttccatga gcaaactgaa acgttttcat cgctctggag | 6480 |
| tgaataccac gacgatttcc ggcagtttct acacatatat tcgcaagatg tggcgtgtta | 6540 |
| cggtgaaaac ctggcctatt tccctaaagg gtttattgag aatatgtttt tcgtctcagc | 6600 |
| caatccctgg gtgagtttca ccagttttga tttaaacgtg gccaatatgg acaacttctt | 6660 |
| cgccccgtt ttcaccatgg gcaaatatta tacgcaaggc gacaaggtgc tgatgccgct | 6720 |
| ggcgattcag gttcatcatg ccgtttgtga tggcttccat gtcggcagaa tgcttaatga | 6780 |
| attacaacag tactgcgatg agtggcaggg cggggcgtaa tttttttaag gcagttattg | 6840 |
| gtgcccttaa acgcctggtg ctacgcctga ataagtgata taagcggat gaatggcaga | 6900 |
| aattcgaaag caaattcgac ccggtcgtcg gttcagggca gggtcgttaa atagccgctt | 6960 |
| atgtctattg ctggtttacc ggtttattga ctaccggaag cagtgtgacc gtgtgcttct | 7020 |
| caaatgcctg aggccagttt gctcaggctc tccccgtgga ggtaataatt gacgatatga | 7080 |
| tcatttattc tgcctcccag agcctgataa aaacggttag cgcttcgtta atacagatgt | 7140 |
| aggtgttcca cagggtagcc agcagcatcc tgcgatgcag atccggaaca taatggtgca | 7200 |
| gggcgcttgt ttcggcgtgg gtatggtggc aggcccgtg gccggggac tgtttgggcgc | 7260 |
| tgccggcacc tgtcctacga gttgcatgat aaagaagaca gtcataagtg cggcgacgat | 7320 |
| agtcatgccc cgcgcccacc ggaaggagct accggacagc ggtgcggact gttgtaactc | 7380 |
| agaataagaa atgaggccgc tcatggcgtt ccaatacgca aaccgcctct ccccgcgcgt | 7440 |
| tggccgattc attaatgcag ctggcacgac aggtttcccg actggaaagc gggcagtgag | 7500 |
| cgcaacgcaa ttaatgtgag ttagctcact cattaggcac cccaggcttt acactttatg | 7560 |
| cttccggctc gtatgttgtg tggaattgtg agcggataac aatttcacac aggaaacagc | 7620 |
| tatgaccatg attacgaatt cgagctcggt acccggggat c | 7661 |

<210> SEQ ID NO 65
<211> LENGTH: 13193
<212> TYPE: DNA
<213> ORGANISM: Artificial Sequence
<220> FEATURE:
<223> OTHER INFORMATION: pNShtxBCDE-ptxD

<400> SEQUENCE: 65

| | |
|---|---|
| cccattcgcc attcaggctg cgcaactgtt gggaagggcg atcggtgcgg gcctcttcgc | 60 |
| tattacgcca gctggcgaaa ggggggatgtg ctgcaaggcg attaagttgg gtaacgccag | 120 |
| ggttttccca gtcacgacgt tgtaaaacga cggccagtgc caagctaaaa gcgctccgca | 180 |
| tggatctgac caacatgatc attgagttgc gcgtttccaa tgccttctcc aagggcggca | 240 |
| ttccccctgac tgttgaaggc gttgccaata tcaagattgc tggggaagaa ccgaccatcc | 300 |

```
acaacgcgat cgagcggctg cttggcaaaa accgtaagga aatcgagcaa attgccaagg    360
agaccctcga aggcaacttg cgtggtgttt tagccagcct cacgccggag cagatcaacg    420
aggacaaaat tgccttttgcc aaaagtctgc tggaagaggc ggaggatgac cttgagcagc   480
tgggtctagt cctcgatacg ctgcaagtcc agaacatttc cgatgaggtc ggttatctct    540
cggctagtgg acgcaagcag cgggctgatc tgcagcgaga tgcccgaatt gctgaagccg    600
atgcccaggc tgcctctgcg atccaaacgg ccgaaaatga caagatcacg gccctgcgtc    660
ggatcgatcg cgatgtagcg atcgcccaag ccgaggccga gcgccggatt caggatgcgt    720
tgacgcggcg cgaagcggtg gtggccgaag ctgaagcgga cattgctacc gaagtcgctc    780
gtagccaagc agaactccct gtgcagcagg agcggatcaa acaggtgcag cagcaacttc    840
aagccgatgt gatcgcccca gctgaggcag cttgtaaacg ggcgatcgcg gaagcgcggg    900
gggccgccgc ccgtatcgtc gaagatggaa aagctcaagc ggaagggacc caacggctgg    960
cggaggcttg gcagaccgct ggtgctaatg cccgcgacat cttcctgctc cagaagctcg   1020
actatgcttg taaaccgttt tgtgaaaaaa tttttaaaat aaaaaagggg acctctaggg   1080
tccccaatta attagtaata taatctatta aaggtcattc aaaaggtcat ccaccggatc   1140
agcttagtaa agccctcgct agattttaat gcggatgttg cgattacttc gccaactatt   1200
gcgataacaa gaaaaagcca gcctttcatg atatatctcc caatttgtgt agggcttatt   1260
atgcacgctt aaaaataata aaagcagact tgacctgata gtttggctgt gagcaattat   1320
gtgcttagtg catctaacgc ttgagttaag ccgcgccgcg aagcggcgtc ggcttgaacg   1380
aattgttaga cattatttgc cgactacctt ggtgatctcg cctttcacgt agtggacaaa   1440
ttcttccaac tgatctgcgc gcgaggccaa gcgatcttct tcttgtccaa gataagcctg   1500
tctagcttca agtatgacgg gctgatactg ggccggcagg cgctccattg cccagtcggc   1560
agcgacatcc ttcggcgcga ttttgccggt tactgcgctg taccaaatgc gggacaacgt   1620
aagcactaca tttcgctcat cgccagccca gtcgggcggc gagttccata gcgttaaggt   1680
ttcatttagc gcctcaaata gatcctgttc aggaaccgga tcaaagagtt cctccgccgc   1740
tggacctacc aaggcaacgc tatgttctct tgcttttgtc agcaagatag ccagatcaat   1800
gtcgatcgtg gctggctcga agatacctgc aagaatgtca ttgcgctgcc attctccaaa   1860
ttgcagttcg cgcttagctg gataacgcca cggaatgatg tcgtcgtgca caacaatggt   1920
gacttctaca gcgcggagaa tctcgctctc tccaggggaa gccgaagttt ccaaaaggtc   1980
gttgatcaaa gctcgccgcg ttgtttcatc aagccttacg gtcaccgtaa ccagcaaatc   2040
aatatcactg tgtggcttca ggccgccatc cactgcggag ccgtacaaat gtacggccag   2100
caacgtcggt tcgagatggc gctcgatgac gccaactacc tctgatagtt gagtcgatac   2160
ttcggcgatc accgcttccc tcatgatgtt taactttgtt ttagggcgac tgccctgctg   2220
cgtaacatcg ttgctgctcc ataacatcaa acatcgaccc acggcgtaac gcgcttgctg   2280
cttggatgcc cgaggcatag actgtacccc aaaaaaacag tcataacaag ccatgaaaac   2340
cgccactgcg ccgttaccac cgctgcgttc ggtcaaggtt ctggaccagt tgcgtgagcg   2400
catacgctac ttgcattaca gcttacgaac cgaacaggct tatgtccact gggttcgtgc   2460
cttcatccgt ttccacggtg tgcgtcaccc ggcaaccttg ggcagcagcg aagtcgaggc   2520
atttctgtcc tggctggcga acgagcgcaa ggtttcggtc tccacgcatc gtcaggcatt   2580
ggcggccttg ctgttcttct acggcaaggt gctgtgcacg gatctgccct ggcttcagga   2640
```

```
gatcggaaga cctcggccgt cgcggcgctt gccggtggtg ctgaccccgg atgaagtggt    2700
tcgcatcctc ggttttctgg aaggcgagca tcgtttgttc gcccagcttc tgtatggaac    2760
gggcatgcgg atcagtgagg gtttgcaact gcgggtcaag gatctggatt tcgatcacgg    2820
cacgatcatc gtgcgggagg gcaagggctc caaggatcgg gccttgatgt tacccgagag    2880
cttggcaccc agcctgcgcg agcaggggaa ttgatccggt ggatgacctt tgaatgacc     2940 tttaatagat tatattacta attaattggg gaccctagag gtccccttttt ttatttttaaa  3000 aattttttca caaaacggtt tacaagcata gtcgagttac gttgacacca tcgaatggtg    3060
caaaaccttt cgcggtatgg catgatagcg cccggaagag agtcaattca gggtggtgaa    3120
tgtgaaacca gtaacgttat acgatgtcgc agagtatgcc ggtgtctctt atcagaccgt    3180
ttcccgcgtg gtgaaccagg ccagccacgt ttctgcgaaa acgcgggaaa aagtggaagc    3240
ggcgatggcg gagctgaatt acattcccaa ccgcgtggca caacaactgg cgggcaaaca    3300
gtcgttgctg attggcgttg ccacctccag tctggccctg cacgcgccgt cgcaaattgt    3360
cgcggcgatt aaatctcgcg ccgatcaact gggtgccagc gtggtggtgt cgatggtaga    3420
acgaagcggc gtcgaagcct gtaaagcggc ggtgcacaat cttctcgcgc aacgcgtcag    3480
tgggctgatc attaactatc cgctggatga ccaggatgcc attgctgtgg aagctgcctg    3540
cactaatgtt ccggcgttat ttcttgatgt ctctgaccag acacccatca acagtattat    3600
tttctcccat gaagacggta cgcgacgggc gtggagcatc tggtcgcatt gggtcaccag    3660
caaatcgcgc tgttagcggg cccattaagt tctgtctcgg cgcgtctgcg tctggctggc    3720
tggcataaat atctcactcg caatcaaatt cagccgatag cggaacggga aggcgactgg    3780
agtgccatgt ccggttttca acaaaccatg caaatgctga atgagggcat cgttcccact    3840
gcgatgctgt ttgccaacga tcagatgcg ctgggcgcaa tgcgcgccat taccgagtcc     3900
gggctgcgcg ttggtgcgga tatctcggta gtgggatacg acgataccga agacagctca    3960
tgttatatcc cgccgttaac caccatcaaa caggattttc gcctgctggg gcaaaccagc    4020
gtggaccgct tgctgcaact ctctcagggc caggcggtga agggcaatca gctgttgccc    4080
gtctcactgg tgaaaagaaa aaccaccctg gcgcccaata cgcaaaccgc ctctccccgc    4140
gcgttggccg attcattaat gcagctggca cgacaggttt cccgactgga aagcgggcag    4200
tgagcgcaac gcaattaatg tgagttagcg cgaattgatc tggtttgaca gcttatcatc    4260
gactgcacgg tgcaccaatg cttctggcgt caggcagcca tcggaagctg tggtatggct    4320
gtgcaggtcg taaatcactg cataattcgt gtcgctcaag gcgcactccc gttctggata    4380
atgttttttg cgccgacatc ataacggttc tggcaaatat tctgaaatga gctgttgaca    4440
attaatcatc cggctcgtat aatgtgtgga attgtgagcg gataacaatt tcacacagga    4500
aacagaccat ggaattcatg caagttttta ctctgttttc gaaattcaag aaggcgttaa    4560
cgcgcgccat tcttgccttt atcgccacaa tcatagtgtg cacacccgcg caggcagctg    4620
aggttgtcaa tggtaaactt cacctgcgtt ttgcaattgc gccgatgcgt ccaacgccta    4680
gccagaccat caaagagttt gagccgatat tcaagtatct cgccgaccag ctcggcgcga    4740
cctatgaaat cgtctccccg gaaagctggg cggcaatatc tgtggcaatg acaaatggcc    4800
atgtcgatgt gggctggctc ggaccctggg gctatgtctt gtcgaataaa aaggccggca    4860
ccgaagtgct tgcaacggtc aagtaccgcg gggagccgtt ctacaaagcc ctcattgtcg    4920
gtcgcgccga tctgccgatc aaaaaatggc ccgaggacgc gaagggtttg aagctgtcac    4980
tcagtgatca gggcaacact tctggctggc tcatcccgat ggcgtacttc aagagcatcg    5040
```

```
gcatcgaccc tgcgagctat tttgaatatc gtgaaggtgc cacgtttggc cagaacgaat    5100
cacagattca gcacggactg atcgacctcg gatccgatat ggatcggggc cggaacggga    5160
tgatcgaagc gggtcaaatc gatccttcga agtccaagat cgtgtgggaa tccagcaagc    5220
tgccgaacga cgcgatatcc gtgccgaagg attttgatcc tgctctgaaa gcgcgcatca    5280
cggaaatact gacgtccttg tccgaagaga aagcacagtc gctgatgggc tcgggctata    5340
acggcttcgt gaaggcaaag cacagcgatt acaaggtaat cgaagacgcc ggccgcatcc    5400
tgggaaaact gtaaagcacg aggggtccgt tcttggatga gggcagcgga cgacaaggtg    5460
gactgacgca cgccagctcc ttgtctccgc tgcacgaaca tacgggcgcg catcgcaata    5520
ccacagagga tgaaccaatg aatcagcgaa tcgaagaagt catgctggct aatgtcaaga    5580
gggacgtagc caggagaaag cggcattttg caacgtcggt cgtagtactc agtttgctgg    5640
cagtggcctg gtacgtgtgt cagatagaat tccagaagct aggcgccggt ttaccgagac    5700
tatggtcatt cgtcgtgcag atgttttccac ccgacctgag cgacctggac gtcattctaa    5760
aaggggctgg cgagacgctc gccatggcga cgattggcac gatattcgcc acaatcattg    5820
catttccgct ggcactcatg gctgcgcgta atacctgtcc gaacaagtgg acctatcggg    5880
tatcccgcgc catcctgaac gccagccgcg gcacggagac atttgtctat gcacttgtat    5940
ttgtagcagc agtgggcttc ggtccgttct ccggcgtact ggccattact ttccacatgg    6000 tagggcaat cggcaaaatg tttgctgaag ccatcgagcc cgttgaccaa gggccgttgg    6060
atgcgctcgc cttgaccggt gccagcaggg caaagattat ccgctacggt ctgatcccgg    6120
atgttatgcc gcacctgatc gcgagcgttc tatacatttg ggaattcagt gtcagaacgt    6180
ccacagtact gggcatcgta ggcgcaggtg gaattgggca gaccctgaaa gatactgtgg    6240
acttgttgga attcaacaag atgattacgg tactggcggt tgtattgctg atggtgtcgg    6300
caatcgattt catcagtgac cggctcaggt acttgatatt ggacacaaaa cgcgagggat    6360
tcgaaactct ccctgcgaat aactgattgc ttcacgtatt actggaaggg aggttcgcaa    6420
tgaaagatgt agcgttgcag ttaaagaatg tcggtaagtc atacggcaat aaagttgtcc    6480
tggaatcgat tgacttcgaa gtacgtcacg gctcaatggt tgccttgctc ggcacaagcg    6540
gggcagggaa gtcgacgctt ttccgatgtc tcactggcct tgagccgatt gactccggtt    6600
ctatcgtggc gctcggagaa tccatacatg aactgtctcc ggcgcgtctg cgggcagtac    6660
gtggccagat cgggttcgtg ttccaacaac tgcacctggt gaaaaggttc tcagcactcg    6720
agaatgtatt gggtgcgcgt ctggcagaga tgcccatttg gcgcgtcaca ttgaaaagct    6780
tcagccgggc tgacaaagtg ctcgcgttcg aatgtctgga ccgggtcggc atgctcgatt    6840
atgcaaacac gcctacgcaa ctgctgtcag gcggtcagca acagcgtatt gcgatagcgc    6900
gagccttggc gcagaagccc aagattatta ttgcggacga acccgtctcc agcctcgatc    6960
cgctgacggc gcgctcggtt ctgcaaacgc tgaaagccgc ggctacagat cttaatgtcg    7020
cggtcctgtg cagcctgcac caggtagacc tggcccgtga gtttggcgac cgcatcgtgg    7080
gcatgcgcga cggacgtgtc gttttcgacg gcacgccagc ggaattcacc gacgagcgcg    7140
tgcatgcgct ttaccagggt gcccgctggg aagatgcacc agcggccgag agcgacgcgc    7200
agcactcggt ggccggtctg gctgtggcat gaggggcgaa gcgatgacca catccacacg    7260
ccccataccc gtgccgcccc agggcaccgc actgcactgg cacctgagcg cgccctacaa    7320
cgccaaacat ctgctggtgc tgatcgccgt catggtgctg ttgttcgtga ccggacaacg    7380
```

```
caccgaaatg gaccgcatgg tggccatgac ggcacaggcc gtggccaaga ccgtgggcct    7440
ggctgacgat tcacaagtcg cgcgcggctt gtcgcgcgtc ggtcaagcca tgtggccacc    7500
cgccatcgca gaaaccgaag aggtgggccg gattcaggac ctggatcgcc agaagctgcc    7560
cctgttctcg cacatcgaga cccaggagcg cgtcgagcag aagatgaatc tggacacgct    7620
gaagatggaa gccacgacgg aaaccgtcga agtgctggtc aagccggtcg gctatgtctg    7680
gacggttttc atcaagatga tcgagaccct ggagattgcg ctgtggggca cgatcctgtc    7740
ggtgctggtg tcgattcccc tggcgtattt cgcggcccgc aactactagt cgacgccttc    7800
agctccttcc tgcgtcgcaa gttcaaataa ctcccaaagc ttacaaaggt ttttatgaag    7860
cccaaagtcg tcctcaccca ctgggtgcac ccggaaatca tcgaattgtt gtccgctagc    7920
gccgatgtta tccccaacac cacacgggaa accttgccgc gttctgaggt aattgcgcga    7980
gccaaagatg cggatgcact catggctttc atgccggaca gcatcgacag cgcgtttctc    8040
gaggaatgtc caaagctgcg tgtcatcggc gccgcgctta aaggctatga taacttcgat    8100
gtcaacgcct gcacacgcca cggtgtatgg cttacgattg tgccggattt gcttacgatc    8160
ccgaccgctg aactgactat cggccttctt ctcggtttga caaggcatat gctggaaggc    8220
gataggcaaa tccgtagcgg acacttccaa ggctggcggc cgacactata tggctctggt    8280
ttgacaggaa aaacgcttgg catcattggt atggggcgg tcggccgtgc aatcgcccag    8340
cgcttggctg gctttgaaat gaatctcttg tattgcgatc cgattccgct caatgccgaa    8400
caagaaaagg cttggcacgt acagcgcgtc acgctcgatg aactgctcga aaaatgtgat    8460
tatgtcgtgc cgatggttcc gatggccgca gagacactgc atctgatcga tgccaccgcg    8520
ttggccaaga tgaaaaccgg tagctacctg atcaatgcat gtcgcggctc ggtcgtggat    8580
gagaatgcgc tgatagcagc actggcgtct ggaaaactag ctggatatgc agccgatgtc    8640
ttcgagatgg aagaatggat acgcgctgat cgcccgcagg ctatccccaa ggcgctgctc    8700
gacaatacgc cacaaacgtt ttttacgccg catttgggat cggcggtcaa ggaagttcgg    8760
cttgaaatcg agcggcaggc agcgatgaac atcatccagg cactcgctgg tgaaaaaccg    8820
atgggcgcga ttaatcagcc gtatccggga gtaaaggcgg cgtgaaagct ggctgtttt    8880
ggcggatgag agaagatttt cagcctgata cagattaaat cagaacgcag aagcggtctg    8940
ataaaacaga atttgcctgg cggcagtagc gcggtggtcc cacctgaccc catgccgaac    9000
tcagaagtga aacgccgtag cgccgatggt agtgtggggt ctccccatgc gagagtaggg    9060
aactgccagc catcaaataa acgaaaggc tcagtcgaaa gactgggcct ttcgttttat    9120
ctgttgtttg tcggtgaacg ctctcctgag taggacaaat ccgccgggag cggatttgaa    9180
cgttgcgaag caacggcccg gagggtggcg ggcaggacgc ccgccataaa ctgccaggca    9240
tcaaattaag cagaaggcca tcctgacgga tggccttttt gcgtttctac aaactctttt    9300
tgtttatttt tctaaataca ttcaaatatg tatccgctca tgagacaata accctgataa    9360
atgcttcaat aatattgaaa aaggaagagt atgagtattc aacatttccg tgtcgccctt    9420
attcccttt ttgcggcatt ttgccttcct gttttgctc acccagaaac gctggtgaaa    9480
gtaaaagatg ctgaagatca gttgggtgca cgagtgggtt acatcgaact ggatctcaac    9540
agcggtaaga tccttgagag ttttcgcccc gaagaacgtt ttccaatgat gagcactttt    9600
aaagttctgc tatgtggcgc ggtattatcc cgtgttgacg ccgggcaaga gcaactcggt    9660
cgccgcatac actattctca gaatgacttg gttgagtatc gacgtggagt cgatcactgt    9720
gattggcgaa ggggaaggca gcgctaccca aatcgctagc ttgctggaga agctgaaaca    9780
```

```
aaccacgggc attgatctgg cgaaatccct accgggtcaa tccgactcgc ccgctgcgaa    9840
gtcctaagag atagcgatgt gaccgcgatc gcttgtcaag aatcccagtg atcccgaacc    9900
ataggaaggc aagctcaatg cttgcctcgt cttgaggact atctagatgt ctgtggaacg    9960
cacatttatt gccatcaagc ccgatggcgt tcagcgcggg ttggtcggta cgatcatcgg   10020
ccgctttgag caaaaaggct tcaaactggt gggcctaaag cagctgaagc ccagtcgcga   10080
gctggccgaa cagcactatg ctgtccaccg cgagcgcccc ttcttcaatg gcctcgtcga   10140
gttcatcacc tctgggccga tcgtggcgat cgtcttggaa ggcgaaggcg ttgtggcggc   10200
tgctcgcaag ttgatcggcg ctaccaatcc gctgacggca gaaccgggca ccatccgtgg   10260
tgattttggt gtcaatattg gccgcaacat catccatggc tcggatgcaa tcgaaacagc   10320
acaacaggaa attgctctct ggtttagccc agcagagcta agtgattgga cccccacgat   10380
tcaaccctgg ctgtacgaat aaggtctgca ttccttcaga gagacattgc catgcccgtg   10440
ctgcgatcgc ccttccaagc tgccttgccc cgctgtttcg ggctggcagc cctggcgttg   10500
gggctggcga ccgcttgcca agaaagcagc gctccaattc cctatagtga gtcgtattaa   10560
attcgtaatc atggtcatag ctgtttcctg tgtgaaattg ttatccgctc acaattccac   10620
acaacatacg agccggaagc ataaagtgta agcctggggt gcctaatga gtgagctaac   10680
tcacattaat tgcgttgcgc tcactgcccg ctttccagtc gggaaacctg tcgtgccagc   10740
tgcattaatg aatcggccaa cgcgcgggga gaggcggttt gcgtattggg cgctcttccg   10800
cttcctcgct cactgactcg ctgcgctcgg tcgttcggct gcggcgagcg gtatcagctc   10860
actcaaaggc ggtaatacgg ttatccacag aatcagggga taacgcagga agaacatgt   10920
gagcaaaagg ccagcaaaag gccaggaacc gtaaaaaggc cgcgttgctg gcgtttttcc   10980
ataggctccg cccccctgac gagcatcaca aaaatcgacg ctcaagtcag aggtggcgaa   11040
acccgacagg actataaaga taccaggcgt ttccccctgg aagctccctc gtgcgctctc   11100
ctgttccgac cctgccgctt accggatacc tgtccgcctt tctcccttcg ggaagcgtgg   11160
cgctttctca tagctcacgc tgtaggtatc tcagttcggt gtaggtcgtt cgctccaagc   11220
tgggctgtgt gcacgaaccc cccgttcagc ccgaccgctg cgccttatcc ggtaactatc   11280
gtcttgagtc aacccggta agacacgact tatcgccact ggcagcagcc actggtaaca   11340
ggattagcag agcgaggtat gtaggcggtg ctacagagtt cttgaagtgg tggcctaact   11400
acggctacac tagaaggaca gtatttggta tctgcgctct gctgaagcca gttaccttcg   11460
gaaaaagagt tggtagctct tgatccggca acaaaccac cgctggtagc ggtggttttt   11520
ttgtttgcaa gcagcagatt acgcgcagaa aaaaggatc tcaagaagat cctttgatct   11580
tttctacggg gtctgacgct cagtggaacg aaaactcacg ttaagggatt ttggtcatga   11640
gattatcaaa aaggatcttc acctagatcc ttttaaatta aaaatgaagt tttaaatcaa   11700
tctaaagtat atatgagtaa acttggtctg acagttacca atgcttaatc agtgaggcac   11760
ctatctcagc gatctgtcta tttcgttcat ccatagttgc ctgactcccc gtcgtgtaga   11820
taactacgat acgggagggc ttaccatctg gccccagtgc tgcaatgata ccgcgagacc   11880
cacgctcacc ggctccagat ttatcagcaa taaaccagcc agccggaagg gccgagcgca   11940
gaagtggtcc tgcaacttta tccgcctcca tccagtctat taattgttgc cgggaagcta   12000
gagtaagtag ttcgccagtt aatagtttgc gcaacgttgt tgccattgct acaggcatcg   12060
tggtgtcacg ctcgtcgttt ggtatggctt cattcagctc cggttcccaa cgatcaaggc   12120
```

```
gagttacatg atccccatg ttgtgcaaaa aagcggttag ctccttcggt cctccgatcg   12180
ttgtcagaag taagttggcc gcagtgttat cactcatggt tatggcagca ctgcataatt   12240
ctcttactgt catgccatcc gtaagatgct tttctgtgac tggtgagtac tcaaccaagt   12300
cattctgaga atagtgtatg cggcgaccga gttgctcttg cccggcgtca atacgggata   12360
ataccgcgcc acatagcaga actttaaaag tgctcatcat tggaaaacgt tcttcggggc   12420
gaaaactctc aaggatctta ccgctgttga tccagttc gatgtaaccc actcgtgcac   12480
ccaactgatc ttcagcatct tttactttca ccagcgtttc tgggtgagca aaaacaggaa   12540
ggcaaaatgc cgcaaaaaag gaataaggg cgacacggaa atgttgaata ctcatactct   12600
tcctttttca atattattga agcatttatc agggttattg tctcatgagc ggatacatat   12660
ttgaatgtat ttagaaaaat aaacaaatag gggttccgcg cacatttccc cgaaaagtgc   12720
cacctgacgc gccctgtagc ggcgcattaa gcgcggcggg tgtggtggtt acgcgcagcg   12780
tgaccgctac acttgccagc gccctagcgc ccgctccttt cgctttcttc ccttcctttc   12840
tcgccacgtt cgccggcttt ccccgtcaag ctctaaatcg ggcatccct ttagggttcc   12900
gatttagtgc tttacggcac ctcgacccca aaaaacttga ttagggtgat ggttcacgta   12960
gtgggccatc gccctgatag acggttttc gccctttgac gttggagtcc acgttcttta   13020
atagtggact cttgttccaa actggaacaa cactcaaccc tatctcggtc tattcttttg   13080
atttataagg gattttgccg atttcggcct attggttaaa aaatgagctg atttaacaaa   13140
aatttaacgc gaattttaac aaaatattaa caaaatatta acgtttacaa ttt          13193
```

<210> SEQ ID NO 66
<211> LENGTH: 13240
<212> TYPE: DNA
<213> ORGANISM: Artificial Sequence
<220> FEATURE:
<223> OTHER INFORMATION: pNShtxBE7120-SP-ptxD

<400> SEQUENCE: 66

```
cccattcgcc attcaggctg cgcaactgtt gggaagggcg atcggtgcgg gcctcttcgc     60
tattacgcca gctggcgaaa gggggatgtg ctgcaaggcg attaagttgg gtaacgccag    120
ggttttccca gtcacgacgt tgtaaaacga cggccagtgc caagctaaaa gcgctccgca    180
tggatctgac caacatgatc attgagttgc gcgtttccaa tgccttctcc aagggcggca    240
ttcccctgac tgttgaaggc gttgccaata tcaagattgc tggggaagaa ccgaccatcc    300
acaacgcgat cgagcggctg cttggcaaaa accgtaagga atcgagcaa attgccaagg    360
agaccctcga aggcaacttg cgtggtgttt tagccagcct cacgccggag cagatcaacg    420
aggacaaaat tgcctttgcc aaaagtctgc tggaagaggc ggaggatgac cttgagcagc    480
tgggtctagt cctcgatacg ctgcaagtcc agaacatttc cgatgaggtc ggttatctct    540
cggctagtgg acgcaagcag cgggctgatc tgcagcgaga tgcccgaatt gctgaagccg    600
atgcccaggc tgcctctgcg atccaaacgg ccgaaaatga caagatcacg gccctgcgtc    660
ggatcgatcg cgatgtagcg atcgcccaag ccgaggccga gcgccggatt caggatgcgt    720
tgacgcggcg cgaagcggtg gtggccgaag ctgaagcgga cattgctacc gaagtcgctc    780
gtagccaagc agaactccct gtgcagcagg agcggatcaa acaggtgcag cagcaacttc    840
aagccgatgt gatcgcccca gctgaggcag cttgtaaacg ggcgatcgcg gaagcgcggg    900
gggccgccgc ccgtatcgtc gaagatgaa aagctcaagc ggaagggacc caacggctgg    960
cggaggcttg gcagaccgct ggtgctaatg cccgcgacat cttcctgctc cagaagctcg   1020
```

```
actatgcttg taaaccgttt tgtgaaaaaa tttttaaaat aaaaaagggg acctctaggg    1080
tccccaatta attagtaata taatctatta aaggtcattc aaaaggtcat ccaccggatc    1140
agcttagtaa agccctcgct agattttaat gcggatgttg cgattacttc gccaactatt    1200
gcgataacaa gaaaaagcca gcctttcatg atatatctcc caatttgtgt agggcttatt    1260
atgcacgctt aaaaataata aaagcagact tgacctgata gtttggctgt gagcaattat    1320
gtgcttagtg catctaacgc ttgagttaag ccgcgccgcg aagcggcgtc ggcttgaacg    1380
aattgttaga cattatttgc cgactacctt ggtgatctcg cctttcacgt agtggacaaa    1440
ttcttccaac tgatctgcgc gcgaggccaa gcgatcttct tcttgtccaa gataagcctg    1500
tctagcttca agtatgacgg gctgatactg ggccggcagg cgctccattg cccagtcggc    1560
agcgacatcc ttcggcgcga ttttgccggt tactgcgctg taccaaatgc gggacaacgt    1620
aagcactaca tttcgctcat cgccagccca gtcgggcggc gagttccata gcgttaaggt    1680
ttcatttagc gcctcaaata gatcctgttc aggaaccgga tcaaagagtt cctccgccgc    1740
tggacctacc aaggcaacgc tatgttctct tgcttttgtc agcaagatag ccagatcaat    1800
gtcgatcgtg gctggctcga agatacctgc aagaatgtca ttgcgctgcc attctccaaa    1860
ttgcagttcg cgcttagctg gataacgcca cggaatgatg tcgtcgtgca caacaatggt    1920
gacttctaca gcgcggagaa tctcgctctc tccaggggaa gccgaagttt ccaaaaggtc    1980
gttgatcaaa gctcgccgcg ttgtttcatc aagccttacg gtcaccgtaa ccagcaaatc    2040
aatatcactg tgtggcttca ggccgccatc cactgcggag ccgtacaaat gtacggccag    2100
caacgtcggt tcgagatggc gctcgatgac gccaactacc tctgatagtt gagtcgatac    2160
ttcggcgatc accgcttccc tcatgatgtt aactttgtt ttagggcgac tgccctgctg    2220
cgtaacatcg ttgctgctcc ataacatcaa acatcgaccc acggcgtaac gcgcttgctg    2280
cttggatgcc cgaggcatag actgtacccc aaaaaaacag tcataacaag ccatgaaaac    2340
cgccactgcg ccgttaccac cgctgcgttc ggtcaaggtt ctggaccagt tgcgtgagcg    2400
catacgctac ttgcattaca gcttacgaac cgaacaggct tatgtccact gggttcgtgc    2460
cttcatccgt ttccacggtg tgcgtcaccc ggcaaccttg ggcagcagcg aagtcgaggc    2520
atttctgtcc tggctggcga acgagcgcaa ggtttcggtc tccacgcatc gtcaggcatt    2580
ggcggccttg ctgttcttct acggcaaggt gctgtgcacg gatctgccct ggcttcagga    2640
gatcggaaga cctcggccgt cgcggcgctt gccggtggtg ctgacccgg atgaagtggt    2700 tcgcatcctc ggttttctgg aaggcgagca tcgtttgttc gcccagcttc tgtatggaac    2760
gggcatgcgg atcagtgagg gtttgcaact gcgggtcaag gatctggatt tcgatcacgg    2820
cacgatcatc gtgcgggagg gcaagggctc caaggatcgg gccttgatgt acccgagag    2880 cttggcaccc agcctgcgcg agcagggaa ttgatccggt ggatgacctt tgaatgacc    2940 tttaatagat tatattacta attaattggg gaccctagag gtccccttt ttattttaaa    3000 aatttttcca caaaacggtt tacaagcata gtcgagttac gttgacacca tcgaatggtg    3060
caaaaccttt cgcggtatgg catgatagcg cccggaagag agtcaattca gggtggtgaa    3120
tgtgaaacca gtaacgttat acgatgtcgc agagtatgcc ggtgtctctt atcagaccgt    3180
ttcccgcgtg gtgaaccagg ccagccacgt ttctgcgaaa acgcgggaaa aagtggaagc    3240
ggcgatggcg gagctgaatt acattcccaa ccgcgtggca caacaactgg cgggcaaaca    3300
gtcgttgctg attggcgttg ccacctccag tctggccctg cacgcgccgt cgcaaattgt    3360
```

-continued

| | |
|---|---|
| cgcggcgatt aaatctcgcg ccgatcaact gggtgccagc gtggtggtgt cgatggtaga | 3420 |
| acgaagcggc gtcgaagcct gtaaagcggc ggtgcacaat cttctcgcgc aacgcgtcag | 3480 |
| tgggctgatc attaactatc cgctggatga ccaggatgcc attgctgtgg aagctgcctg | 3540 |
| cactaatgtt ccggcgttat ttcttgatgt ctctgaccag acacccatca acagtattat | 3600 |
| tttctcccat gaagacggta cgcgacgggc gtggagcatc tggtcgcatt gggtcaccag | 3660 |
| caaatcgcgc tgttagcggg cccattaagt tctgtctcgg cgcgtctgcg tctggctggc | 3720 |
| tggcataaat atctcactcg caatcaaatt cagccgatag cggaacggga aggcgactgg | 3780 |
| agtgccatgt ccggttttca acaaaccatg caaatgctga atgagggcat cgttcccact | 3840 |
| gcgatgctgg ttgccaacga tcagatggcg ctgggcgcaa tgcgcgccat taccgagtcc | 3900 |
| gggctgcgcg ttggtgcgga tatctcggta gtgggatacg acgataccga agacagctca | 3960 |
| tgttatatcc cgccgttaac caccatcaaa caggattttc gcctgctggg gcaaaccagc | 4020 |
| gtggaccgct tgctgcaact ctctcagggc caggcggtga agggcaatca gctgttgccc | 4080 |
| gtctcactgg tgaaaagaaa aaccaccctg gcgcccaata cgcaaaccgc ctctccccgc | 4140 |
| gcgttggccg attcattaat gcagctggca cgacaggttt cccgactgga aagcgggcag | 4200 |
| tgagcgcaac gcaattaatg tgagttagcg cgaattgatc tggtttgaca gcttatcatc | 4260 |
| gactgcacgg tgcaccaatg cttctggcgt caggcagcca tcggaagctg tggtatggct | 4320 |
| gtgcaggtcg taaatcactg cataattcgt gtcgctcaag gcgcactccc gttctggata | 4380 |
| atgtttttttg cgccgacatc ataacggttc tggcaaatat tctgaaatga gctgttgaca | 4440 |
| attaatcatc cggctcgtat aatgtgtgga attgtgagcg gataacaatt tcacacagga | 4500 |
| aacagaccat ggaattcatc ctaggagcat caccatggcg atcgcaatca aaaaaccctt | 4560 |
| actgacatct gtgctgtag ctgtgttggc actggttggc tgtcaagcac caataacac | 4620 |
| tactactaat ggttctactg ctcctaatgc aaagagcgca gctgctgagg ttgtcaatgg | 4680 |
| taaacttcac ctgcgttttg caattgcgcc gatgcgtcca acgcctagcc agaccatcaa | 4740 |
| agagtttgag ccgatattca gtatctcgc cgaccagctc ggcgcgacct atgaaatcgt | 4800 |
| ctccccggaa agctgggcgg caatatctgt ggcaatgaca aatggccatg tcgatgtggg | 4860 |
| ctggctcgga ccctggggct atgtcttgtc gaataaaaag gccggcaccg aagtgcttgc | 4920 |
| aacggtcaag taccgcgggg agccgttcta caaagccctc attgtcggtc gcgccgatct | 4980 |
| gccgatcaaa aaatggcccg aggacgcgaa gggtttgaag ctgtcactca gtgatcaggg | 5040 |
| caacacttct ggctggctca tcccgatggc gtacttcaag agcatcggca tcgaccctgc | 5100 |
| gagctatttt gaatatcgtg aaggtgccac gtttggccag aacgaatcac agattcagca | 5160 |
| cggactgatc gacctcggat ccgatatgga tcgggccgg aacgggatga tcgaagcggg | 5220 |
| tcaaatcgat ccttcgaagt ccaagatcgt gtgggaatcc agcaagctgc cgaacgacgc | 5280 |
| gatatccgtg ccgaaggatt ttgatcctgc tctgaaagcg cgcatcacgg aaatactgac | 5340 |
| gtccttgtcc gaagagaaag cacagtcgct gatgggctcg gctataacg gcttcgtgaa | 5400 |
| ggcaaagcac agcgattaca aggtaatcga agacgccggc cgcatcctgg aaaactgta | 5460 |
| aagcacgagg ggtccgttct tggatgaggg cagcggacga caaggtggac tgacgcacgc | 5520 |
| cagctccttg tctccgctgc acgaacatac gggcgcgcat cgcaatacca cagaggatga | 5580 |
| accaatgaat cagcgaatcg aagaagtcat gctggctaat gtcaagaggg acgtagccag | 5640 |
| gagaaagcgg cattttgcaa cgtcggtcgt agtactcagt ttgctggcag tggcctggta | 5700 |
| cgtgtgtcag atagaattcc agaagctagg cgccggttta ccgagactat ggtcattcgt | 5760 |

```
cgtgcagatg tttccacccg acctgagcga cctggacgtc attctaaaag gggctggcga    5820
gacgctcgcc atggcgacga ttggcacgat attcgccaca atcattgcat ttccgctggc    5880
actcatggct gcgcgtaata cctgtccgaa caagtggacc tatcgggtat cccgcgccat    5940
cctgaacgcc agccgcggca cggagacatt tgtctatgca cttgtatttg tagcagcagt    6000
gggcttcggt ccgttctccg gcgtactggc cattactttc cacatggtag gggcaatcgg    6060
caaaatgttt gctgaagcca tcgagcccgt tgaccaaggg ccgttggatg cgctcgcctt    6120
gaccggtgcc agcagggcaa agattatccg ctacggtctg atcccggatg ttatgccgca    6180
cctgatcgcg agcgttctat acatttggga attcagtgtc agaacgtcca cagtactggg    6240
catcgtaggc gcaggtggaa ttgggcagac cctgaaagat actgtggact tgttggaatt    6300
caacaagatg attacggtac tggcggttgt attgctgatg gtgtcggcaa tcgatttcat    6360
cagtgaccgg ctcaggtact tgatattgga cacaaaacgc gagggattcg aaactctccc    6420
tgcgaataac tgattgcttc acgtattact ggaagggagg ttcgcaatga agatgtagc    6480
gttgcagtta aagaatgtcg gtaagtcata cggcaataaa gttgtcctgg aatcgattga    6540
cttcgaagta cgtcacggct caatggttgc cttgctcggc acaagcgggg cagggaagtc    6600
gacgcttttc cgatgtctca ctggccttga gccgattgac tccggttcta tcgtggcgct    6660
cggagaatcc atacatgaac tgtctccggc gcgtctgcgg gcagtacgtg gccagatcgg    6720
gttcgtgttc caacaactgc acctggtgaa aaggttctca gcactcgaga atgtattggg    6780
tgcgcgtctg gcagagatgc ccatttggcg cgtcacattg aaaagcttca gccgggctga    6840
caaagtgctc gcgttcgaat gtctggaccg ggtcggcatg ctcgattatg caaacacgcc    6900
tacgcaactg ctgtcaggcg gtcagcaaca gcgtattgcg atagcgcgag ccttggcgca    6960
gaagcccaag attattattg cggacgaacc cgtctccagc ctcgatccgc tgacggcgcg    7020
ctcggttctg caaacgctga aagccgcggc tacagatctt aatgtcgcgg tcctgtgcag    7080
cctgcaccag gtagacctgg cccgtgagtt tggcgaccgc atcgtgggca tgcgcgacgg    7140
acgtgtcgtt ttcgacggca cgccagcgga attcaccgac gagcgcgtgc atgcgcttta    7200
ccagggtgcc cgctgggaag atgcaccagc ggccgagagc gacgcgcagc actcggtggc    7260
cggtctggct gtggcatgag gggcgaagcg atgaccacat ccacacgccc catcccgtg    7320
ccgccccagg gcaccgcact gcactggcac ctgagcgcgc cctacaacgc caaacatctg    7380
ctggtgctga tcgccgtcat ggtgctgttg ttcgtgaccg gacaacgcac cgaaatggac    7440
cgcatggtgg ccatgacggc acaggccgtg gccaagaccg tgggcctggc tgacgattca    7500
caagtcgcgc gcggcttgtc gcgcgtcggt caagccatgt ggccacccgc catcgcagaa    7560
accgaagagg tgggccggat tcaggacctg atcgccaga agctgcccct gttctcgcac    7620
atcgagaccc aggagcgcgt cgagcagaag atgaatctgg acacgctgaa gatggaagcc    7680
acgacggaaa ccgtcgaagt gctggtcaag ccggtcggct atgtctggac ggttttcatc    7740
aagatgatcg agaccctgga gattgcgctg tggggcacga tcctgtcggt gctggtgtcg    7800
attcccctgg cgtatttcgc ggcccgcaac tactagtcga cgccttcagc tccttcctgc    7860
gtcgcaagtt caaataactc ccaaagctta caaaggtttt tatgaagccc aaagtcgtcc    7920
tcacccactg ggtgcacccg gaaatcatcg aattgttgtc cgctagcgcc gatgttatcc    7980
ccaacaccac acgggaaacc ttgccgcgtt ctgaggtaat tgcgcgagcc aaagatgcgg    8040
atgcactcat ggctttcatg ccggacagca tcgacagcgc gtttctcgag gaatgtccaa    8100
```

```
agctgcgtgt catcggcgcc gcgcttaaag gctatgataa cttcgatgtc aacgcctgca    8160
cacgccacgg tgtatggctt acgattgtgc cggatttgct tacgatcccg accgctgaac    8220
tgactatcgg ccttcttctc ggtttgacaa ggcatatgct ggaaggcgat aggcaaatcc    8280
gtagcggaca cttccaaggc tggcggccga cactatatgg ctctggtttg acaggaaaaa    8340
cgcttggcat cattggtatg ggggcggtcg gccgtgcaat cgcccagcgc ttggctggct    8400
ttgaaatgaa tctcttgtat tgcgatccga ttccgctcaa tgccgaacaa gaaaaggctt    8460
ggcacgtaca gcgcgtcacg ctcgatgaac tgctcgaaaa atgtgattat gtcgtgccga    8520
tggttccgat ggccgcagag acactgcatc tgatcgatgc caccgcgttg gccaagatga    8580
aaaccggtag ctacctgatc aatgcatgtc gcggctcggt cgtggatgag aatgcggtga    8640
tagcagcact ggcgtctgga aaactagctg atatgcagc cgatgtcttc gagatggaag    8700
aatggatacg cgctgatcgc ccgcaggcta tccccaaggc gctgctcgac aatacggcac    8760
aaacgttttt tacgccgcat ttgggatcgg cggtcaagga agttcggctt gaaatcgagc    8820
ggcaggcagc gatgaacatc atccaggcac tcgctggtga aaaaccgatg ggcgcgatta    8880
atcagccgta tccgggagta aaggcggcgt gaaagcttgg ctgttttggc ggatgagaga    8940
agattttcag cctgatacag attaaatcag aacgcagaag cggtctgata aaacagaatt    9000
tgcctggcgg cagtagcgcg gtggtcccac ctgaccccat gccgaactca gaagtgaaac    9060
gccgtagcgc cgatggtagt gtggggtctc cccatgcgag agtagggaac tgccaggcat    9120
caaataaaac gaaaggctca gtcgaaagac tgggcctttc gttttatctg ttgtttgtcg    9180
gtgaacgctc tcctgagtag acaaatccg ccgggagcgg atttgaacgt tgcgaagcaa    9240
cggcccggag ggtggcgggc aggacgcccg ccataaactg ccaggcatca aattaagcag    9300
aaggccatcc tgacgatgg cctttttgcg tttctacaaa ctcttttgt ttattttct     9360 aaatacattc aaatatgtat ccgctcatga acaataacc ctgataaatg cttcaataat    9420
attgaaaaag gaagagtatg agtattcaac atttccgtgt cgcccttatt cccttttttg    9480
cggcattttg ccttcctgtt tttgctcacc cagaaacgct ggtgaaagta aagatgctg     9540 aagatcagtt gggtgcacga gtgggttaca tcgaactgga tctcaacagc ggtaagatcc    9600
ttgagagttt tcgccccgaa gaacgttttc caatgatgag cacttttaaa gttctgctat    9660
gtggcgcggt attatcccgt gttgacgccg ggcaagagca actcggtcgc cgcatacact    9720
attctcagaa tgacttggtt gagtatcgac gtggagtcga tcactgtgat tggcgaaggg    9780
gaaggcagcg ctacccaaat cgctagcttg ctggagaagc tgaaacaaac cacgggcatt    9840
gatctggcga atccctaccc ggtcaatcc gactcgcccg ctgcgaagtc ctaagagata    9900
gcgatgtgac cgcgatcgct tgtcaagaat cccagtgatc ccgaaccata ggaaggcaag    9960
ctcaatgctt gcctcgtctt gaggactatc tagatgtctg tggaacgcac atttattgcc    10020
atcaagcccg atggcgttca gcggggtttg gtcggtacga tcatcggccg ctttgagcaa    10080
aaaggcttca aactggtggg cctaaagcag ctgaagccca gtcgcgagct ggccgaacag    10140
cactatgctg tccaccgcga gcgccccttc ttcaatggcc tcgtcgagtt catcacctct    10200
gggccgatcg tggcgatcgt cttggaaggc gaaggcgttg tggcggctgc tcgcaagttg    10260
atcggcgcta ccaatccgct gacggcagaa ccgggcacca tccgtggtga ttttggtgtc    10320
aatattggcc gcaacatcat ccatggctcg gatgcaatcg aaacagcaca acaggaaatt    10380
gctctctggt ttagcccagc agagctaagt gattggaccc ccacgattca accctggctg    10440
tacgaataag gtctgcattc cttcagagag acattgccat gcccgtgctg cgatcgccct    10500
```

```
tccaagctgc cttgccccgc tgtttcgggc tggcagccct ggcgttgggg ctggcgaccg    10560
cttgccaaga aagcagcgct ccaattccct atagtgagtc gtattaaatt cgtaatcatg    10620
gtcatagctg tttcctgtgt gaaattgtta tccgctcaca attccacaca acatacgagc    10680
cggaagcata agtgtaaag cctggggtgc ctaatgagtg agctaactca cattaattgc     10740
gttgcgctca ctgcccgctt tccagtcggg aaacctgtcg tgccagctgc attaatgaat    10800
cggccaacgc gcggggagag gcggtttgcg tattgggcgc tcttccgctt cctcgctcac    10860
tgactcgctg cgctcggtcg ttcggctgcg gcgagcggta tcagctcact caaaggcggt    10920
aatacggtta tccacagaat cagggggataa cgcaggaaag aacatgtgag caaaaggcca    10980
gcaaaaggcc aggaaccgta aaaaggccgc gttgctggcg ttttttccata ggctccgccc   11040 ccctgacgag catcacaaaa atcgacgctc aagtcagagg tggcgaaacc cgacaggact    11100
ataaagatac caggcgtttc ccctggaag ctccctcgtg cgctctcctg ttccgaccct     11160
gccgcttacc ggatacctgt ccgcctttct cccttcggga agcgtggcgc tttctcatag    11220
ctcacgctgt aggtatctca gttcggtgta ggtcgttcgc tccaagctgg gctgtgtgca    11280
cgaacccccc gttcagcccg accgctgcgc cttatccggt aactatcgtc ttgagtccaa    11340
cccggtaaga cacgacttat cgccactggc agcagccact ggtaacagga ttagcagagc    11400
gaggtatgta ggcggtgcta cagagttctt gaagtggtgg cctaactacg gctacactag    11460
aaggacagta tttggtatct gcgctctgct gaagccagtt accttcggaa aaagagttgg    11520
tagctcttga tccggcaaac aaaccaccgc tggtagcggt ggtttttttg tttgcaagca    11580
gcagattacg cgcagaaaaa aaggatctca agaagatcct ttgatctttt ctacggggtc    11640
tgacgctcag tggaacgaaa actcacgtta agggattttg gtcatgagat tatcaaaaag    11700
gatcttcacc tagatccttt taaattaaaa atgaagtttt aaatcaatct aaagtatata    11760
tgagtaaact tggtctgaca gttaccaatg cttaatcagt gaggcaccta tctcagcgat    11820
ctgtctattt cgttcatcca tagttgcctg actccccgtc gtgtagataa ctacgatacg    11880
ggagggctta ccatctggcc ccagtgctgc aatgataccg cgagacccac gctcaccggc    11940
tccagattta tcagcaataa accagccagc cggaagggcc gagcgcagaa gtggtcctgc    12000
aactttatcc gcctccatcc agtctattaa ttgttgccgg gaagctagag taagtagttc    12060
gccagttaat agtttgcgca acgttgttgc cattgctaca ggcatcgtgg tgtcacgctc    12120
gtcgtttggt atggcttcat tcagctccgg ttcccaacga tcaaggcgag ttacatgatc    12180
ccccatgttg tgcaaaaaag cggttagctc cttcggtcct ccgatcgttg tcagaagtaa    12240
gttggccgca gtgttatcac tcatggttat ggcagcactg cataattctc ttactgtcat    12300
gccatccgta agatgctttt ctgtgactgg tgagtactca accaagtcat tctgagaata    12360
gtgtatgcgg cgaccgagtt gctcttgccc ggcgtcaata cgggataata ccgcgccaca    12420
tagcagaact ttaaaagtgc tcatcattgg aaaacgttct cggggcgaa aactctcaag     12480 gatcttaccg ctgttgagat ccagttcgat gtaacccact cgtgcaccca actgatcttc    12540
agcatctttt actttcacca gcgtttctgg gtgagcaaaa acaggaaggc aaaatgccgc    12600
aaaaaaggga ataagggcga cacggaaatg ttgaatactc atactcttcc tttttcaata    12660
ttattgaagc atttatcagg gttattgtct catgagcgga tacatatttg aatgtattta    12720
gaaaaataaa caaatagggg ttccgcgcac atttccccga aaagtgccac ctgacgcgcc    12780
ctgtagcggc gcattaagcg cggcgggtgt ggtggttacg cgcagcgtga ccgctacact    12840
```

```
tgccagcgcc ctagcgcccg ctcctttcgc tttcttccct tcctttctcg ccacgttcgc    12900 cggcttccc cgtcaagctc taaatcgggg catcccttta gggttccgat ttagtgcttt     12960
acggcacctc gaccccaaaa aacttgatta gggtgatggt tcacgtagtg ggccatcgcc    13020
ctgatagacg gttttcgcc ctttgacgtt ggagtccacg ttctttaata gtggactctt     13080
gttccaaact ggaacaacac tcaaccctat ctcggtctat tcttttgatt tataagggat    13140
tttgccgatt tcggcctatt ggttaaaaaa tgagctgatt taacaaaaat ttaacgcgaa    13200
ttttaacaaa atattaacaa aatattaacg tttacaattt                          13240
```

<210> SEQ ID NO 67
<211> LENGTH: 13183
<212> TYPE: DNA
<213> ORGANISM: Artificial Sequence
<220> FEATURE:
<223> OTHER INFORMATION: pNShtxBE4506-SP-ptxD

<400> SEQUENCE: 67

```
cccattcgcc attcaggctg cgcaactgtt gggaagggcg atcggtgcgg gcctcttcgc      60
tattacgcca gctggcgaaa gggggatgtg ctgcaaggcg attaagttgg gtaacgccag     120
ggttttccca gtcacgacgt tgtaaaacga cggccagtgc caagctaaaa gcgctccgca    180
tggatctgac caacatgatc attgagttgc gcgtttccaa tgccttctcc aagggcggca    240
ttcccctgac tgttgaaggc gttgccaata tcaagattgc tggggaagaa ccgaccatcc    300
acaacgcgat cgagcggctg cttggcaaaa accgtaagga aatcgagcaa attgccaagg    360
agaccctcga aggcaacttg cgtggtgttt tagccagcct cacgccggag cagatcaacg    420
aggacaaaat tgcctttgcc aaaagtctgc tggaagaggc ggaggatgac cttgagcagc    480
tgggtctagt cctcgatacg ctgcaagtcc agaacatttc cgatgaggtc ggttatctct    540
cggctagtgg acgcaagcag cgggctgatc tgcagcgaga tgcccgaatt gctgaagccg    600
atgcccaggc tgcctctgcg atccaaacgg ccgaaaatga caagatcacg gccctgcgtc    660
ggatcgatcg cgatgtagcg atcgcccaag ccgaggccga gcgccggatt caggatgcgt    720
tgacgcggcg cgaagcggtg gtggccgaag ctgaagcgga cattgctacc gaagtcgctc    780
gtagccaagc agaactccct gtgcagcagg agcggatcaa acaggtgcag cagcaacttc    840
aagccgatgt gatcgcccca gctgaggcag cttgtaaacg ggcgatcgcg gaagcgcggg    900
gggccgccgc ccgtatcgtc gaagatggaa agctcaagc ggaagggacc caacggctgg     960
cggaggcttg gcagaccgct ggtgctaatg cccgcgacat cttcctgctc cagaagctcg    1020
actatgcttg taaccgtttt tgtgaaaaaa tttttaaaat aaaaagggg acctctaggg     1080 tccccaatta attagtaata taatctatta aaggtcattc aaaaggtcat ccaccggatc    1140
agcttagtaa agccctcgct agattttaat gcggatgttg cgattacttc gccaactatt    1200
gcgataacaa gaaaaagcca gcctttcatg atatatctcc caatttgtgt agggcttatt    1260
atgcacgctt aaaaataata aaagcagact tgacctgata gtttggctgt gagcaattat    1320
gtgcttagtg catctaacgc ttgagttaag ccgcgccgcg aagcggcgtc ggcttgaacg    1380
aattgttaga cattatttgc cgactacctt ggtgatctcg cctttcacgt agtggacaaa    1440
ttcttccaac tgatctgcgc gcgaggccaa gcgatcttct tcttgtccaa gataagcctg    1500
tctagcttca agtatgacgg gctgatactg ggccggcagg cgctccattg cccagtcggc    1560
agcgacatcc ttcggcgcga ttttgccggt tactgcgctg taccaaatgc gggacaacgt    1620
aagcactaca tttcgctcat cgccagccca gtcgggcggc gagttccata gcgttaaggt    1680
```

```
ttcatttagc gcctcaaata gatcctgttc aggaaccgga tcaaagagtt cctccgccgc   1740
tggacctacc aaggcaacgc tatgttctct tgcttttgtc agcaagatag ccagatcaat   1800
gtcgatcgtg gctggctcga agatacctgc aagaatgtca ttgcgctgcc attctccaaa   1860
ttgcagttcg cgcttagctg gataacgcca cggaatgatg tcgtcgtgca caacaatggt   1920
gacttctaca gcgcggagaa tctcgctctc tccaggggaa gccgaagttt ccaaaaggtc   1980
gttgatcaaa gctcgccgcg ttgtttcatc aagccttacg gtcaccgtaa ccagcaaatc   2040
aatatcactg tgtggcttca ggccgccatc cactgcggag ccgtacaaat gtacggccag   2100
caacgtcggt tcgagatggc gctcgatgac gccaactacc tctgatagtt gagtcgatac   2160
ttcggcgatc accgcttccc tcatgatgtt aactttgtt ttagggcgac tgccctgctg   2220
cgtaacatcg ttgctgctcc ataacatcaa acatcgaccc acggcgtaac gcgcttgctg   2280
cttggatgcc cgaggcatag actgtacccc aaaaaaacag tcataacaag ccatgaaaac   2340
cgccactgcg ccgttaccac cgctgcgttc ggtcaaggtt ctggaccagt tgcgtgagcg   2400
catacgctac ttgcattaca gcttacgaac cgaacaggct tatgtccact gggttcgtgc   2460
cttcatccgt ttccacggtg tgcgtcaccc ggcaaccttg ggcagcagcg aagtcgaggc   2520
atttctgtcc tggctggcga acgagcgcaa ggtttcggtc tccacgcatc gtcaggcatt   2580
ggcggccttg ctgttcttct acggcaaggt gctgtgcacg gatctgccct ggcttcagga   2640
gatcggaaga cctcggccgt cgcggcgctt gccggtggtg ctgaccccgg atgaagtggt   2700
tcgcatcctc ggttttctgg aaggcgagca tcgtttgttc gcccagcttc tgtatggaac   2760
gggcatgcgg atcagtgagg gtttgcaact gcgggtcaag gatctggatt tcgatcacgg   2820
cacgatcatc gtgcgggagg gcaagggctc caaggatcgg gccttgatgt tacccgagag   2880
cttggcaccc agcctgcgcg agcaggggaa ttgatccggt ggatgacctt tgaatgacc   2940 tttaatagat tatattacta attaattggg gaccctagag gtccccttt ttatttaaa    3000 aattttttca caaacggtt tacaagcata gtcgagttac gttgacacca tcgaatggtg    3060
caaaaccttt cgcggtatgg catgatagcg cccggaagag agtcaattca gggtggtgaa    3120
tgtgaaacca gtaacgttat acgatgtcgc agagtatgcc ggtgtctctt atcagaccgt    3180 ttccgcgtg gtgaaccagg ccagccacgt ttctgcgaaa acgcgggaaa aagtggaagc     3240
ggcgatggcg gagctgaatt acattcccaa ccgcgtggca caacaactgg cgggcaaaca    3300
gtcgttgctg attggcgttg ccacctccag tctggccctg cacgcgccgt cgcaaattgt    3360
cgcggcgatt aaatctcgcg ccgatcaact gggtgccagc gtggtggtgt cgatggtaga    3420
acgaagcggc gtcgaagcct gtaaagcggc ggtgcacaat cttctcgcgc aacgcgtcag    3480
tgggctgatc attaactatc cgctggatga ccaggatgcc attgctgtgg aagctgcctg    3540
cactaatgtt ccggcgttat tcttgatgt ctctgaccag acacccatca acagtattat     3600
tttctcccat gaagacggta cgcgacgggc gtggagcatc tggtcgcatt gggtcaccag    3660
caaatcgcgc tgttagcggg cccattaagt tctgtctcgg cgcgtctgcg tctggctggc    3720
tggcataaat atctcactcg caatcaaatt cagccgatag cggaacggga aggcgactgg    3780
agtgccatgt ccgttttca acaaaccatg caaatgctga atgagggcat cgttcccact     3840
gcgatgctgg ttgccaacga tcagatggcg ctgggcgcaa tgcgcgccat taccgagtcc    3900
gggctgcgcg ttggtgcgga tatctcggta gtgggatacg acgataccga agacagctca    3960
tgttatatcc cgccgttaac caccatcaaa caggattttc gcctgctggg gcaaaccagc    4020
```

```
gtggaccgct tgctgcaact ctctcagggc caggcggtga agggcaatca gctgttgccc    4080
gtctcactgg tgaaaagaaa aaccaccctg gcgcccaata cgcaaaccgc ctctccccgc    4140
gcgttggccg attcattaat gcagctggca cgacaggttt cccgactgga aagcgggcag    4200
tgagcgcaac gcaattaatg tgagttagcg cgaattgatc tggtttgaca gcttatcatc    4260
gactgcacgg tgcaccaatg cttctggcgt caggcagcca tcggaagctg tggtatggct    4320
gtgcaggtcg taaatcactg cataattcgt gtcgctcaag gcgcactccc gttctggata    4380
atgttttttg cgccgacatc ataacggttc tggcaaatat tctgaaatga gctgttgaca    4440
attaatcatc cggctcgtat aatgtgtgga attgtgagcg gataacaatt tcacacagga    4500
aacagaccat ggaattcatc ctaggagcat caccatgaaa aaactcgcat ccgcattatt    4560
gtctgtcttg cttgccgccg tctgcagcat tggccatgca tcatccgctg aggttgtcaa    4620
tggtaaactt cacctgcgtt ttgcaattgc gccgatgcgt ccaacgccta gccagaccat    4680
caaagagttt gagccgatat tcaagtatct cgccgaccag ctcggcgcga cctatgaaat    4740
cgtctccccg gaaagctggg cggcaatatc tgtggcaatg acaaatggcc atgtcgatgt    4800
gggctggctc ggaccctggg gctatgtctt gtcgaataaa aaggccggca ccgaagtgct    4860
tgcaacggtc aagtaccgcg gggagccgtt ctacaaagcc ctcattgtcg gtcgcgccga    4920
tctgccgatc aaaaaatggc ccgaggacgc gaagggtttg aagctgtcac tcagtgatca    4980
gggcaacact tctggctggc tcatcccgat ggcgtacttc aagagcatcg gcatcgaccc    5040
tgcgagctat tttgaatatc gtgaaggtgc cacgtttggc cagaacgaat cacagattca    5100
gcacggactg atcgacctcg gatccgatat ggatcggggc cggaacggga tgatcgaagc    5160
gggtcaaatc gatccttcga agtccaagat cgtgtgggaa tccagcaagc tgccgaacga    5220
cgcgatatcc gtgccgaagg attttgatcc tgctctgaaa gcgcgcatca cggaaatact    5280
gacgtccttg tccgaagaga agcacagtc gctgatgggc tcgggctata cggcttcgt    5340 gaaggcaaag cacagcgatt acaaggtaat cgaagacgcc ggccgcatcc tgggaaaact    5400
gtaaagcacg aggggtccgt tcttggatga gggcagcgga cgacaaggtg gactgacgca    5460
cgccagctcc ttgtctccgc tgcacgaaca tacgggcgcg catcgcaata ccacagagga    5520
tgaaccaatg aatcagcgaa tcgaagaagt catgctggct aatgtcaaga gggacgtagc    5580
caggagaaag cggcattttg caacgtcggt cgtagtactc agtttgctgg cagtggcctg    5640
gtacgtgtgt cagatagaat ccagaagct aggcgccggt ttaccgagac tatggtcatt    5700
cgtcgtgcag atgttttccac ccgacctgag cgacctggac gtcattctaa aaggggctgg    5760
cgagacgctc gccatggcga cgattggcac gatattcgcc acaatcattg catttccgct    5820
ggcactcatg gctgcgcgta ataccctgtcc gaacaagtgg acctatcggg tatcccgcgc    5880
catcctgaac gccagccgcg gcacggagac atttgtctat gcacttgtat ttgtagcagc    5940
agtgggcttc ggtccgttct ccggcgtact ggccattact ttccacatgg taggggcaat    6000
cggcaaaatg tttgctgaag ccatcgagcc cgttgaccaa gggccgttgg atgcgctcgc    6060
cttgaccggt gccagcaggg caaagattat ccgctacggt ctgatcccgg atgttatgcc    6120
gcacctgatc gcgagcgttc tatacatttg ggaattcagt gtcagaacgt ccacagtact    6180
gggcatcgta ggcgcaggtg gaattgggca gaccctgaaa gatactgtgg acttgttgga    6240
attcaacaag atgattacgg tactggcggt tgtattgctg atggtgtcgg caatcgattt    6300
catcagtgac cggctcaggt acttgatatt ggacacaaaa cgcgagggat tcgaaactct    6360
ccctgcgaat aactgattgc ttcacgtatt actggaaggg aggttcgcaa tgaaagatgt    6420
```

| | |
|---|---|
| agcgttgcag ttaaagaatg tcggtaagtc atacggcaat aaagttgtcc tggaatcgat | 6480 |
| tgacttcgaa gtacgtcacg gctcaatggt tgccttgctc ggcacaagcg ggcagggaa | 6540 |
| gtcgacgctt ttccgatgtc tcactggcct tgagccgatt gactccggtt ctatcgtggc | 6600 |
| gctcggagaa tccatacatg aactgtctcc ggcgcgtctg cgggcagtac gtggccagat | 6660 |
| cgggttcgtg ttccaacaac tgcacctggt gaaaaggttc tcagcactcg agaatgtatt | 6720 |
| gggtgcgcgt ctggcagaga tgcccatttg gcgcgtcaca ttgaaaagct tcagccgggc | 6780 |
| tgacaaagtg ctcgcgttcg aatgtctgga ccgggtcggc atgctcgatt atgcaaacac | 6840 |
| gcctacgcaa ctgctgtcag gcggtcagca acagcgtatt gcgatagcgc gagccttggc | 6900 |
| gcagaagccc aagattatta ttgcggacga acccgtctcc agcctcgatc cgctgacggc | 6960 |
| gcgctcggtt ctgcaaacgc tgaaagccgc ggctacagat cttaatgtcg cggtcctgtg | 7020 |
| cagcctgcac caggtagacc tggcccgtga gtttggcgac cgcatcgtgg gcatgcgcga | 7080 |
| cggacgtgtc gttttcgacg gcacgccagc ggaattcacc gacgagcgcg tgcatgcgct | 7140 |
| ttaccagggt gcccgctggg aagatgcacc agcggccgag agcgacgcgc agcactcggt | 7200 |
| ggccggtctg gctgtggcat gaggggcgaa gcgatgacca catccacacg ccccataccc | 7260 |
| gtgccgcccc agggcaccgc actgcactgg cacctgagcg cgccctacaa cgccaaacat | 7320 |
| ctgctggtgc tgatcgccgt catggtgctg ttgttcgtga ccggcaacg caccgaaatg | 7380 |
| gaccgcatgg tggccatgac ggcacaggcc gtggccaaga ccgtgggcct ggctgacgat | 7440 |
| tcacaagtcg cgcgcggctt gtcgcgcgtc ggtcaagcca tgtggccacc cgccatcgca | 7500 |
| gaaaccgaag aggtgggccg gattcaggac ctggatcgcc agaagctgcc cctgttctcg | 7560 |
| cacatcgaga cccaggagcg cgtcgagcag aagatgaatc tggacacgct gaagatggaa | 7620 |
| gccacgacgg aaaccgtcga agtgctggtc aagccggtcg gctatgtctg gacggttttc | 7680 |
| atcaagatga tcgagaccct ggagattgcg ctgtggggca cgatcctgtc ggtgctggtg | 7740 |
| tcgattcccc tggcgtattt cgcggcccgc aactactagt cgacgccttc agctccttcc | 7800 |
| tgcgtcgcaa gttcaaataa ctcccaaagc ttacaaaggt ttttatgaag cccaaagtcg | 7860 |
| tcctcaccca ctgggtgcac ccggaaatca tcgaattgtt gtccgctagc gccgatgtta | 7920 |
| tccccaacac cacacgggaa accttgccgc gttctgaggt aattgcgcga gccaaagatg | 7980 |
| cggatgcact catggctttc atgccggaca gcatcgacag cgcgtttctc gaggaatgtc | 8040 |
| caaagctgcg tgtcatcggc gccgcgctta aaggctatga taacttcgat gtcaacgcct | 8100 |
| gcacacgcca cggtgtatgg cttacgattg tgccggattt gcttacgatc ccgaccgctg | 8160 |
| aactgactat cggccttctt ctcggtttga caaggcatat gctggaaggc gataggcaaa | 8220 |
| tccgtagcgg acacttccaa ggctggcggc cgacactata tggctctggt ttgacaggaa | 8280 |
| aaacgcttgg catcattggt atgggggcgg tcggccgtgc aatcgcccag cgcttggctg | 8340 |
| gctttgaaat gaatctcttg tattgcgatc cgattccgct caatgccgaa caagaaaagg | 8400 |
| cttggcacgt acagcgcgtc acgctcgatg aactgctcga aaaatgtgat tatgtcgtgc | 8460 |
| cgatggttcc gatggccgca gagacactgc atctgatcga tgccaccgcg ttggccaaga | 8520 |
| tgaaaaccgg tagctacctg atcaatgcat gtcgcggctc ggtcgtggat gagaatgcgc | 8580 |
| tgatagcagc actggcgtct ggaaaactag ctggatatgc agccgatgtc ttcgagatgg | 8640 |
| aagaatggat acgcgctgat cgcccgcagg ctatccccaa ggcgctgctc gacaatacgg | 8700 |
| cacaaacgtt ttttacgccg catttgggat cggcggtcaa ggaagttcgg cttgaaatcg | 8760 |

```
agcggcaggc agcgatgaac atcatccagg cactcgctgg tgaaaaaccg atgggcgcga    8820
ttaatcagcc gtatccggga gtaaaggcgg cgtgaaagct tggctgtttt ggcggatgag    8880
agaagatttt cagcctgata cagattaaat cagaacgcag aagcggtctg ataaaacaga    8940
atttgcctgg cggcagtagc gcggtggtcc cacctgaccc catgccgaac tcagaagtga    9000
aacgccgtag cgccgatggt agtgtggggt ctccccatgc gagagtaggg aactgccagg    9060
catcaaataa aacgaaaggc tcagtcgaaa gactgggcct ttcgttttat ctgttgtttg    9120
tcggtgaacg ctctcctgag taggacaaat ccgccgggag cggatttgaa cgttgcgaag    9180
caacggcccg gagggtggcg ggcaggacgc ccgccataaa ctgccaggca tcaaattaag    9240
cagaaggcca tcctgacgga tggcctttt gcgtttctac aaactctttt tgtttatttt      9300
tctaaataca ttcaaatatg tatccgctca tgagacaata accctgataa atgcttcaat    9360
aatattgaaa aaggaagagt atgagtattc aacatttccg tgtcgccctt attcccttt     9420 ttgcggcatt ttgccttcct gttttgctc acccagaaac gctggtgaaa gtaaaagatg      9480
ctgaagatca gttgggtgca cgagtgggtt acatcgaact ggatctcaac agcggtaaga    9540
tccttgagag ttttcgcccc gaagaacgtt ttccaatgat gagcactttt aaagttctgc    9600
tatgtggcgc ggtattatcc cgtgttgacg ccgggcaaga gcaactcggt cgccgcatac    9660
actattctca gaatgacttg gttgagtatc gacgtggagt cgatcactgt gattggcgaa    9720
ggggaaggca gcgctaccca aatcgctagc ttgctggaga agctgaaaca aaccacgggc    9780
attgatctgg cgaaatccct accgggtcaa tccgactcgc cgctgcgaa gtcctaagag     9840 atagcgatgt gaccgcgatc gcttgtcaag aatcccagtg atcccgaacc ataggaaggc    9900
aagctcaatg cttgcctcgt cttgaggact atctagatgt ctgtggaacg cacatttatt    9960
gccatcaagc ccgatggcgt tcagcgtggt ttggtcggta cgatcatcgg ccgctttgag   10020
caaaaaggct tcaaactggt gggcctaaag cagctgaagc ccagtcgcga gctggccgaa   10080
cagcactatg ctgtccaccg cgagcgcccc ttcttcaatg gcctcgtcga gttcatcacc   10140
tctgggccga tcgtggcgat cgtcttggaa ggcgaaggcg ttgtggcggc tgctcgcaag   10200
ttgatcggcg ctaccaatcc gctgacggca gaacccgggca ccatccgtgg tgattttggt   10260
gtcaatattg gccgcaacat catccatggc tcggatgcaa tcgaaacagc acaacaggaa   10320
attgctctct ggtttagccc agcagagcta agtgattgga cccccacgat caaccctgg    10380 ctgtacgaat aaggtctgca ttccttcaga gagacattgc catgcccgtg ctgcgatcgc   10440
ccttccaagc tgccttgccc cgctgtttcg ggctggcagc cctggcgttg gggctggcga   10500
ccgcttgcca agaaagcagc gctccaattc cctatagtga gtcgtattaa attcgtaatc   10560
atggtcatag ctgtttcctg tgtgaaattg ttatccgctc acaattccac acaacatacg   10620
agccggaagc ataaagtgta aagcctgggg tgcctaatga gtgagctaac tcacattaat   10680
tgcgttgcgc tcactgcccg ctttccagtc gggaaacctg tcgtgccagc tgcattaatg   10740
aatcggccaa cgcgcgggga gaggcggttt gcgtattggg cgctcttccg cttcctcgct   10800
cactgactcg ctgcgctcgg tcgttcggct gcggcgagcg gtatcagctc actcaaaggc   10860
ggtaatacgg ttatccacag aatcagggga taacgcagga aagaacatgt gagcaaaagg   10920
ccagcaaaag gccaggaacc gtaaaaaggc cgcgttgctg gcgtttttcc ataggctccg   10980
cccccctgac gagcatcaca aaaatcgacg ctcaagtcag aggtggcgaa acccgacagg   11040
actataaaga taccaggcgt ttccccctgg aagctccctc gtgcgctctc ctgttccgac   11100
cctgccgctt accggatacc tgtccgcctt tctcccttcg ggaagcgtgg cgctttctca   11160
```

```
tagctcacgc tgtaggtatc tcagttcggt gtaggtcgtt cgctccaagc tgggctgtgt   11220
gcacgaaccc cccgttcagc ccgaccgctg cgccttatcc ggtaactatc gtcttgagtc   11280
caacccggta agacacgact tatcgccact ggcagcagcc actggtaaca ggattagcag   11340
agcgaggtat gtaggcggtg ctacagagtt cttgaagtgg tggcctaact acggctacac   11400
tagaaggaca gtatttggta tctgcgctct gctgaagcca gttaccttcg gaaaaagagt   11460
tggtagctct tgatccggca aacaaaccac cgctggtagc ggtggttttt ttgtttgcaa   11520
gcagcagatt acgcgcagaa aaaaggatc tcaagaagat cctttgatct tttctacggg   11580
gtctgacgct cagtggaacg aaaactcacg ttaagggatt ttggtcatga gattatcaaa   11640
aaggatcttc acctagatcc ttttaaatta aaaatgaagt tttaaatcaa tctaaagtat   11700
atatgagtaa acttggtctg acagttacca atgcttaatc agtgaggcac ctatctcagc   11760
gatctgtcta tttcgttcat ccatagttgc ctgactcccc gtcgtgtaga taactacgat   11820
acgggagggc ttaccatctg gccccagtgc tgcaatgata ccgcgagacc cacgctcacc   11880
ggctccagat ttatcagcaa taaaccagcc agccggaagg gccgagcgca gaagtggtcc   11940
tgcaacttta tccgcctcca tccagtctat taattgttgc cgggaagcta gagtaagtag   12000
ttcgccagtt aatagtttgc gcaacgttgt tgccattgct acaggcatcg tggtgtcacg   12060
ctcgtcgttt ggtatggctt cattcagctc cggttcccaa cgatcaaggc gagttacatg   12120
atcccccatg ttgtgcaaaa aagcggttag ctccttcggt cctccgatcg ttgtcagaag   12180
taagttggcc gcagtgttat cactcatggt tatggcagca ctgcataatt ctcttactgt   12240
catgccatcc gtaagatgct tttctgtgac tggtgagtac tcaaccaagt cattctgaga   12300
atagtgtatg cggcgaccga gttgctcttg cccggcgtca atacgggata ataccgcgcc   12360
acatagcaga actttaaaag tgctcatcat tggaaaacgt tcttcggggc gaaaactctc   12420
aaggatctta ccgctgttga gatccagttc gatgtaaccc actcgtgcac ccaactgatc   12480
ttcagcatct tttactttca ccagcgtttc tgggtgagca aaaacaggaa ggcaaaatgc   12540
cgcaaaaaag ggaataaggg cgacacggaa atgttgaata ctcatactct tcctttttca   12600
atattattga agcatttatc agggttattg tctcatgagc ggatacatat ttgaatgtat   12660
ttagaaaaat aaacaaatag gggttccgcg cacatttccc cgaaaagtgc cacctgacgc   12720
gccctgtagc ggcgcattaa gcgcggcggg tgtggtggtt acgcgcagcg tgaccgctac   12780
acttgccagc gccctagcgc ccgctccttt cgctttcttc ccttcctttc tcgccacgtt   12840
cgccggcttt ccccgtcaag ctctaaatcg gggcatccct ttagggttcc gatttagtgc   12900
tttacggcac ctcgacccca aaaaacttga ttagggtgat ggttcacgta gtgggccatc   12960
gccctgatag acggttttc gccctttgac gttggagtcc acgttcttta atagtggact   13020
cttgttccaa actggaacaa cactcaaccc tatctcggtc tattcttttg atttataagg   13080
gattttgccg atttcggcct attggttaaa aaatgagctg atttaacaaa atttaacgc    13140 gaattttaac aaaatattaa caaatatta acgtttacaa ttt                     13183
```

<210> SEQ ID NO 68
<211> LENGTH: 13186
<212> TYPE: DNA
<213> ORGANISM: Artificial Sequence
<220> FEATURE:
<223> OTHER INFORMATION: pNShtxBE7942-SP-ptxD

<400> SEQUENCE: 68

```
cccattcgcc attcaggctg cgcaactgtt gggaagggcg atcggtgcgg gcctcttcgc      60
tattacgcca gctggcgaaa gggggatgtg ctgcaaggcg attaagttgg gtaacgccag     120
ggttttccca gtcacgacgt tgtaaaacga cggccagtgc caagctaaaa gcgctccgca     180
tggatctgac caacatgatc attgagttgc gcgtttccaa tgccttctcc aagggcggca     240
ttcccctgac tgttgaaggc gttgccaata tcaagattgc tggggaagaa ccgaccatcc     300
acaacgcgat cgagcggctg cttggcaaaa accgtaagga aatcgagcaa attgccaagg     360
agaccctcga aggcaacttg cgtggtgttt tagccagcct cacgccggag cagatcaacg     420
aggacaaaat tgcctttgcc aaaagtctgc tggaagaggc ggaggatgac cttgagcagc     480
tgggtctagt cctcgatacg ctgcaagtcc agaacatttc cgatgaggtc ggttatctct     540
cggctagtgg acgcaagcag cgggctgatc tgcagcgaga tgcccgaatt gctgaagccg     600
atgcccaggc tgcctctgcg atccaaacgg ccgaaaatga caagatcacg gccctgcgtc     660
ggatcgatcg cgatgtagcg atcgcccaag ccgaggccga gcgccggatt caggatgcgt     720
tgacgcggcg cgaagcggtg gtggccgaag ctgaagcgga cattgctacc gaagtcgctc     780
gtagccaagc agaactccct gtgcagcagg agcggatcaa acaggtgcag cagcaacttc     840
aagccgatgt gatcgcccca gctgaggcag cttgtaaacg ggcgatcgcg gaagcgcggg     900
gggccgccgc ccgtatcgtc gaagatggaa aagctcaagc ggaagggacc caacggctgg     960
cggaggcttg gcagaccgct ggtgctaatg cccgcgacat cttcctgctc cagaagctcg    1020
actatgcttg taaaccgttt tgtgaaaaaa tttttaaaat aaaaaagggg acctctaggg    1080
tccccaatta attagtaata taatctatta aaggtcattc aaaaggtcat ccaccggatc    1140
agcttagtaa agccctcgct agattttaat gcggatgttg cgattacttc gccaactatt    1200
gcgataacaa gaaaaagcca gcctttcatg atatatctcc caatttgtgt agggcttatt    1260
atgcacgctt aaaaataata aaagcagact tgacctgata gtttggctgt gagcaattat    1320
gtgcttagtg catctaacgc ttgagttaag ccgcgccgcg aagcggcgtc ggcttgaacg    1380
aattgttaga cattatttgc cgactacctt ggtgatctcg cctttcacgt agtggacaaa    1440
ttcttccaac tgatctgcgc gcgaggccaa gcgatcttct tcttgtccaa gataagcctg    1500
tctagcttca agtatgacgg gctgatactg gccggcagg cgctccattg cccagtcggc    1560
agcgacatcc ttcggcgcga ttttgccggt tactgcgctg taccaaatgc gggacaacgt    1620
aagcactaca tttcgctcat cgccagccca gtcgggcggc gagttccata gcgttaaggt    1680
ttcatttagc gcctcaaata gatcctgttc aggaaccgga tcaaagagtt cctccgccgc    1740
tggacctacc aaggcaacgc tatgttctct tgcttttgtc agcaagatag ccagatcaat    1800
gtcgatcgtg gctggctcga agatacctgc aagaatgtca ttgcgctgcc attctccaaa    1860
ttgcagttcg cgcttagctg gataacgcca cggaatgatg tcgtcgtgca caacaatggt    1920
gacttctaca gcgcggagaa tctcgctctc tccaggggaa gccgaagttt ccaaaaggtc    1980
gttgatcaaa gctcgccgcg ttgtttcatc aagccttacg gtcaccgtaa ccagcaaatc    2040
aatatcactg tgtggcttca ggccgccatc cactgcggag ccgtacaaat gtacggccag    2100
caacgtcggt tcgagatggc gctcgatgac gccaactacc tctgatagtt gagtcgatac    2160
ttcggcgatc accgcttccc tcatgatgtt taactttgtt ttagggcgac tgccctgctg    2220
cgtaacatcg ttgctgctcc ataacatcaa acatcgaccc acggcgtaac gcgcttgctg    2280
cttggatgcc cgaggcatag actgtacccc aaaaaaacag tcataacaag ccatgaaaac    2340
cgccactgcg ccgttaccac cgctgcgttc ggtcaaggtt ctggaccagt tgcgtgagcg    2400
```

```
catacgctac ttgcattaca gcttacgaac cgaacaggct tatgtccact gggttcgtgc    2460
cttcatccgt ttccacggtg tgcgtcaccc ggcaaccttg ggcagcagcg aagtcgaggc    2520
atttctgtcc tggctggcga acgagcgcaa ggtttcggtc tccacgcatc gtcaggcatt    2580
ggcggccttg ctgttcttct acggcaaggt gctgtgcacg gatctgccct ggcttcagga    2640
gatcggaaga cctcggccgt cgcggcgctt gccggtggtg ctgacccgg atgaagtggt     2700 tcgcatcctc ggttttctgg aaggcgagca tcgtttgttc gcccagcttc tgtatggaac    2760
gggcatgcgg atcagtgagg gtttgcaact gcgggtcaag gatctggatt cgatcacgg     2820 cacgatcatc gtgcgggagg gcaagggctc caaggatcgg gccttgatgt tacccgagag    2880
cttggcaccc agcctgcgcg agcaggggaa ttgatccggt ggatgacctt ttgaatgacc    2940
tttaatagat tatattacta attaattggg gaccctagag gtccccttt ttatttaaa      3000 aattttttca caaaacggtt tacaagcata gtcgagttac gttgacacca tcgaatggtg    3060
caaaaccttt cgcggtatgg catgatacgc cccggaagag agtcaattca gggtggtgaa    3120
tgtgaaacca gtaacgttat acgatgtcgc agagtatgcc ggtgtctctt atcagaccgt    3180
ttcccgcgtg gtgaaccagg ccagccacgt ttctgcgaaa acgcgggaaa agtggaagc     3240 ggcgatggcg gagctgaatt acattcccaa ccgcgtggca caacaactgg cgggcaaaca    3300
gtcgttgctg attggcgttg ccacctccag tctggccctg cacgcgccgt cgcaaattgt    3360
cgcggcgatt aaatctcgcg ccgatcaact gggtgccagc gtggtggtgt cgatggtaga    3420
acgaagcggc gtcgaagcct gtaaagcggc ggtgcacaat cttctcgcgc aacgcgtcag    3480
tgggctgatc attaactatc cgctggatga ccaggatgcc attgctgtgg aagctgcctg    3540
cactaatgtt ccggcgttat ttcttgatgt ctctgaccag acacccatca acagtattat    3600
tttctcccat gaagacggta cgcgacgggc gtggagcatc tggtcgcatt gggtcaccag    3660
caaatcgcgc tgttagcggg cccattaagt tctgtctcgg cgcgtctgcg tctggctggc    3720
tggcataaat atctcactcg caatcaaatt cagccgatag cggaacggga aggcgactgg    3780
agtgccatgt ccggttttca acaaaccatg caaatgctga atgagggcat cgttcccact    3840
gcgatgctgg ttgccaacga tcagatggcg ctgggcgcaa tgcgcgccat taccgagtcc    3900
gggctgcgcg ttggtgcgga tatctcggta gtgggatacg acgataccga agacagctca    3960
tgttatatcc cgccgttaac caccatcaaa caggattttc gcctgctggg gcaaaccagc    4020
gtggaccgct tgctgcaact ctctcagggc caggcggtga agggcaatca gctgttgccc    4080
gtctcactgg tgaaaagaaa aaccaccctg gcgcccaata cgcaaaccgc ctctccccgc    4140
gcgttggccg attcattaat gcagctggca cgacaggttt cccgactgga aagcgggcag    4200
tgagcgcaac gcaattaatg tgagttagcg cgaattgatc tggtttgaca gcttatcatc    4260
gactgcacgg tgcaccaatg cttctggcgt caggcagcca tcggaagctg tggtatggct    4320
gtgcaggtcg taaatcactg cataattcgt gtcgctcaag gcgcactccc gttctggata    4380 atgtttttg cgccgacatc ataacggttc tggcaaatat tctgaaatga gctgttgaca     4440
attaatcatc cggctcgtat aatgtgtgga attgtgagcg gataacaatt tcacacagga    4500
aacagaccat ggaattcatc ctaggagcat caccatggct tccctaaaat tccgactgct    4560
tggccttgca acgctggcag tcttggcaac taccgcttgc agctctggtg ctgaggttgt    4620
caatggtaaa cttcacctgc gttttgcaat tgcgccgatg cgtccaacgc ctagccagac    4680
catcaaagag tttgagccga tattcaagta tctcgccgac cagctcggcg cgacctatga    4740
```

```
aatcgtctcc ccggaaagct gggcggcaat atctgtggca atgacaaatg ccatgtcga   4800
tgtgggctgg ctcggaccct ggggctatgt cttgtcgaat aaaaaggccg gcaccgaagt  4860
gcttgcaacg gtcaagtacc gcggggagcc gttctacaaa gccctcattg tcggtcgcgc  4920
cgatctgccg atcaaaaaat ggcccgagga cgcgaagggt ttgaagctgt cactcagtga  4980
tcagggcaac acttctggct ggctcatccc gatggcgtac ttcaagagca tcggcatcga  5040
ccctgcgagc tattttgaat atcgtgaagg tgccacgttt ggccagaacg aatcacagat  5100
tcagcacgga ctgatcgacc tcggatccga tatggatcgg ggccggaacg ggatgatcga  5160
agcgggtcaa atcgatcctt cgaagtccaa gatcgtgtgg gaatccagca agctgccgaa  5220
cgacgcgata tccgtgccga aggattttga tcctgctctg aaagcgcgca tcacggaaat  5280
actgacgtcc ttgtccgaag agaaagcaca gtcgctgatg ggctcgggct ataacggctt  5340
cgtgaaggca aagcacagcg attacaaggt aatcgaagac gccggccgca tcctgggaaa  5400
actgtaaagc acgaggggtc cgttcttgga tgagggcagc ggacgacaag gtggactgac  5460
gcacgccagc tccttgtctc cgctgcacga acatacgggc gcgcatcgca ataccacaga  5520
ggatgaacca atgaatcagc gaatcgaaga agtcatgctg gctaatgtca agagggacgt  5580
agccaggaga aagcggcatt ttgcaacgtc ggtcgtagta ctcagtttgc tggcagtggc  5640
ctggtacgtg tgtcagatag aattccagaa gctaggcgcc ggtttaccga gactatggtc  5700
attcgtcgtg cagatgtttc cacccgacct gagcgacctg gacgtcattc taaaagggc   5760
tggcgagacg ctcgccatgg cgacgattgg cacgatattc gccacaatca ttgcatttcc  5820
gctggcactc atggctgcgc gtaatacctg tccgaacaag tggacctatc gggtatcccg  5880
cgccatcctg aacgccagcc gcggcacgga cactttgtc tatgcacttg tatttgtagc   5940
agcagtgggc ttcggtccgt ctccggcgt actggccatt actttccaca tggtaggggc   6000
aatcggcaaa atgtttgctg aagccatcga gcccgttgac caagggccgt tggatgcgct  6060
cgccttgacc ggtgccagca gggcaaagat tatccgctac ggtctgatcc cggatgttat  6120
gccgcacctg atcgcgagcg ttctatacat ttgggaattc agtgtcagaa cgtccacagt  6180
actgggcatc gtaggcgcag gtggaattgg gcagaccctg aaagatactg tggacttgtt  6240
ggaattcaac aagatgatta cggtactggc ggttgtattg ctgatggtgt cggcaatcga  6300
tttcatcagt gaccggctca ggtacttgat attggacaca aaacgcgagg gattcgaaac  6360
tctccctgcg aataactgat tgcttcacgt attactggaa gggaggttcg caatgaaaga  6420
tgtagcgttg cagttaaaga atgtcggtaa gtcatacggc aataaagttg tcctggaatc  6480
gattgacttc gaagtacgtc acggctcaat ggttgccttg ctcggcacaa gcggggcagg  6540
gaagtcgacg cttttccgat gtctcactgg ccttgagccg attgactccg gttctatcgt  6600
ggcgctcgga gaatccatac atgaactgtc tccggcgcgt ctgcgggcag tacgtggcca  6660
gatcgggttc gtgttccaac aactgcacct ggtgaaaagg ttctcagcac tcgagaatgt  6720
attgggtgcg cgtctggcag agatgccat ttggcgcgtc acattgaaaa gcttcagccg   6780
ggctgacaaa gtgctcgcgt tcgaatgtct ggaccgggtc ggcatgctcg attatgcaaa  6840
cacgcctacg caactgctgt caggcggtca gcaacagcgt attgcgatag cgcgagcctt  6900
ggcgcagaag cccaagatta ttattgcgga cgaacccgtc tccagcctcg atccgctgac  6960
ggcgcgctcg gttctgcaaa cgctgaaagc cgcggctaca gatcttaatg tcgcggtcct  7020
gtgcagcctg caccaggtag acctggcccg tgagtttggc gaccgcatcg tgggcatgcg  7080
cgacggacgt gtcgttttcg acggcacgcc agcggaattc accgacgagc gcgtgcatgc  7140
```

```
gctttaccag ggtgcccgct gggaagatgc accagcggcc gagagcgacg cgcagcactc   7200
ggtggccggt ctggctgtgg catgaggggc gaagcgatga ccacatccac acgcccata    7260 cccgtgccgc cccagggcac cgcactgcac tggcacctga gcgcgcccta caacgccaaa   7320
catctgctgg tgctgatcgc cgtcatggtg ctgttgttcg tgaccggaca acgcaccgaa   7380
atggaccgca tggtggccat gacggcacag gccgtggcca agaccgtggg cctggctgac   7440
gattcacaag tcgcgcgcgg cttgtcgcgc gtcggtcaag ccatgtggcc acccgccatc   7500
gcagaaaccg aagaggtggg ccggattcag gacctggatc gccagaagct gccccctgttc  7560 tcgcacatcg agacccagga gcgcgtcgag cagaagatga atctggacac gctgaagatg   7620
gaagccacga cggaaaccgt cgaagtgctg gtcaagccgg tcggctatgt ctggacggtt   7680
ttcatcaaga tgatcgagac cctggagatt gcgctgtggg cacgatcct gtcggtgctg    7740 gtgtcgattc ccctggcgta tttcgcggcc cgcaactact agtcgacgcc ttcagctcct   7800
tcctgcgtcg caagttcaaa taactcccaa agcttacaaa ggttttatg aagcccaaag    7860 tcgtcctcac ccactgggtg cacccggaaa tcatcgaatt gttgtccgct agcgccgatg   7920
ttatccccaa caccacacgg gaaaccttgc cgcgttctga ggtaattgcg cgagccaaag   7980
atgcggatgc actcatggct ttcatgccgg acagcatcga cagcgcgttt ctcgaggaat   8040
gtccaaagct gcgtgtcatc ggcgccgcgc ttaaaggcta tgataacttc gatgtcaacg   8100
cctgcacacg ccacggtgta tggcttacga ttgtgccgga tttgcttacg atcccgaccg   8160
ctgaactgac tatcggcctt cttctcggtt tgacaaggca tatgctggaa ggcgataggc   8220
aaatccgtag cggacacttc caaggctggc ggccgacact atatggctct ggtttgacag   8280
gaaaaacgct tggcatcatt ggtatggggg cggtcggccg tgcaatcgcc cagcgcttgg   8340
ctggctttga aatgaatctc ttgtattgcg atccgattcc gctcaatgcc gaacaagaaa   8400
aggcttggca cgtacagcgc gtcacgctcg atgaactgct cgaaaaatgt gattatgtcg   8460
tgccgatggt tccgatggcc gcagagacac tgcatctgat cgatgccacc gcgttggcca   8520
agatgaaaac cggtagctac ctgatcaatg catgtcgcgg ctcggtcgtg gatgagaatg   8580
cggtgatagc agcactggcg tctggaaaac tagctggata tgcagccgat gtcttcgaga   8640
tggaagaatg gatacgcgct gatcgcccgc aggctatccc caaggcgctg ctcgacaata   8700
cggcacaaac gttttttacg ccgcatttgg gatcggcgt caaggaagtt cggcttgaaa    8760
tcgagcggca ggcagcgatg aacatcatcc aggcactcgc tggtgaaaaa ccgatgggcg   8820
cgattaatca gccgtatccg ggagtaaagg cggcgtgaaa gcttggctgt tttggcggat   8880
gagagaagat tttcagcctg atacagatta aatcagaacg cagaagcggt ctgataaaac   8940
agaatttgcc tggcggcagt agcgcggtgg tcccacctga ccccatgccg aactcagaag   9000
tgaaacgccg tagcgccgat ggtagtgtgg ggtctcccca tgcgagagta gggaactgcc   9060
aggcatcaaa taaaacgaaa ggctcagtcg aagactgggc ctttcgtttt atctgttgt    9120 ttgtcggtga acgctctcct gagtaggaca atccgccgg gagcggattt gaacgttgcg    9180
aagcaacggc ccgagggtg gcgggcagga cgcccgccat aaactgccag gcatcaaatt    9240
aagcagaagg ccatcctgac ggatggcctt tttgcgtttc tacaaactct ttttgtttat   9300
ttttctaaat acattcaaat atgtatccgc tcatgagaca ataaccctga taaatgcttc   9360
aataatattg aaaaggaag agtatgagta ttcaacattt ccgtgtcgcc cttattccct    9420
tttttgcggc attttgcctt cctgtttttg ctcacccaga aacgctggtg aaagtaaaag   9480
```

```
atgctgaaga tcagttgggt gcacgagtgg gttacatcga actggatctc aacagcggta    9540
agatccttga gagttttcgc cccgaagaac gttttccaat gatgagcact tttaaagttc    9600
tgctatgtgg cgcggtatta tcccgtgttg acgccgggca agagcaactc ggtcgccgca    9660
tacactattc tcagaatgac ttggttgagt atcgacgtgg agtcgatcac tgtgattggc    9720 gaagggaag gcagcgctac ccaaatcgct agcttgctgg agaagctgaa acaaaccacg     9780
ggcattgatc tggcgaaatc cctaccgggt caatccgact cgcccgctgc gaagtcctaa    9840
gagatagcga tgtgaccgcg atcgcttgtc aagaatccca gtgatcccga accataggaa    9900
ggcaagctca atgcttgcct cgtcttgagg actatctaga tgtctgtgga acgcacattt    9960
attgccatca agcccgatgg cgttcagcgg ggtttggtcg gtacgatcat cggccgcttt   10020
gagcaaaaag gcttcaaact ggtgggccta agcagctga agcccagtcg cgagctggcc     10080
gaacagcact atgctgtcca ccgcgagcgc cccttcttca atggcctcgt cgagttcatc    10140
acctctgggc cgatcgtggc gatcgtcttg gaaggcgaag gcgttgtggc ggctgctcgc    10200
aagttgatcg gcgctaccaa tccgctgacg gcagaaccgg gcaccatccg tggtgatttt    10260
ggtgtcaata ttggccgcaa catcatccat ggctcggatg caatcgaaac agcacaacag    10320
gaaattgctc tctggtttag cccagcagag ctaagtgatt ggaccccac gattcaaccc      10380 tggctgtacg aataaggtct gcattccttc agagagacat tgccatgccc gtgctgcgat    10440
cgcccttcca agctgccttg ccccgctgtt tcgggctggc agccctggcg ttggggctgg    10500
cgaccgcttg ccaagaaagc agcgctccaa ttccctatag tgagtcgtat taaattcgta    10560
atcatggtca tagctgtttc ctgtgtgaaa ttgttatccg ctcacaattc cacacaacat    10620
acgagccgga agcataaagt gtaaagcctg gggtgcctaa tgagtgagct aactcacatt    10680
aattgcgttg cgctcactgc ccgctttcca gtcgggaaac ctgtcgtgcc agctgcatta    10740
atgaatcggc caacgcgcgg ggagaggcgg tttgcgtatt gggcgctctt ccgcttcctc    10800
gctcactgac tcgctgcgct cggtcgttcg gctgcggcga gcggtatcag ctcactcaaa    10860
ggcggtaata cggttatcca cagaatcagg ggataacgca ggaaagaaca tgtgagcaaa    10920
aggccagcaa aaggccagga accgtaaaaa ggccgcgttg ctggcgtttt tccataggct    10980 ccgccccct gacgagcatc acaaaaatcg acgctcaagt cagaggtggc gaaacccgac    11040
aggactataa agataccagg cgtttccccc tggaagctcc ctcgtgcgct ctcctgttcc    11100
gaccctgccg cttaccggat acctgtccgc ctttctccct tcgggaagcg tggcgctttc    11160
tcatagctca cgctgtaggt atctcagttc ggtgtaggtc gttcgctcca agctgggctg    11220
tgtgcacgaa ccccccgttc agcccgaccg ctgcgcctta tccggtaact atcgtcttga    11280
gtccaacccg gtaagacacg acttatcgcc actggcagca gccactggta acaggattag    11340
cagagcgagg tatgtaggcg gtgctacaga gttcttgaag tggtggccta actacggcta    11400
cactagaagg acagtatttg gtatctgcgc tctgctgaag ccagttacct tcggaaaaag    11460
agttggtagc tcttgatccg gcaaacaaac caccgctggt agcggtggtt ttttgtttg     11520 caagcagcag attacgcgca gaaaaaaagg atctcaagaa gatcctttga tcttttctac    11580
ggggtctgac gctcagtgga acgaaaactc acgttaaggg attttggtca tgagattatc    11640
aaaaaggatc ttcacctaga tccttttaaa ttaaaaatga agttttaaat caatctaaag    11700
tatatatgag taaacttggt ctgacagtta ccaatgctta atcagtgagg cacctatctc    11760
agcgatctgt ctatttcgtt catccatagt tgcctgactc cccgtcgtgt agataactac    11820
gatacgggag ggcttaccat ctggccccag tgctgcaatg ataccgcgag acccacgctc    11880
```

-continued

```
accggctcca gatttatcag caataaaacca gccagccgga agggccgagc gcagaagtgg    11940
tcctgcaact ttatccgcct ccatccagtc tattaattgt tgccgggaag ctagagtaag    12000
tagttcgcca gttaatagtt tgcgcaacgt tgttgccatt gctacaggca tcgtggtgtc    12060
acgctcgtcg tttggtatgg cttcattcag ctccggttcc caacgatcaa ggcgagttac    12120
atgatccccc atgttgtgca aaaaagcggt tagctccttc ggtcctccga tcgttgtcag    12180
aagtaagttg gccgcagtgt tatcactcat ggttatggca gcactgcata attctcttac    12240
tgtcatgcca tccgtaagat gcttttctgt gactggtgag tactcaacca agtcattctg    12300
agaatagtgt atgcggcgac cgagttgctc ttgcccggcg tcaatacggg ataataccgc    12360
gccacatagc agaactttaa aagtgctcat cattggaaaa cgttcttcgg ggcgaaaact    12420
ctcaaggatc ttaccgctgt tgagatccag ttcgatgtaa cccactcgtg cacccaactg    12480
atcttcagca tcttttactt tcaccagcgt ttctgggtga gcaaaaacag gaaggcaaaa    12540
tgccgcaaaa aagggaataa gggcgacacg gaaatgttga atactcatac tcttcctttt    12600
tcaatattat tgaagcattt atcagggtta ttgtctcatg agcggataca tatttgaatg    12660
tatttagaaa aataaacaaa taggggttcc gcgcacattt ccccgaaaag tgccacctga    12720
cgcgccctgt agcggcgcat taagcgcggc gggtgtggtg gttacgcgca gcgtgaccgc    12780
tacacttgcc agcgccctag cgcccgctcc tttcgctttc ttcccttcct ttctcgccac    12840
gttcgccggc tttccccgtc aagctctaaa tcggggcatc cctttagggt tccgatttag    12900
tgctttacgg cacctcgacc ccaaaaaact tgattagggt gatggttcac gtagtgggcc    12960
atcgccctga tagacggttt ttcgcccttt gacgttggag tccacgttct ttaatagtgg    13020
actcttgttc caaactggaa caacactcaa ccctatctcg gtctattctt ttgatttata    13080
agggattttg ccgatttcgg cctattggtt aaaaaatgag ctgatttaac aaaaatttaa    13140
cgcgaatttt aacaaaatat taacaaaata ttaacgttta caattt              13186
```

<210> SEQ ID NO 69
<211> LENGTH: 5094
<212> TYPE: DNA
<213> ORGANISM: E.coli

<400> SEQUENCE: 69

```
gacgaaaggg cctcgtgata cgcctatttt tataggttaa tgtcatgata ataatggttt     60
cttagacgtc aggtggcact tttcggggaa atgtgcgcgg aacccctatt tgtttatttt    120
tctaaataca ttcaaatatg tatccgctca tgagacaata accctgataa atgcttcaat    180
aatattgaaa aaggaagagt atgagtattc aacatttccg tgtcgccctt attcccttt     240 ttgcggcatt ttgccttcct gttttt gctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
```

-continued

```
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttaatt taaaaggatc taggtgaaga   1140
tccttttga taatctcatg accaaaatcc cttaacgtga gttttcgttc cactgagcgt   1200
cagacccgt agaaaagatc aaaggatctt cttgagatcc ttttttctg cgcgtaatct   1260
gctgcttgca aacaaaaaa ccaccgctac cagcggtggt ttgtttgccg gatcaagagc   1320
taccaactct ttttccgaag gtaactggct tcagcagagc gcagatacca atactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg tcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttgtga tgctcgtcag   1800
ggggggcggag cctatggaaa aacgccagca acgcggcctt tttacggttc ctggccttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcctga tgcggtattt tctccttacg catctgtgcg   2040
gtatttcaca ccgcatatgg tgcactctca gtacaatctg ctctgatgcc gcatagttaa   2100
gccagtatac actccgctat cgctacgtga ctgggtcatg gctgcgcccc gacacccgcc   2160
aacacccgct gacgcgccct gacgggcttg tctgctcccg gcatccgctt acagacaagc   2220
tgtgaccgtc tccgggagct gcatgtgtca gaggttttca ccgtcatcac cgaaacgcgc   2280
gaggcagctg cggtaaagct catcagcgtg gtcgtgaagc gattcacaga tgtctgcctg   2340
ttcatccgcg tccagctcgt tgagtttctc cagaagcgtt aatgtctggc ttctgataaa   2400
gcgggccatg ttaagggcgg ttttttcctg tttggtcact gatgcctccg tgtaagggg   2460
atttctgttc atgggggtaa tgataccgat gaaacgagag aggatgctca cgatacgggt   2520
tactgatgat gaacatgccc ggttactgga acgttgtgag ggtaaacaac tggcggtatg   2580
gatgcggcgg gaccagagaa aaatcactca gggtcaatgc cagcgcttcg ttaatacaga   2640
tgtaggtgtt ccacagggta gccagcagca tcctgcgatg cagatccgga acataatggt   2700
gcagggcgct gacttccgcg tttccagact ttacgaaaca cggaaaccga agaccattca   2760
tgttgttgct caggtcgcag acgttttgca gcagcagtcg cttcacgttc gctcgcgtat   2820
cggtgattca ttctgctaac cagtaaggca accccgccag cctagccggg tcctcaacga   2880
caggagcacg atcatgcgca cccgtggcca ggacccaacg ctgcccgaga tgcgccgcgt   2940
gcggctgctg gagatggcgg acgcgatgga tatgttctgc caagtaatgt gaagcttgca   3000
tgcctgcagg tcgactctag aggatccccc cctgttgaca attaatcatc ggctcgtata   3060
atgtgtggaa tcgtgagcgg ataacaattt cacacaagga gactgccatg aagcccaaag   3120
tcgtcctcac ccactgggtg cacccggaaa tcatcgaatt gttgtccgct agcgccgatg   3180
```

-continued

```
ttatccccaa caccacacgg gaaaccttgc cgcgttctga ggtaattgcg cgagccaaag      3240
atgcggatgc actcatggct ttcatgccgg acagcatcga cagcgcgttt ctcgaggaat      3300
gtccaaagct gcgtgtcatc ggcgccgcgc ttaaaggcta tgataacttc gatgtcaacg      3360
cctgcacacg ccacggtgta tggcttacga ttgtgccgga tttgcttacg atcccgaccg      3420
ctgaactgac tatcggcctt cttctcggtt tgacaaggca tatgctggaa ggcgataggc      3480
aaatccgtag cggacacttc caaggctggc ggccgacact atatggctct ggtttgacag      3540
gaaaaacgct tggcatcatt ggtatggggg cggtcggccg tgcaatcgcc cagcgcttgg      3600
ctggctttga aatgaatctc ttgtattgcg atccgattcc gctcaatgcc gaacaagaaa      3660
aggcttggca cgtacagcgc gtcacgctcg atgaactgct cgaaaaatgt gattatgtcg      3720
tgccgatggt tccgatggcc gcagagacac tgcatctgat cgatgccacc gcgttggcca      3780
agatgaaaac cggtagctac ctgatcaatg catgtcgcgg ctcggtcgtg gatgagaatg      3840
cggtgatagc agcactggcg tctggaaaac tagctggata tgcagccgat gtcttcgaga      3900
tggaagaatg gatacgcgct gatcgcccgc aggctatccc caaggcgctg ctcgacaata      3960
cggcacaaac gttttttacg ccgcatttgg gatcggcgt caaggaagtt cggcttgaaa      4020
tcgagcggca ggcagcgatg aacatcatcc aggcactcgc tggtgaaaaa ccgatgggcg      4080
cgattaatca gccgtatccg ggagtaaagg cggcgtgacg ccataaactg ccaggcatca      4140
aattaagcag aaggccatcc tgacggatgg ccttttttgcg tttctacaaa ctcttcctgt      4200
cgtcgggtac cgagctcgaa ttcactggcc gtcgttttac aacgtcgtga ctgggaaaac      4260
cctggcgtta cccaacttaa tcgccttgca gcacatcccc ctttcgccag ctggcgtaat      4320
agcgaagagg cccgcaccga tcgcccttcc caacagttgc gcagcctgaa tggcgaatgg      4380
cgcctgatgc ggtatttttct ccttacgcat ctgtgcggta tttcacaccg catacgtcaa      4440
agcaaccata gtacgcgccc tgtagcggcg cattaagcgc ggcgggtgtg gtggttacgc      4500
gcagcgtgac cgctacactt gccagcgccc tagcgcccgc tcctttcgct ttcttccctt      4560
cctttctcgc cacgttcgcc ggctttcccc gtcaagctct aaatcggggg ctccctttag      4620
ggttccgatt tagtgcttta cggcacctcg accccaaaaa acttgatttg ggtgatggtt      4680
cacgtagtgg gccatcgccc tgatagacgg ttttttcgccc tttgacgttg gagtccacgt      4740
tctttaatag tggactcttg ttccaaactg gaacaacact caaccctatc tcggctatt      4800 cttttgattt ataagggatt ttgccgattt cggcctattg gttaaaaaat gagctgattt      4860
aacaaaaatt taacgcgaat tttaacaaaa tattaacgtt tacaattta tggtgcactc      4920 tcagtacaat ctgctctgat gccgcatagt taagccagcc ccgacacccg ccaacacccg      4980
ctgacgcgcc ctgacgggct tgtctgctcc cggcatccgc ttacagacaa gctgtgaccg      5040
tctccgggag ctgcatgtgt cagaggtttt caccgtcatc accgaaacgc gcga          5094
```